(12) United States Patent
Henning et al.

(10) Patent No.: US 11,148,032 B2
(45) Date of Patent: Oct. 19, 2021

(54) EXERCISE CLASS APPARATUS AND METHOD

(71) Applicant: Equinox Holdings, Inc., New York, NY (US)

(72) Inventors: Elizabeth Kelly Henning, New York, NY (US); Jeffrey Scott Bruening, Los Angeles, CA (US); Gordon Thompson, III, New York, NY (US); Chirag Patel, Brooklyn, NY (US); Neel Magan Bakarania, Forest Hills, NY (US); Phuc Van Nguyen, Brooklyn, NY (US); Catherine Crowe Mark, New York, NY (US); John White, Brooklyn, NY (US); Jin Sung Yoo, Brooklyn, NY (US); Karen Rainert, Mamaroneck, NY (US); John Paul Benvenuto, New York, NY (US); Nicole Del Senno, Flushing, NY (US); Matthew Jacobs, New York, NY (US); David Hitchings, Kinnelon, NJ (US)

(73) Assignee: EQUINOX HOLDING, INC., New York, NY (US)

(*) Notice: Subject to any disclaimer, the term of this patent is extended or adjusted under 35 U.S.C. 154(b) by 506 days.

(21) Appl. No.: 14/868,268

(22) Filed: Sep. 28, 2015

(65) Prior Publication Data
US 2016/0089574 A1 Mar. 31, 2016

Related U.S. Application Data

(60) Provisional application No. 62/057,101, filed on Sep. 29, 2014, provisional application No. 62/066,150,
(Continued)

(51) Int. Cl.
*A63F 13/00* (2014.01)
*G16H 20/30* (2018.01)
(Continued)

(52) U.S. Cl.
CPC ...... *A63B 71/0622* (2013.01); *A63B 24/0062* (2013.01); *A63F 13/00* (2013.01); *G06Q 10/0639* (2013.01); *G16H 20/30* (2018.01)

(58) Field of Classification Search
CPC . A63F 13/00; G06F 19/3481; G06Q 10/0639; H04M 1/7253; A63B 24/00;
(Continued)

(56) References Cited

U.S. PATENT DOCUMENTS

| 5,089,960 A | * | 2/1992 | Sweeney, Jr. | ...... A63B 24/0087 463/6 |
| 5,213,555 A | * | 5/1993 | Hood | ................. A63B 71/0622 482/57 |

(Continued)

FOREIGN PATENT DOCUMENTS

| JP | WO2009031294 A1 * | 3/2009 |
| WO | WO 2009-031294 | 3/2009 |

OTHER PUBLICATIONS

US 7,772,502 B1, 05/2010, Holkkola (withdrawn)
(Continued)

*Primary Examiner* — Sundhara M Ganesan
*Assistant Examiner* — Shila Jalalzadeh Abyaneh
(74) *Attorney, Agent, or Firm* — DLA Piper LLP (US)

(57) ABSTRACT

Exercise class systems and methods may include a plurality of pieces of exercise equipment and/or a plurality of sensing systems adapted to be worn on people in the class, each piece of equipment or sensing system outputting plural exercise signals relating to exercise performance on the piece of equipment or of the person with the sensing system.
(Continued)

A computer system may also be provided. The computer system may include at least one electronic storage device which stores the plural signals from the pieces of equipment or sensing system and at least one processor which generates an output signal containing an animation corresponding to at least two of the exercise signals from each of the pieces of equipment or sensing systems. At least one display device, visible from each of the pieces of equipment or people in the class, may receive the output signal and display the animation.

71 Claims, 79 Drawing Sheets

Related U.S. Application Data filed on Oct. 20, 2014, provisional application No. 62/132,363, filed on Mar. 12, 2015.

(51) Int. Cl.
    *G06Q 10/06*     (2012.01)
    *A63B 71/06*     (2006.01)
    *A63B 24/00*     (2006.01)
    *H04M 1/72412*     (2021.01)

(58) Field of Classification Search
CPC ........ A63B 24/0003; A63B 2024/0025; A63B 2024/0055; A63B 2024/0059; A63B 24/0062; A63B 24/0084; A63B 2024/0096; A63B 71/0619; A63B 71/0622; A63B 2071/0636; A63B 2071/0641; A63B 2071/0647; A63B 2071/065; A63B 71/0669; A63B 2071/0694; A63B 2220/17; A63B 2220/13; A63B 2220/20; A63B 2220/30; A63B 2220/35; A63B 2220/40
See application file for complete search history.

(56) References Cited

U.S. PATENT DOCUMENTS

| | | | |
|---|---|---|---|
| 5,690,582 A | 11/1997 | Ulrich et al. | |
| 5,702,323 A | 12/1997 | Poulton | |
| 6,902,513 B1 * | 6/2005 | McClure ............ | A63B 24/0006 482/4 |
| 6,921,351 B1 * | 7/2005 | Hickman ............... | G16H 40/67 482/8 |
| 8,306,635 B2 | 11/2012 | Pryor | |
| 8,676,170 B2 | 3/2014 | Porrati et al. | |
| 8,892,219 B2 | 11/2014 | Pryor | |
| 9,101,837 B1 * | 8/2015 | Snyder ................. | A63F 13/212 |
| 9,174,085 B2 | 11/2015 | Foley et al. | |
| 9,409,053 B1 * | 8/2016 | Todd ........................ | G16H 20/30 |
| 2003/0022140 A1 * | 1/2003 | Chang ................... | A63F 13/212 434/247 |
| 2006/0040793 A1 * | 2/2006 | Martens ................. | A63B 69/16 482/8 |
| 2006/0063644 A1 | 3/2006 | Yang | |
| 2008/0015089 A1 * | 1/2008 | Hurwitz ............. | A63B 24/0087 482/8 |
| 2008/0096726 A1 * | 4/2008 | Riley ................. | G06Q 10/0639 482/8 |
| 2008/0161161 A1 * | 7/2008 | Pipinich ............. | A63B 69/0028 482/8 |
| 2008/0171636 A1 * | 7/2008 | Usui ................... | A63B 71/0686 482/8 |
| 2009/0098980 A1 * | 4/2009 | Waters ................... | G16H 20/30 482/8 |
| 2009/0233769 A1 | 9/2009 | Pryor | |
| 2009/0298649 A1 * | 12/2009 | Dyer .................. | A63B 24/0006 482/4 |
| 2009/0300513 A1 * | 12/2009 | Nims ...................... | A63F 13/65 715/747 |
| 2012/0253484 A1 | 10/2012 | Burich | |
| 2013/0041590 A1 * | 2/2013 | Burich ................. | A61B 5/0024 702/19 |
| 2013/0190135 A1 | 7/2013 | Pryor | |
| 2013/0210578 A1 * | 8/2013 | Birrell ................ | A63B 22/0664 482/4 |
| 2013/0241696 A1 | 9/2013 | Fabrizio | |
| 2014/0038781 A1 * | 2/2014 | Foley ..................... | A63B 22/06 482/9 |
| 2014/0073481 A1 * | 3/2014 | Aibara ................... | A61B 5/681 482/1 |
| 2014/0080556 A1 * | 3/2014 | Knutsson ................ | A63F 13/79 463/7 |
| 2014/0244575 A1 | 8/2014 | Giudici et al. | |
| 2015/0157895 A1 | 6/2015 | Bettini | |
| 2017/0147775 A1 * | 5/2017 | Ohnemus ............... | G16H 15/00 |
| 2017/0286641 A1 * | 10/2017 | Dugan ................. | A63F 13/428 |

OTHER PUBLICATIONS

International Search Report issued in PCT/US2015/052728 dated Jan. 14, 2016.
Written Opinion issued in PCT/US2015/052728 dated Jan. 14, 2016.
International Preliminary Report on Patentability issued in PCT/US2015/052728 dated Apr. 4, 2017.
Great Britain Office Action in Application No. GB1704807.5 dated May 29, 2020.
GB Office Acction in Application No. GB1704807.5 dated Jan. 29, 2021.
GB Office Action in Application No. GB1704807.5 dated Jun. 23, 2021.

* cited by examiner

Studio Cycling Diagram

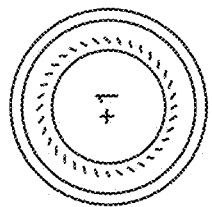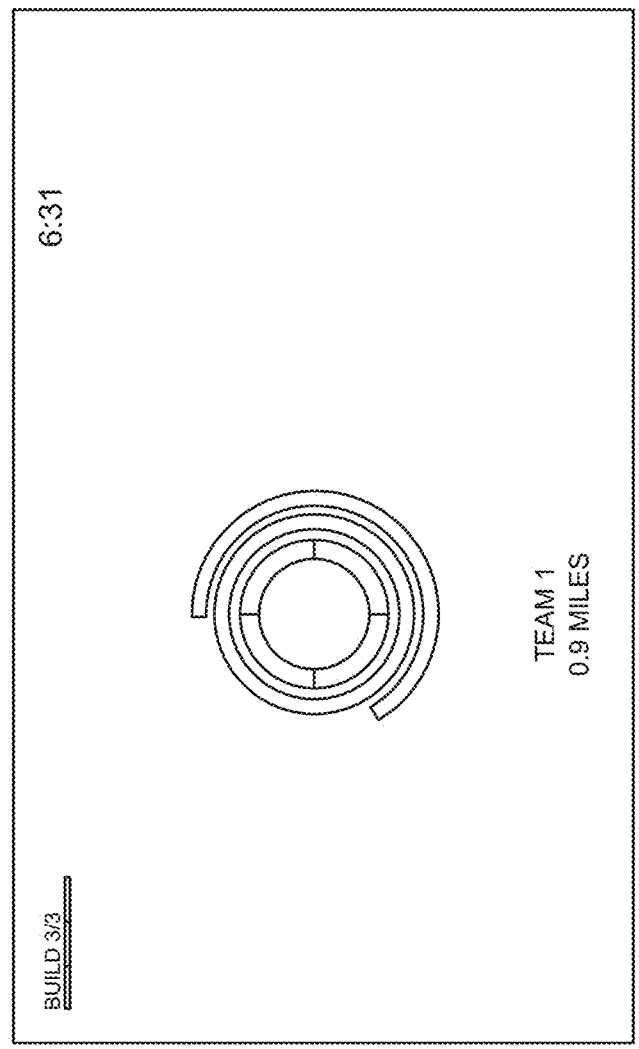
Fig. 31

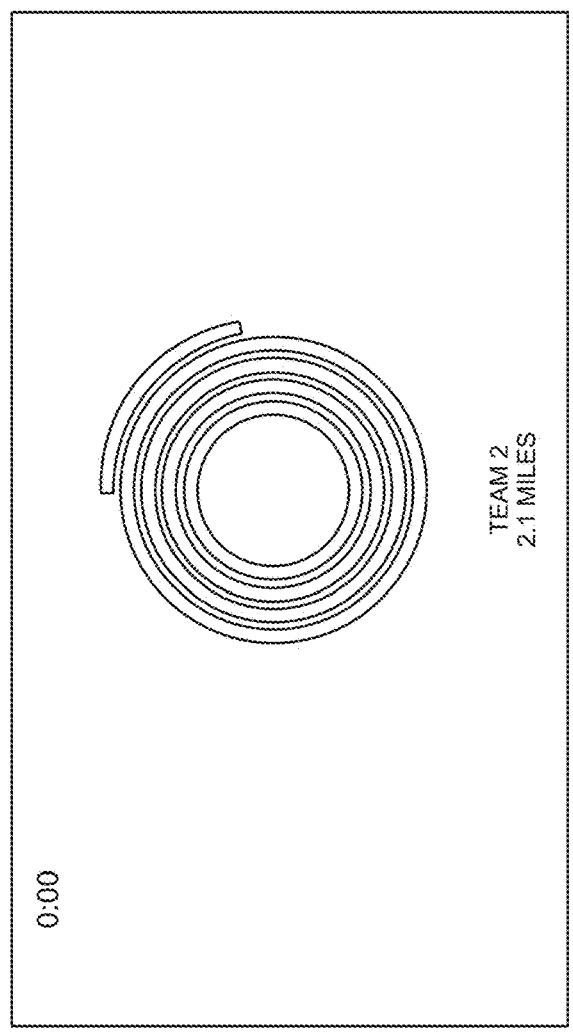
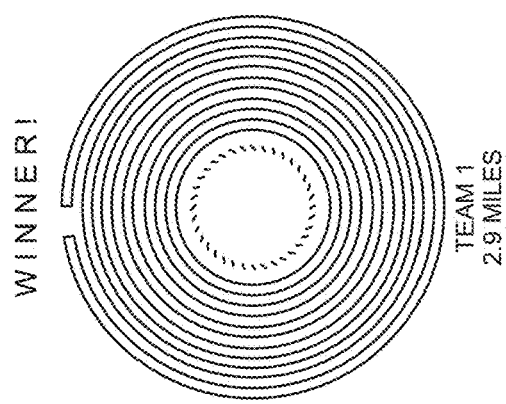
Fig. 32

**WELCOME!
PLEASE CONFIRM YOUR CLASS**

SIGNATURE CYCLING – BURN

COLLEEN CONLON

THURSDAY, SEPTEMBER 11

6:45 – 7:30 PM

50TH ST

EDIT

✓ CONFIRM

Fig. 44

FLOW 2 BIKE DATA FLOW

This diagram show how bike from the server is sent to the connected cycling application.

CLASS START ALERT

EXERCISE CLASS APPARATUS AND METHOD

CROSS-REFERENCE TO RELATED APPLICATIONS

This application claims the benefit of and priority to U.S. Provisional Patent Application Nos. 62/057,101, filed Sep. 29, 2014, 62/066,150, filed Oct. 20, 2014 and 62/132,363, filed Mar. 12, 2015. The contents of all of these applications are incorporated herein by reference in their entirety.

BRIEF DESCRIPTION OF THE DRAWINGS

FIGS. 5-43 illustrate games that may be implemented on an exercise system according to an embodiment of the invention.

FIGS. 44-52 illustrate displays of an instructor console in an exercise system according to an embodiment of the invention.

DETAILED DESCRIPTION OF SEVERAL EMBODIMENTS

An exercise system is disclosed appropriate for an exercise class. The exercise class may employ any type of exercise equipment or no equipment at all. Although embodiments described herein employ stationary bicycles, alternatively, treadmills, elliptical trainers, stair climbers or any other type of exercise equipment may be employed. Such exercise equipment may produce exercise signals which indicate a level of performance on the equipment. For example, conventional stationary bicycles may produce data relating to the rotational rate at which a user is pedaling, the power being exerted by the user, distance and energy. The rotational rate may indicate the number of revolutions in a fixed period of time of the pedal or wheel of a stationary bicycle. If the exercise equipment is a treadmill, then a corresponding measurement may relate to the speed at which the belt is moving. In this application, rotational rate, revolutions per minute (RPM), speed, miles per hour (MPH), etc. are considered to be the same thing. In this application, power, intensity, effort, wattage, etc. are all considered to be the same thing. When the equipment is a stationary bicycle, distance may represent a combination of rotational rate and power in a way that resembles gearing on an outdoor bicycle. On a treadmill, a corresponding measure may be a combination of belt speed and inclination. The energy measure may reflect the power expended over a period of time. In this application, calories, energy, joules and kilojoules are considered to be the same. When a person is exercising in a class without exercise equipment, or when the person is exercising on a piece of equipment, sensors may be provided to monitor the person's physiology. Such sensors may include speed of motion, distance traveled, energy expended, heart rate, blood pressure, blood-oxygen content, blood-sugar content, etc.

In embodiments described herein, exercise signals corresponding to any exercise performance measurements, such as those described above or other measurements, may be provided to a computer system which may include at least one electronic storage device for storing such exercise signals and at least one processor. The processor may generate an output signal which contains an animation corresponding to one or more of the exercise signals from the pieces of equipment or sensors on the class members. The animation may illustrate one or more games being played by participants in an exercise class. The output signal may be provided to at least display device, visible from the pieces of equipment or visible to people in the class to display the animation.

Figure 1:
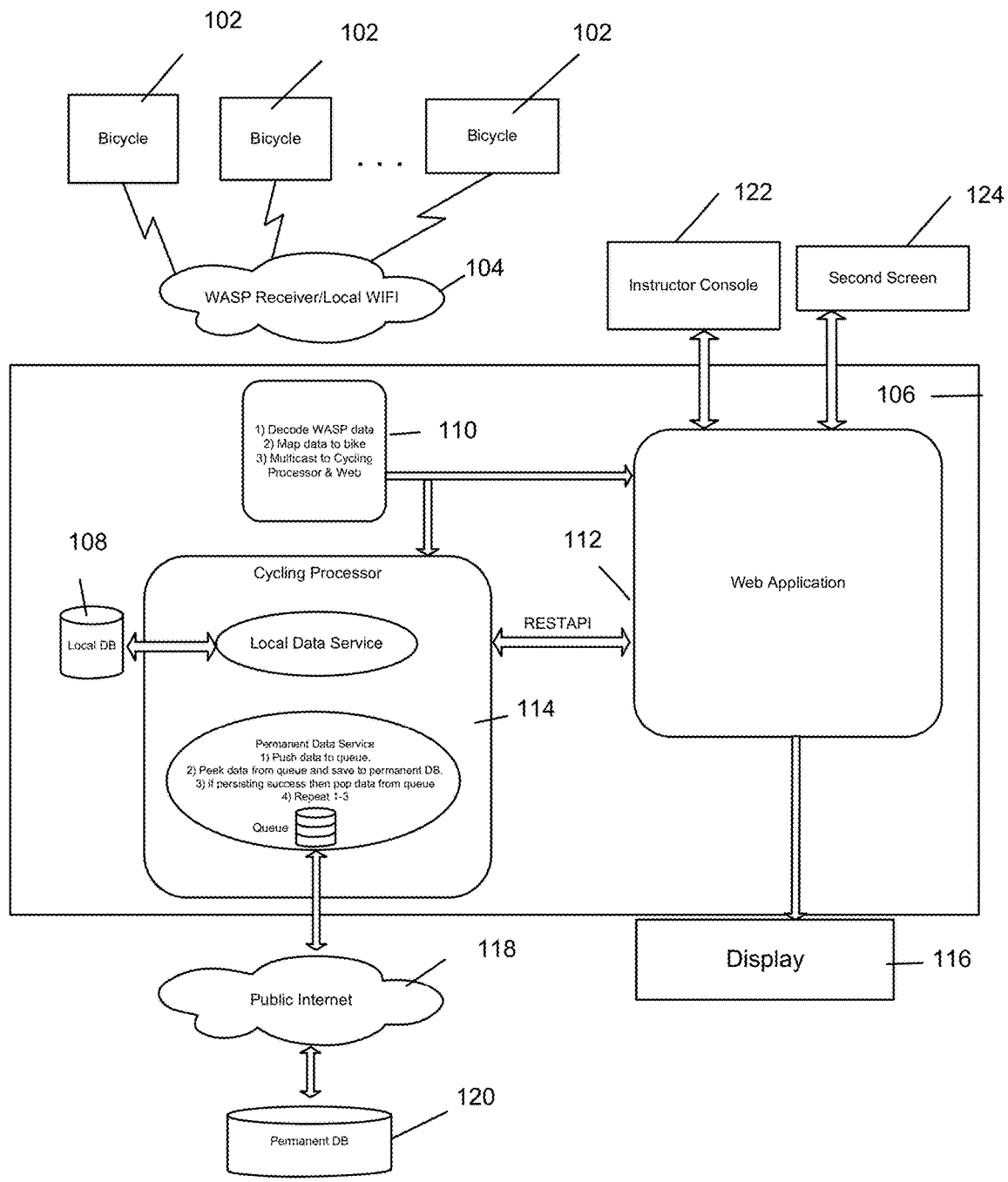
FIGS. 1 and 2 illustrate an exercise system according to an embodiment of the invention.

FIG. 1 illustrates such an exercise system. In this embodiment, stationary bicycles 102 are provided as the pieces of exercise equipment. Each bicycle may produce exercise signals which may include indications of rotational rate, power, distance, and/or energy, or any other performance measure. Such exercise signals may be transmitted wirelessly from bicycles 102 to WASP receiver 104 employing the ANT+ protocol. Receiver 104 may employ Wi-Fi to transmit the exercise signals to a computer system 106. Those skilled in the art will appreciate that any protocol(s) may be employed to transmit data from the exercise equipment and/or sensing systems to computer system 106. Computer system 106 may include at least one electronic storage device which stores, for example, local database 108. Computer system 106 may also include at least one processor which executes software. The software may include a module 110 which pre-processes data received from WASP receiver 104. Of course, data can be transmitted from bicycles 102 to computer system 106 using any wired or wireless channel and any protocol, e.g., Bluetooth. Pre-processor 110 may decode the WASP data and map the particular data to a bicycle within the fitness studio. The mapped data may be provided to web application software module 112 and cycling processor software module 114. Although software module 112 may be written as a web application, module 112 may also be written as a desktop application or in any manner known to those skilled in the art. As will be explained in greater detail below, web application module 112 may include software to be executed on at least one processor of computer system 106 to generate an output signal based on the exercise signals which is provided for display on display device 116. Alternatively, web application module 112 may include a portion running on another computer system to provide images for another display. Cycling processor module 114 may include software which is execute by at least one processor of computer system 106 to store the mapped data in a local database 108 on an electronic storage device of computer system 106. The software of cycling processor module 114 may also cause the mapped data to be queued and sent over a public network 118 to a permanent database 120. Data from database 120 may be made available to class participants using a variety of platforms.

The system of FIG. 1 may also include an instructor console 122. Console 122 may be a smartphone, a laptop computer, a desktop computer, a tablet, or any other electronic device that can communicate with computer system 106. The communication may occur over a wire or may be wireless, employing Wi-Fi or any other wireless protocol. Instructor console 122 may provide a graphic user interface to launch portions of the exercise class and to provide an indication of class performance.

The system of FIG. 1 may also include a second screen 124. Second screen 124 may be a device personal to each class member. For example, second screen 124 may be a smartphone, a tablet, a laptop computer, a desktop computer, or any other electronic device that can communicate with computer system 106. Therefore, although the second screen 124 may be temporally attached to a bicycle 102, the member may remove the second screen 124. The communication may occur over a wire or may be wireless, employing Wi-Fi or any other wireless protocol. Second screen 124 may provide a software application that allows a member to register for a class and allows a class member to see additional details of their cycling experience live in the class. A member registered for a cycling class may employ the application to connect to the local cycling processor software module 114. The second screen 124 will show data to the member as it is being streamed from the web application module 112. It is a personalized view of the larger game experience and synchronized to the game play as displayed on display 116. The second screen 124 may obtain the data it displays from the computer system 106 and not directly from bicycle 102.

Figure 2:
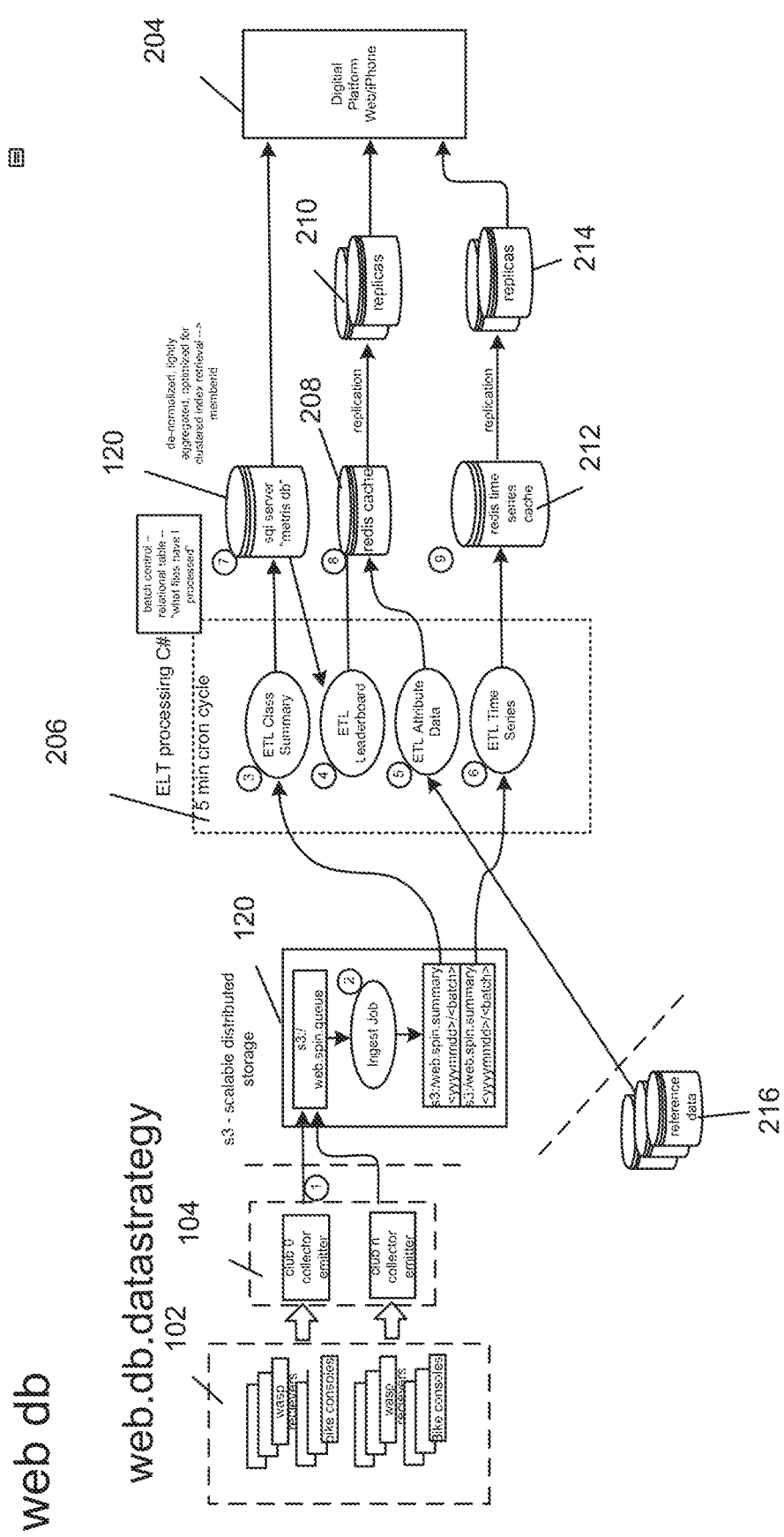

FIG. 2 illustrates the apparatus for distributing data to class participants outside of the studio. Data from bicycles 102 may be provided to WASP receivers 104 and may be stored in a database 120. Data stored in database 120 may include both detailed information concerning the performance of each class participant as well as summary data for each class. The summary information may be formatted by processor 206 and stored in long term store 120. Data in server 202 may be provided to any digital platform 204 such as a web access device or a smartphone for viewing by a participant. The class summary data from server 202 may also be provided to processor 206 to generate leader board information for the studio, region or system wide. That data may be stored in a cache 208 and then backed up to replicated instances 210 which may be provided to various devices of digital platform 204 for display. The detailed individual data from each class is also reformatted by processor 206 and provided to cache 212. This data may also be backed up to create replicas 214 which may be provided to various devices associated with digital platform 204 for access by participants.

Data provided on the leaderboard may be categorized by characteristics of the participants, such as gender and age. Information concerning characteristics of the participants may be obtained from data 216 and provided to processor 206 for formatting. Processor 206 may provide this data to cache 208 to augment the leaderboard data.

As noted above, exercise signals from bicycles 102 may be provided to web application module 212. Web application module 212 may generate class activities and corresponding displays that motivate participants. Different classes may be tailored to different training protocols. For example, a first training protocol may focus on building endurance and strength. A second training protocol may focus on optimizing caloric expenditure and performance. Whether a class of the first or second training protocol, web application module 112 may generate an output signal for display 116 which represents a series of games corresponding to the selected training protocol.

Figure 3:
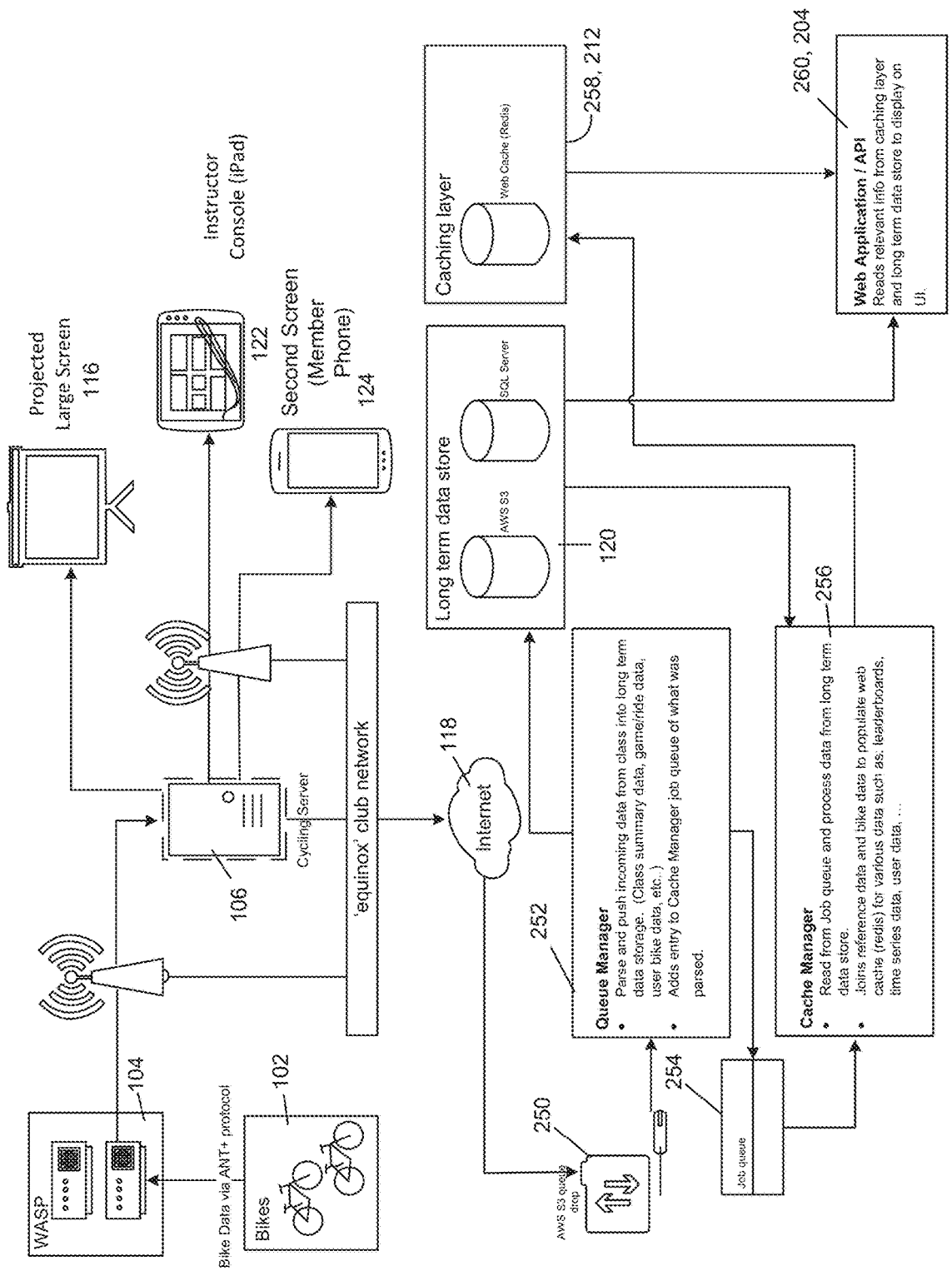
FIGS. 3 and 4 illustrate an exercise system according to another embodiment of the invention.
Figure 4:
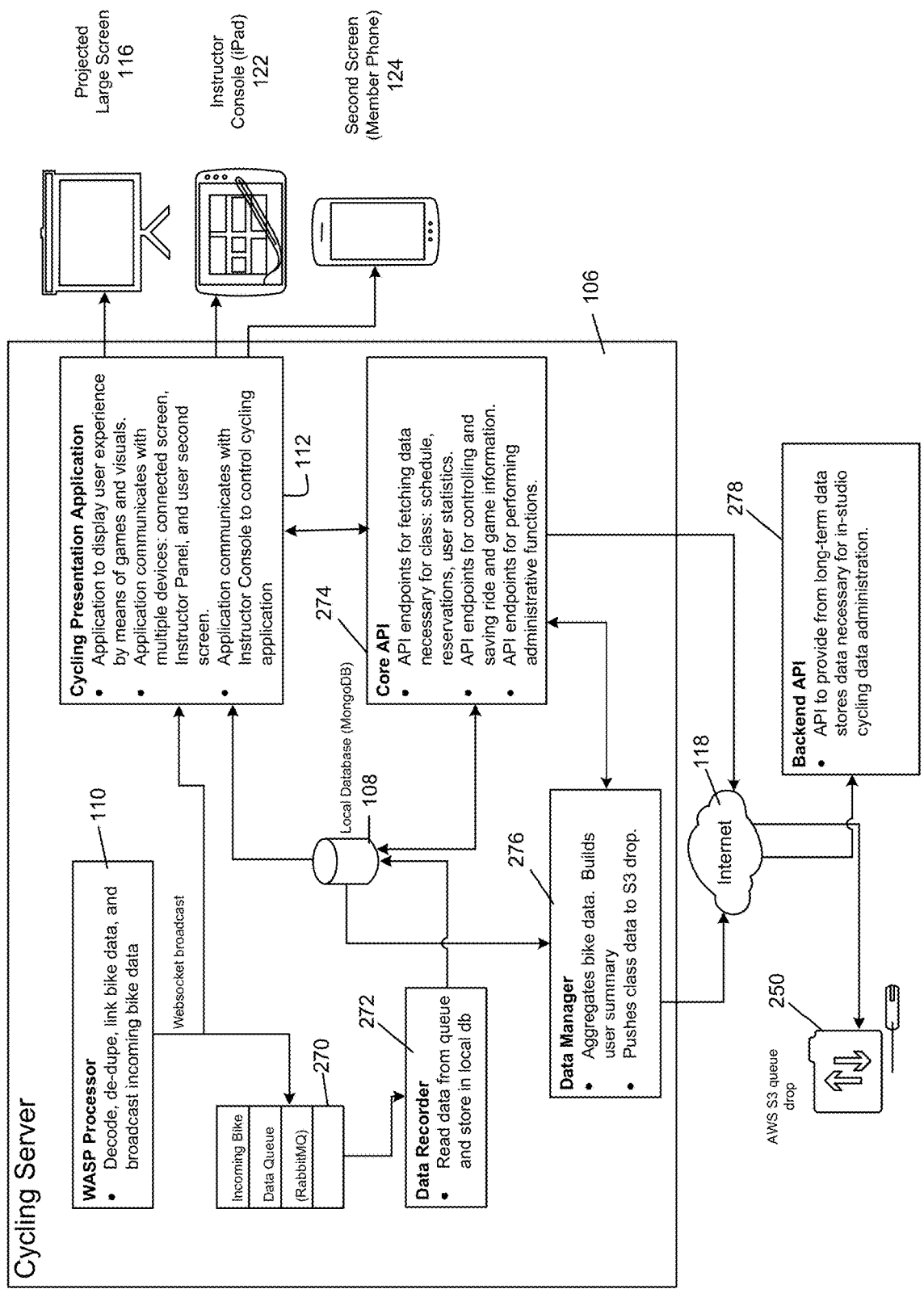

FIGS. 3 and 4 represent an alternative arrangement of an exercise system as compared to FIGS. 1 and 2. Components in FIGS. 3 and 4 that are similar to components in FIGS. 1 and 2 have been numbered similarly.

In a manner similar to that illustrated in FIG. 1, data from bicycles 102 is provided to cycling server 106 via WASP receivers 104. Of course, data from exercise devices or sensors may be applied to server 106 via any wired or wireless communications. Data from cycling server 106 is employed to drive displays on large screen 116, instructor console 122, and/or second screen 124. Data from cycling server 106 is also sent over a network 118, such as the Internet, for example, to queue 250. Queue manager 252 parses the data in the queue 250 and pushes the data into long term data store 120. This data includes class summary data, games/ride data, user bicycle data, etc. Queue manager 252 also adds an entry to the cache manager job queue 254 with information concerning what had been parsed. Cache manager 256 reads data from the job queue and also processes data from long term data store 120. Cache manager 256 joins reference data and bicycle data from long term data store 120 to populate cache 258, 212 for various data such as leader boards, time series data, user data, etc. Data from cache 258, 212 is provided to web application 260, 204 to allow post-class public access of the data.

FIG. 4 provides further details concerning cycling server 106. Data from bicycles 102 is received at processor 110. This data is provided to cycling presentation application 112 which employs the data to generate displays of games and other visuals. This data is employed to provide images on large screen 116, instructor console 122 and second screen 124. Data from processor 110 is also provided to queue 270. Data recorder 272 reads data from queue 270 and stores the data in local database 108. Core API 274 fetches the data necessary for a class, such as scheduling data, reservations and user statistics. Core API 274 also controls and saves ride and game information. Data manger 276 collects bicycle data from local database 108 and information concerning class schedules, reservations and user statistics to build user summaries. That data is transmitted through network 118 to queue 250 to be handled as described above with regard to FIG. 3. The data transmitted over network 118 is also applied to backend API 278 which provides from long term data store 120 data that is necessary for in-studio cycling administration of classes.

Data for each member is streamed via the web application API 112. Each local web application API 112 supports an authentication token to identify the member that is verified by the backend API 278. A secondary authorization is done to ensure that the member requesting personal information is registered for a particular class. Any member that is not registered for a class will not be able to view any data on second screen 124.

The web application API obtains information from two sources: live bicycle data collected by the cycling application running on computer system 106 and long term store 120. The cycling application on computer system 106 monitors for milestones, achievements, winners, etc. and pushes appropriate messaging to the second screen 124 as events occur.

Figure 67:
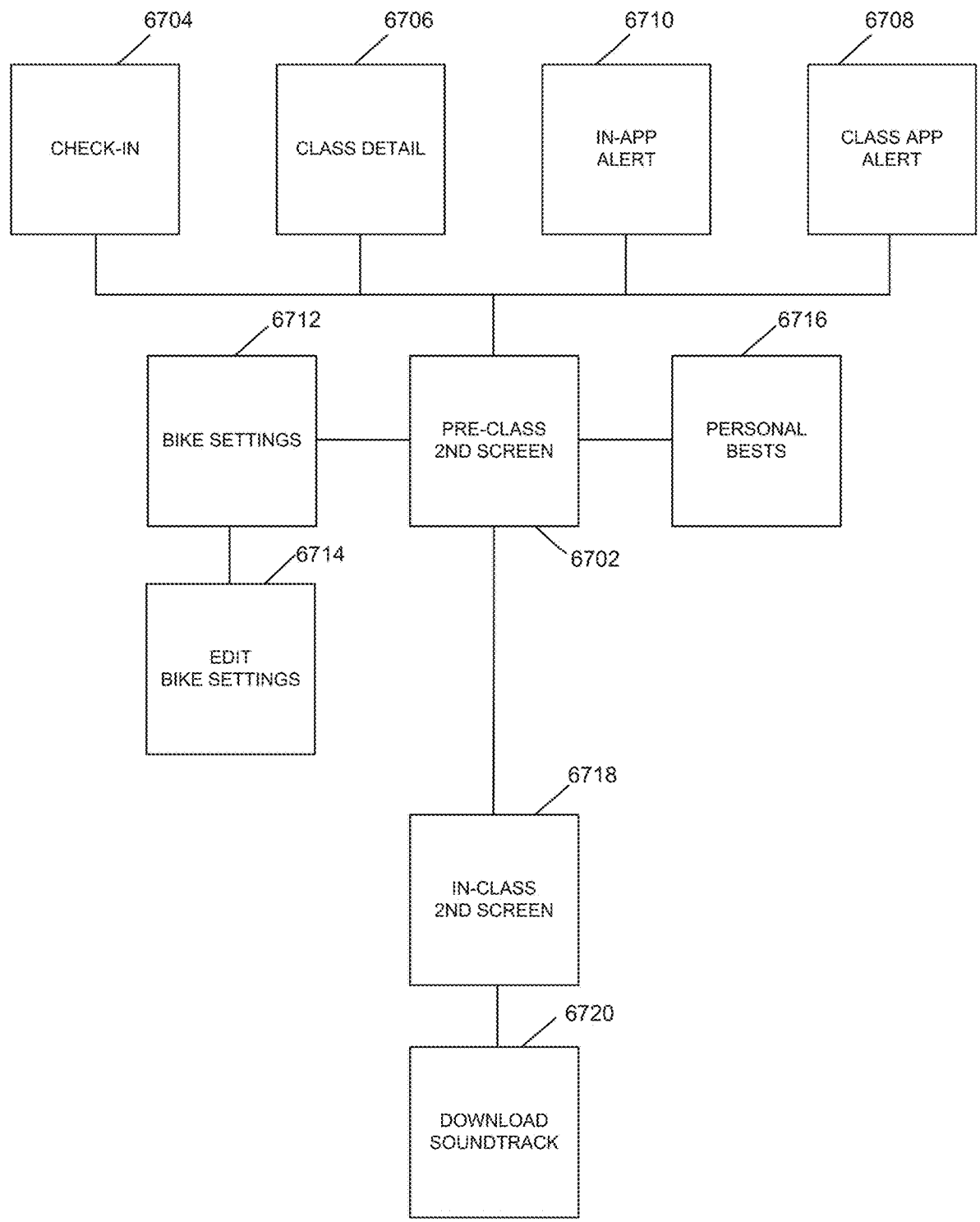
FIG. 67 illustrates the relationship of displays for a second screen in an exercise system according to an embodiment of the invention.

The organization of the application running on second screen 124 is illustrated in FIG. 67. Prior to class, a member may access a portion 6702 of the application relating to pre-class functionality. For example, the member may employ check-in module 6704 and may learn about the class in class detail module 6706. Once registered for a class, the application on second screen 124 may issue a class alert through module 6708 and may provide access to the in-class portion of the application at module 6710. A member is also able to view bicycle settings at module 6712 and edit those settings at module 6714. Finally, a member may review the member's personal best statistics employing module 6716.

Portion 6718 of the application running on second screen 124 drives displays on second screen 124 during class. Also, during class, module 6720 may be employed to download a soundtrack.

FIGS. 5-32 provide images that the output signal from web application module 112 may cause to be displayed on display device 116 in a class of the first training protocol. FIGS. 68-79 illustrate employing images on second screen 124 during the first training protocol. As noted above, a class of the first training protocol may be focused on building endurance and strength. The class may include three stages, each representing a hill climb. A recovery period may be provided between stages.

Figure 68:
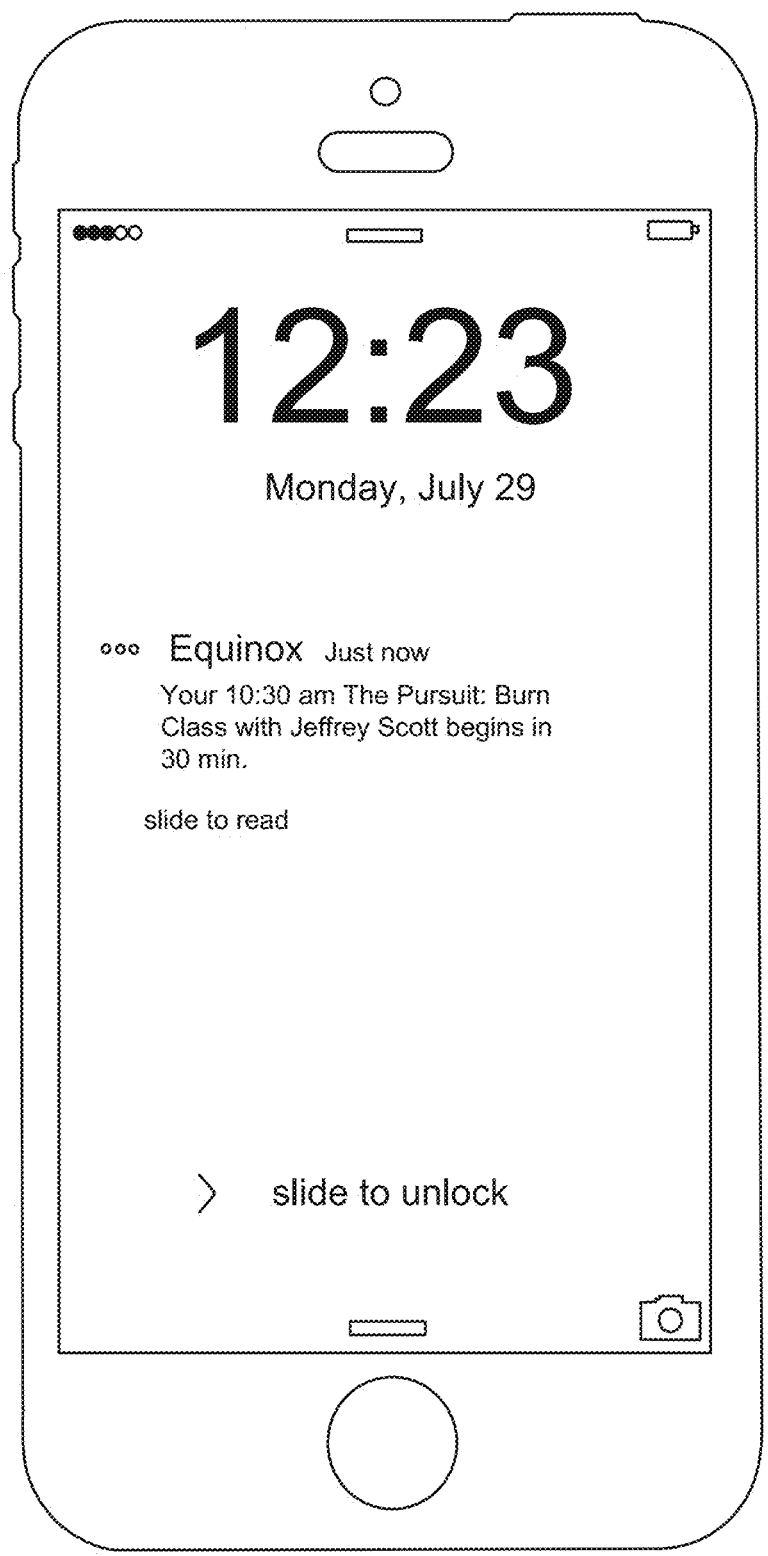
FIGS. 68-79 illustrate images for a second display in an exercise systems according to an embodiment of the invention.
Figure 69:
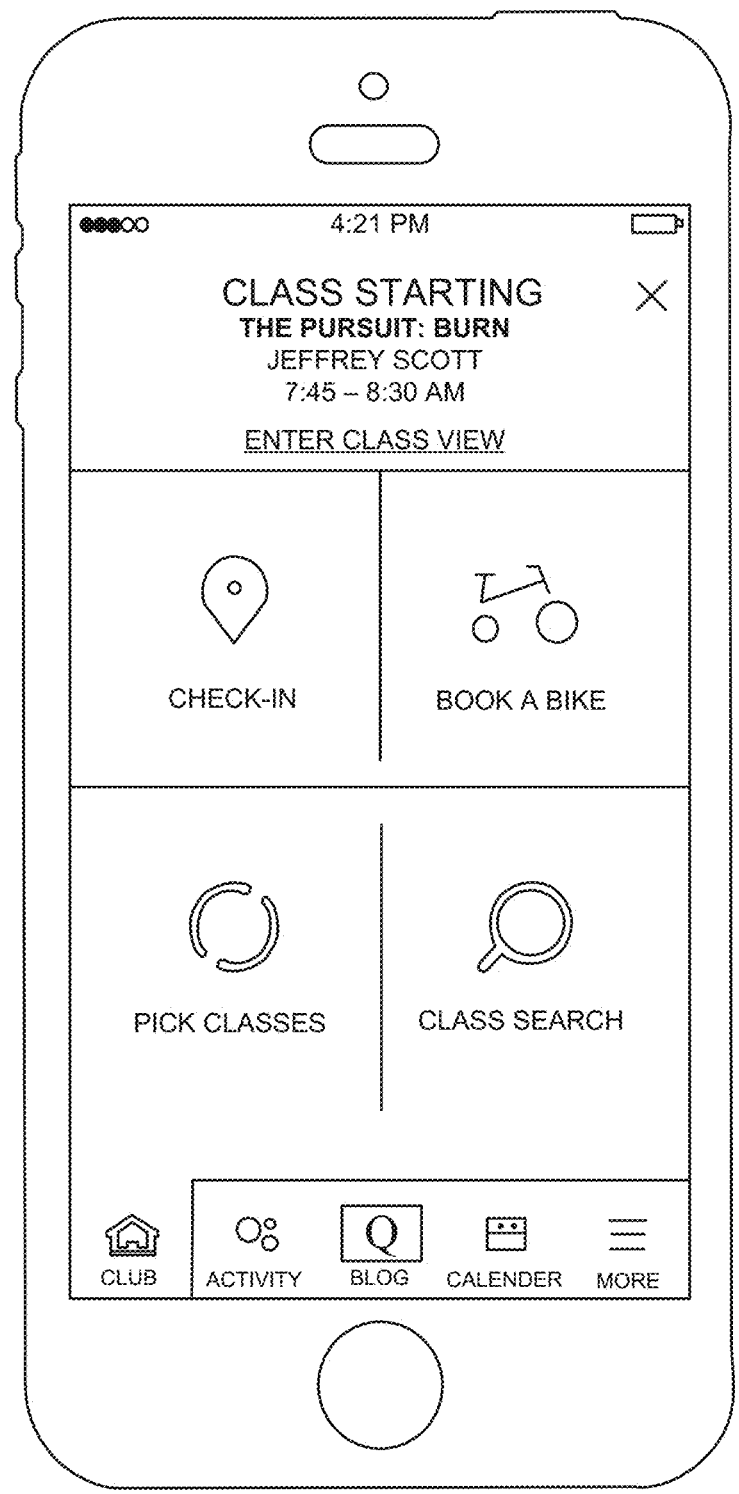
Figure 70:
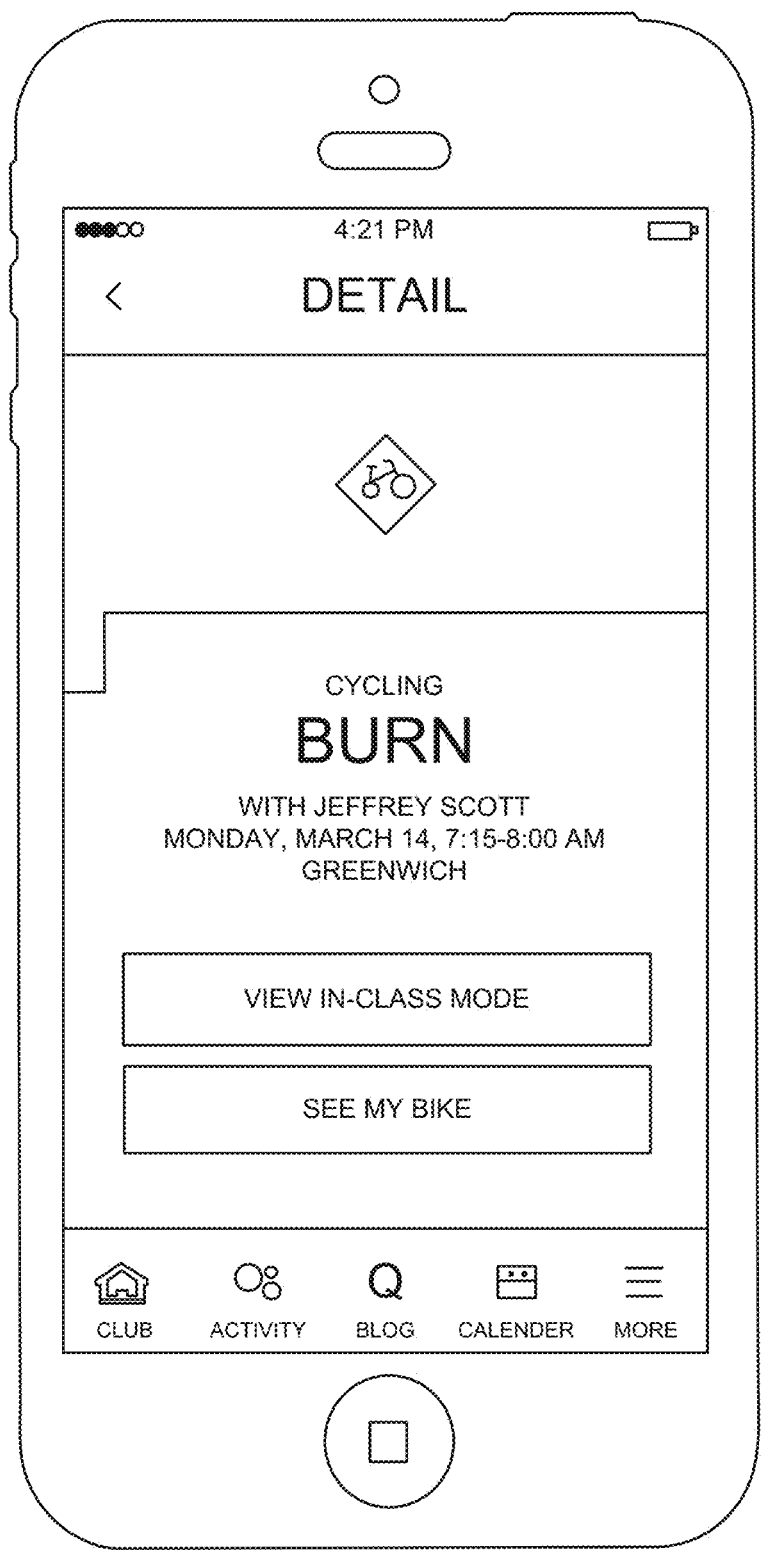
Figure 71:
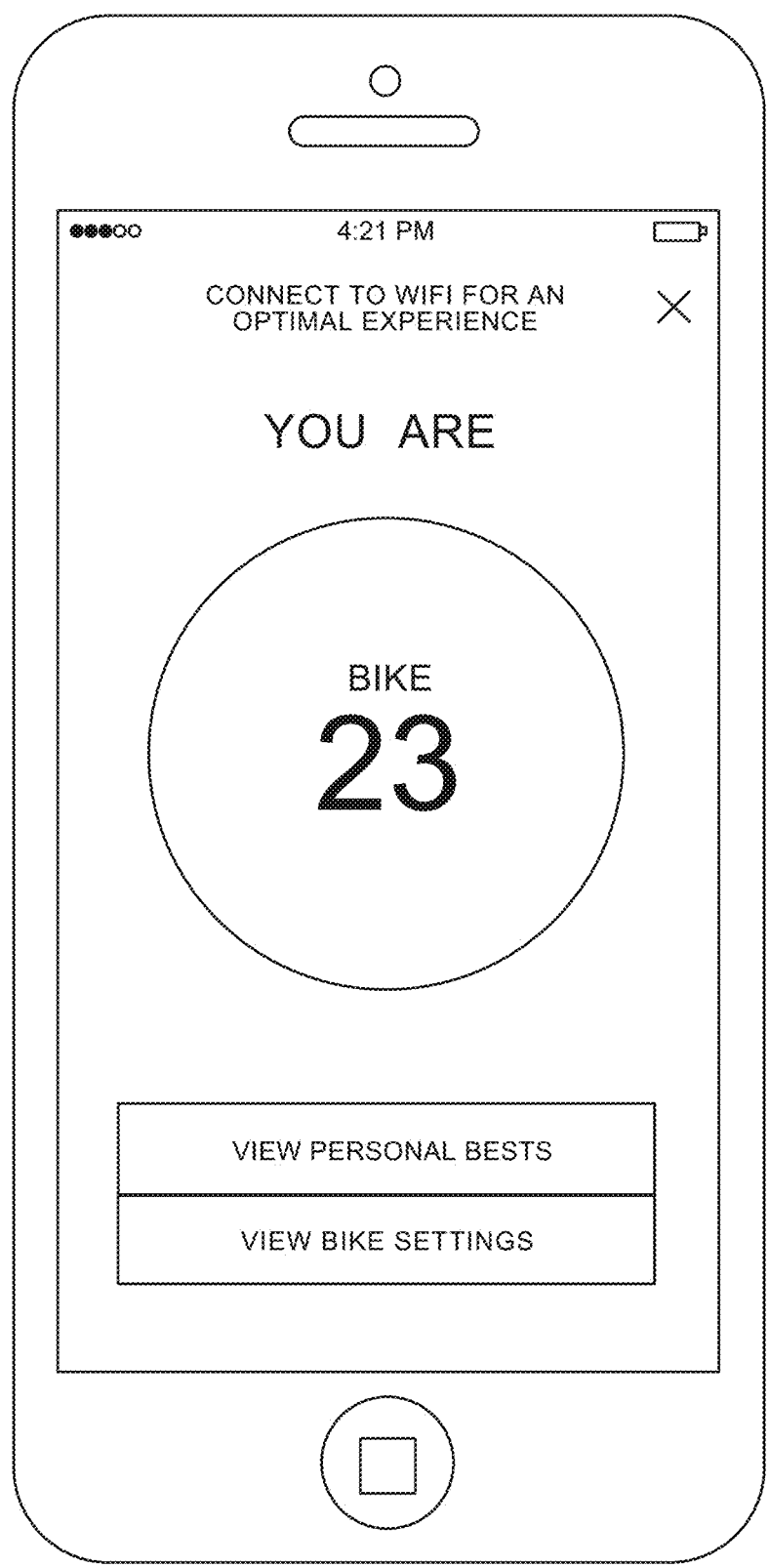
Figure 72:
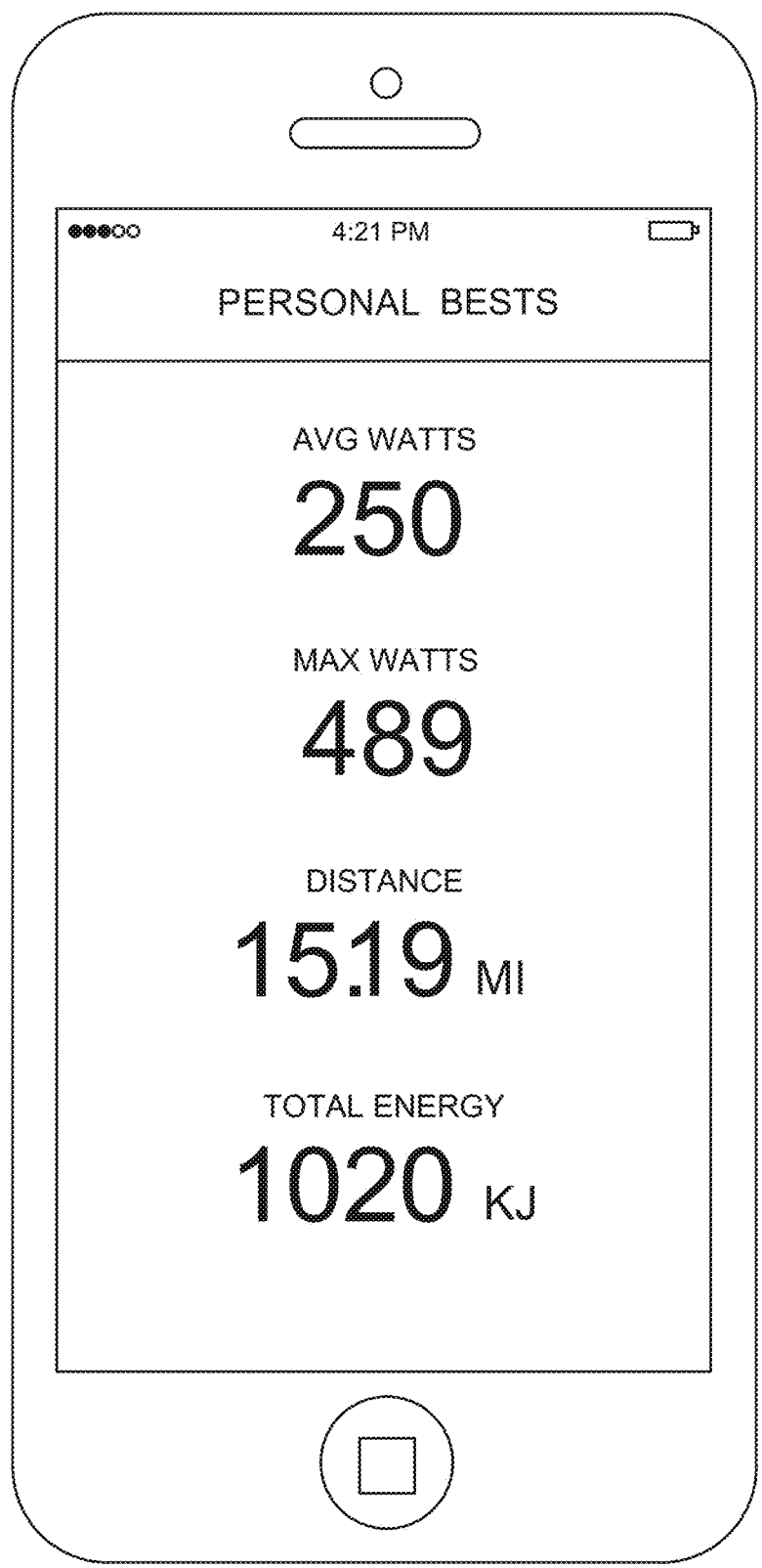
Figure 73:
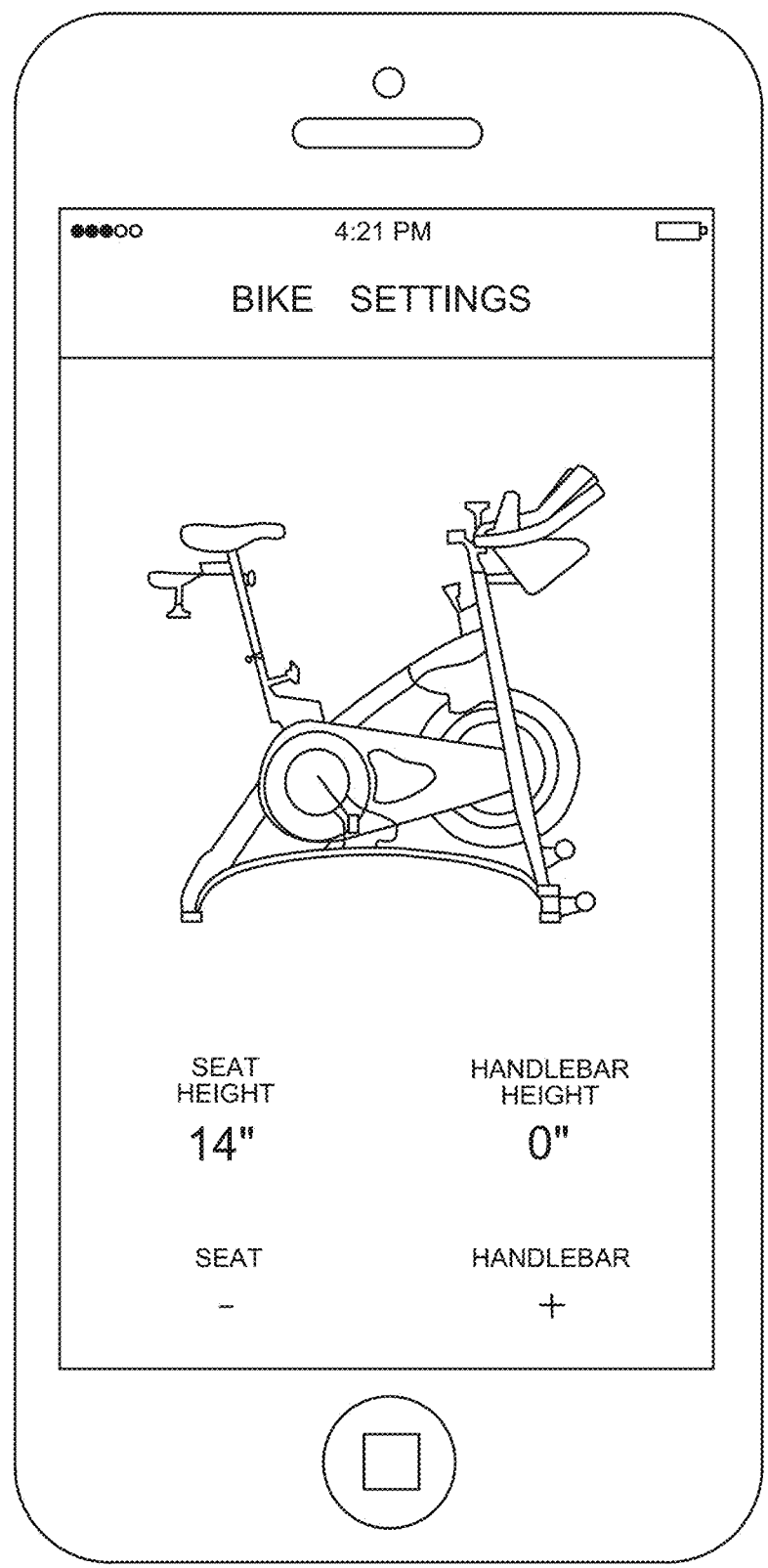

Once a member has registered for a class, second screen 124 may provide a reminder that the class is about to start as illustrated in FIG. 68. Subsequently, second screen 124 may display the image illustrated in FIG. 69 which provides a way for a member to engage the functionality of the application on second screen 124, including entering a class view for the class that is about to start. When a member enters the class view illustrated in FIG. 70, the in-class mode may be selected. Once selected, second screen 124 may display the image of FIG. 71. The image indicates the members bicycle number and allows the member to view personal best or bicycle settings. If the member selects personal best, an image such as in FIG. 72 may be displayed that shows past performance of the member. If bicycle settings is selected, an image such as in FIG. 73 may provide guidance for the member in adjusting the bicycle. The data displayed on second screen 124 may include cumulative data for the individual member over a class.

Figure 5:
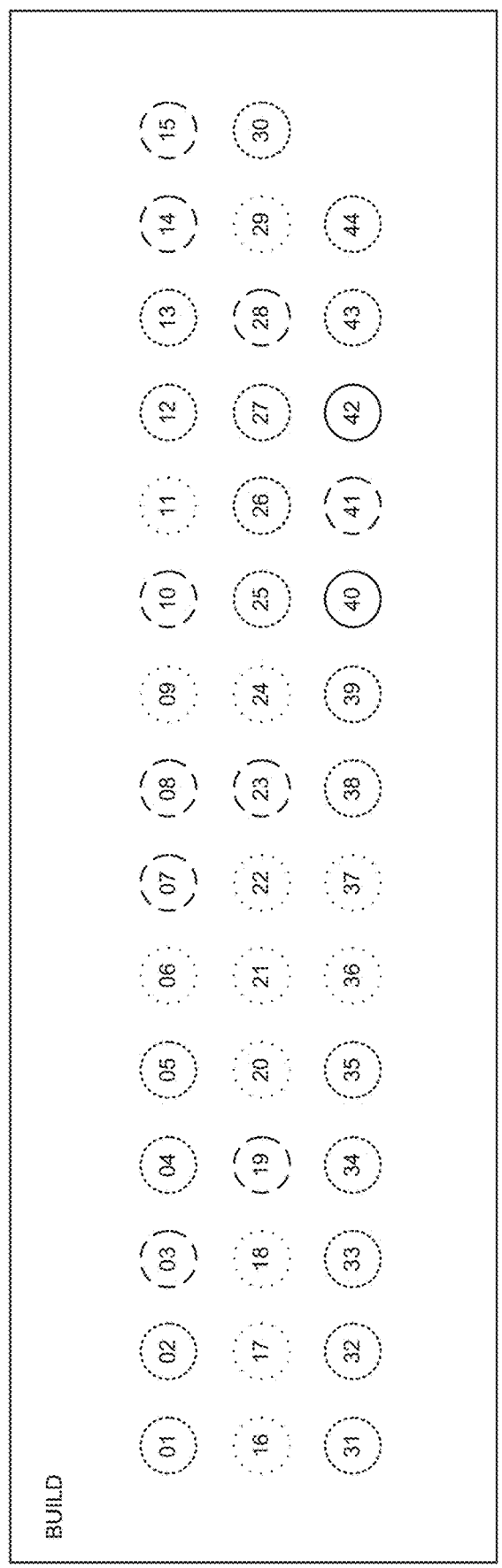

FIG. 5 represents the image displayed by display device 116 as participants arrive and begin warming up. Each bicycle may be represented by a number. As the participant begins to pedal, the circle around the corresponding number may rotate at a rate corresponding to the participant's rotational rate in pedaling the bicycle. The width of the line forming the circle may correspond to the power begin exerted by the participant. The line may be made up of segments, with the number of segments decreasing and the length of each segment increasing as the exerted power increases. With a stationary bicycle, the power may be related to the resistance setting selected by the participant. The power that a participant is able to generate may be dependent on a participant's weight. For example, it is much easier to achieve higher watts for someone who is 250 pounds as compared to someone who is 120 pounds. As a result, web application module 112 may cause the wattage required to thicken the line forming each circle to be different for men and women, using gender as a proxy for weight.

Figure 6:
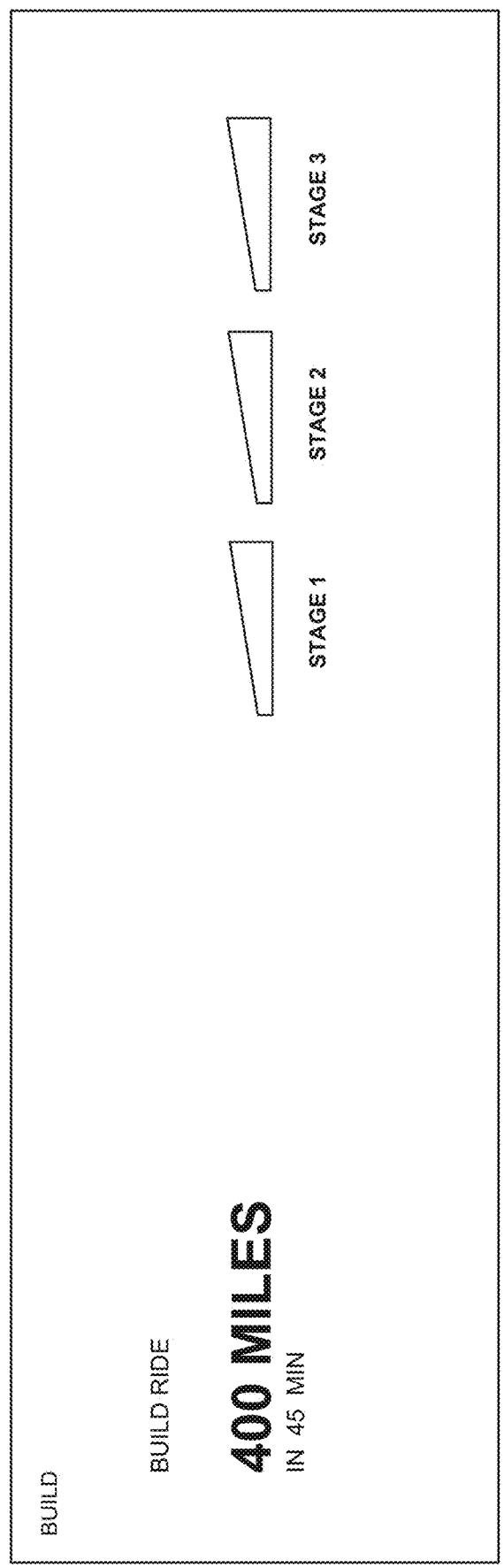
Figure 74:
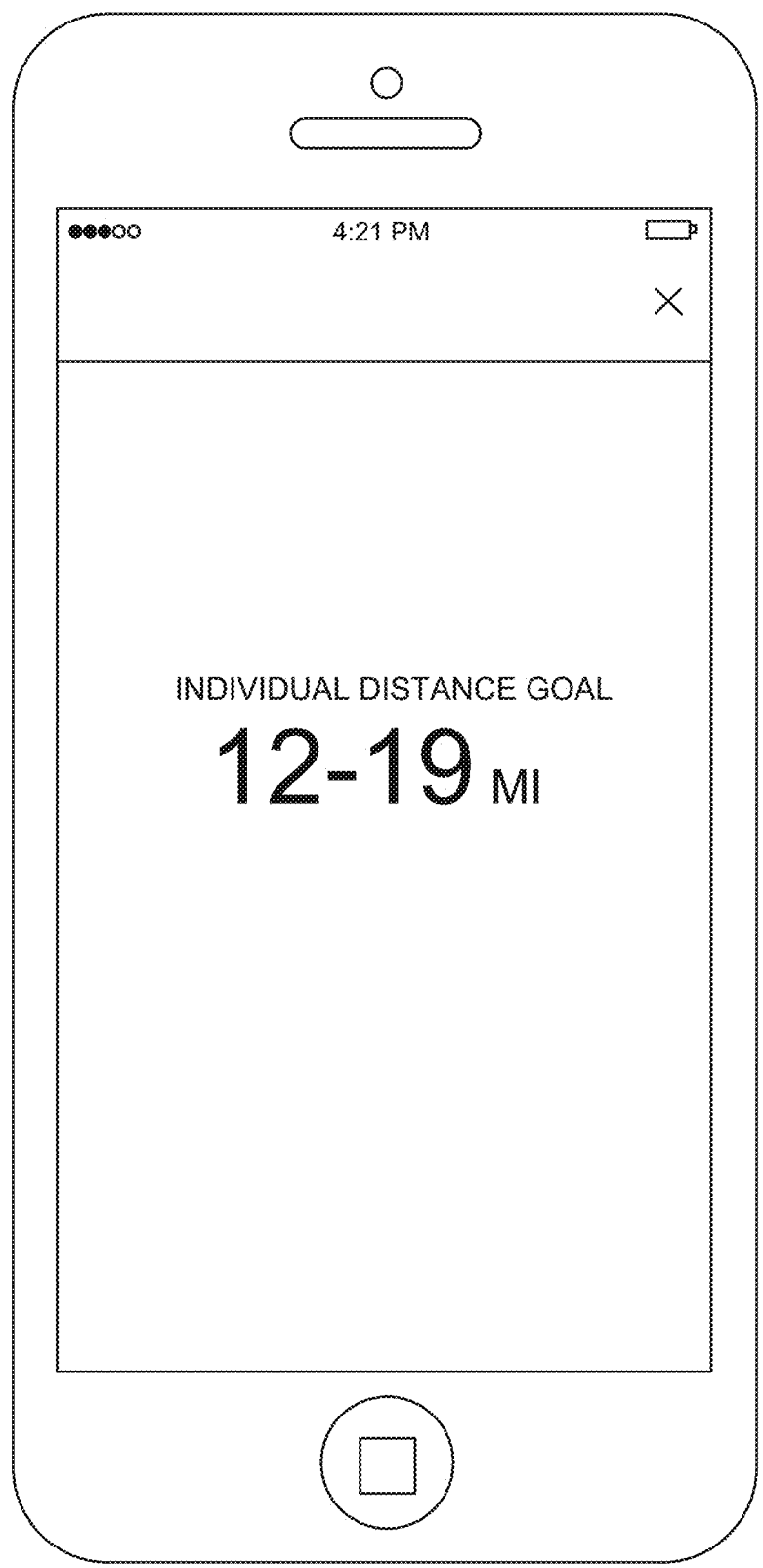

FIG. 6 is an overview of the class. As noted above, the class may consist of three stages with adjacent stages being separated by a recovery period. FIG. 6 also illustrates that the overall goal for the class may be to cover 400 overall miles in 45 minutes as set by the instructor on the instructor console 122. The class goal may be dynamic based on the number of riders in the room (e.g., 12 miles per rider) and other factors. At the same time, second screen 124 may display the image of FIG. 74 showing the individual member's energy goal for the training session.

Figure 7:
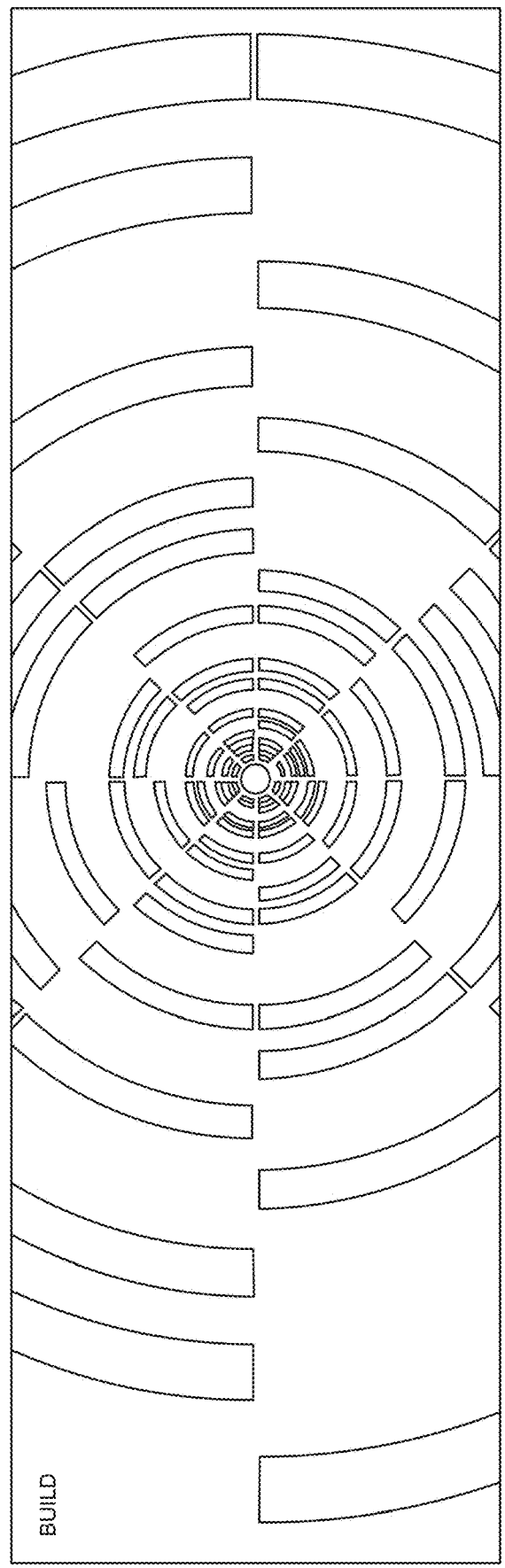

As illustrated in FIG. 7, at the beginning of the class, a warm-up animation may be provided. The animation may be dynamic and responsive to the exercise signals coming from the bicycles.

Figure 8:
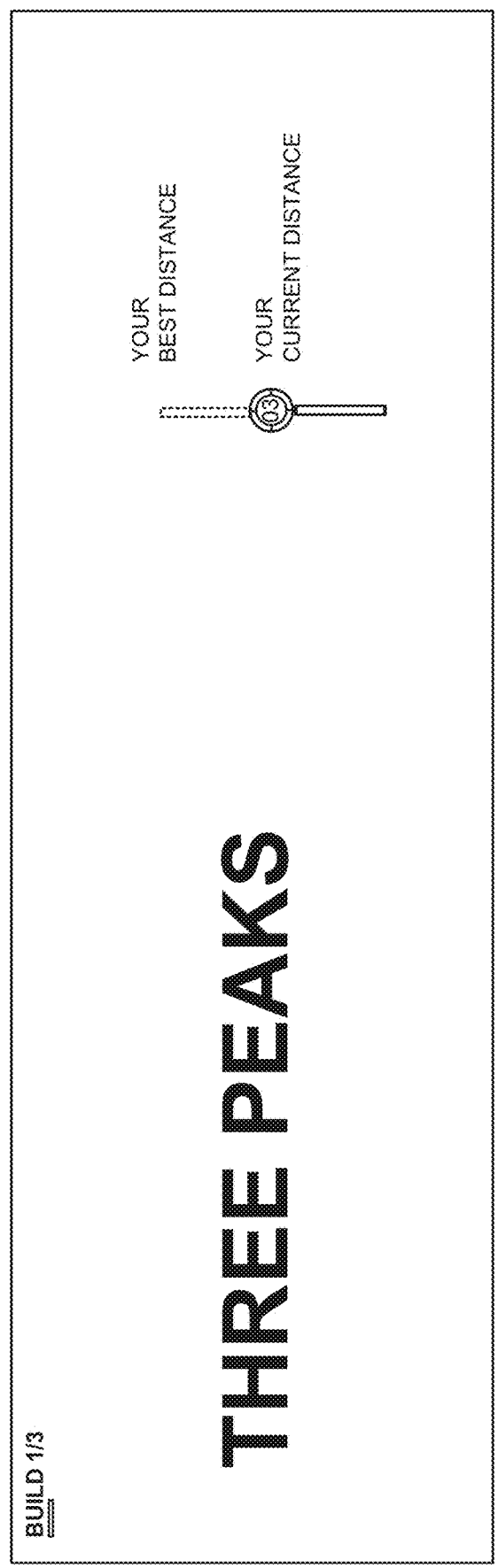

FIG. 8 illustrates the beginning of the first stage called "three-peaks." This game may provide an animation of the performance of each individual participant in three rounds over nine minutes. As represented in FIG. 8, the performance of each participant may be indicated by a rotating circle, where the rate of rotation may correspond to the rotational rate of the participant, the thickness of the line forming the circle may correspond to the power being exerted by the participant and the distance that the circle moves along a vertical path may correspond to the distance measurement of the participant. The vertical path may be divided into segments, with each segment representing a fixed distance.

Figure 9:
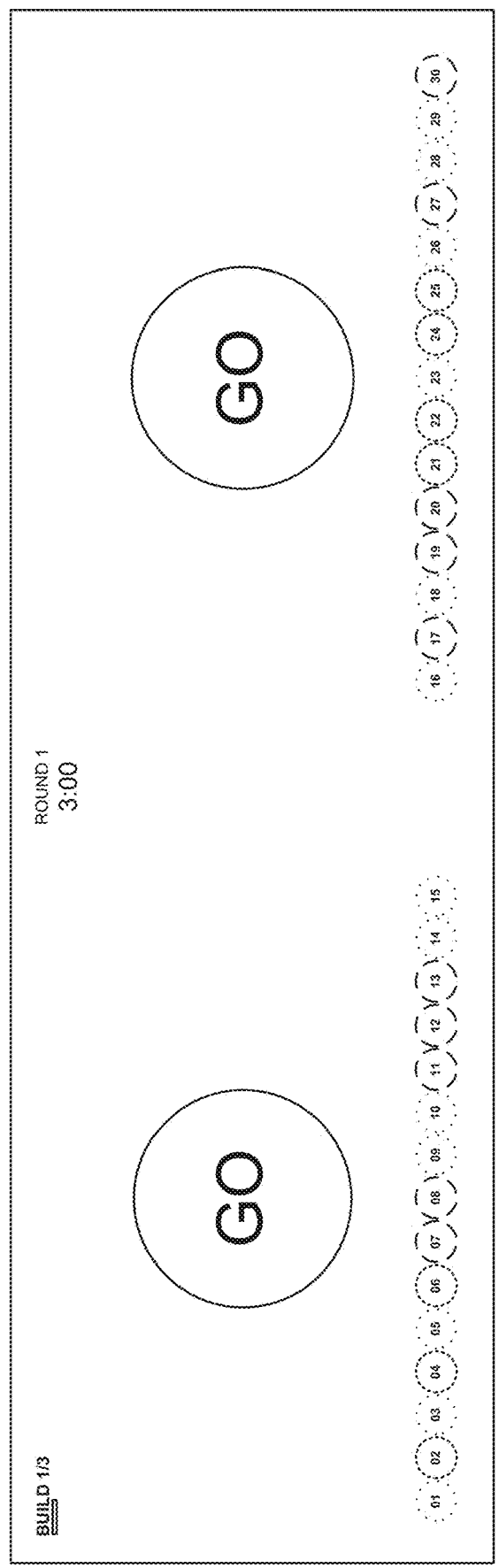

As illustrated in FIG. 9, as the first round begins, the circle corresponding to each participant may be toward the bottom of the image. Already, the circle for each participant may indicate the rotational rate and power of each participant.

Figure 10:
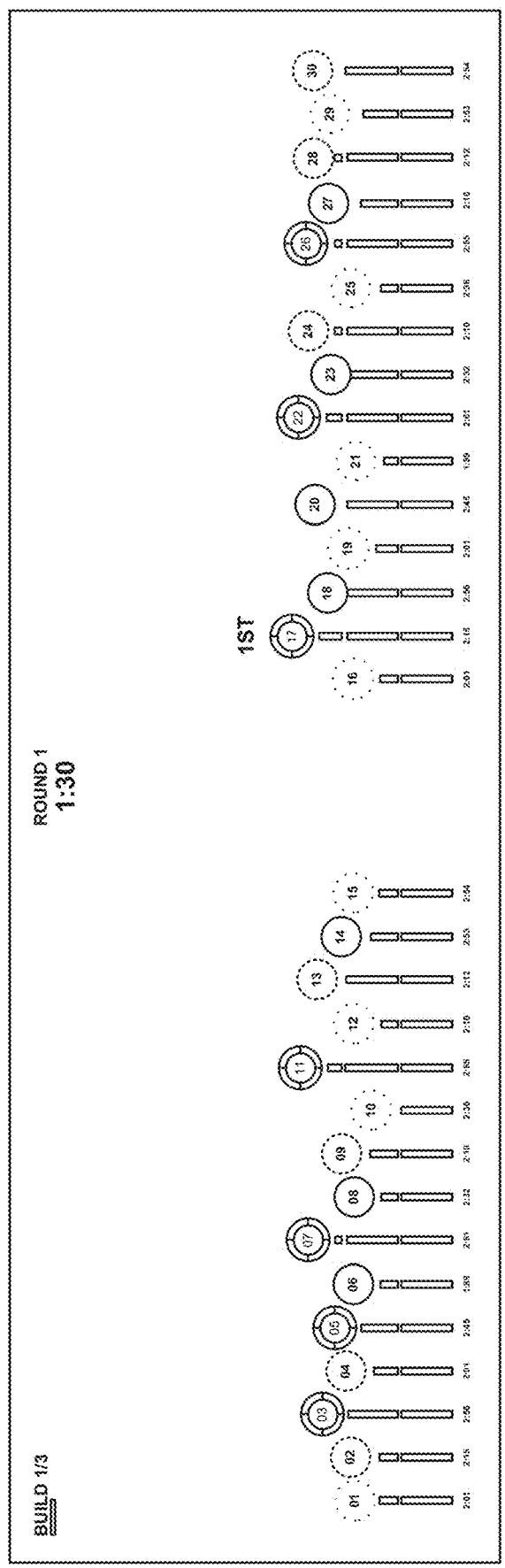
Figure 75:
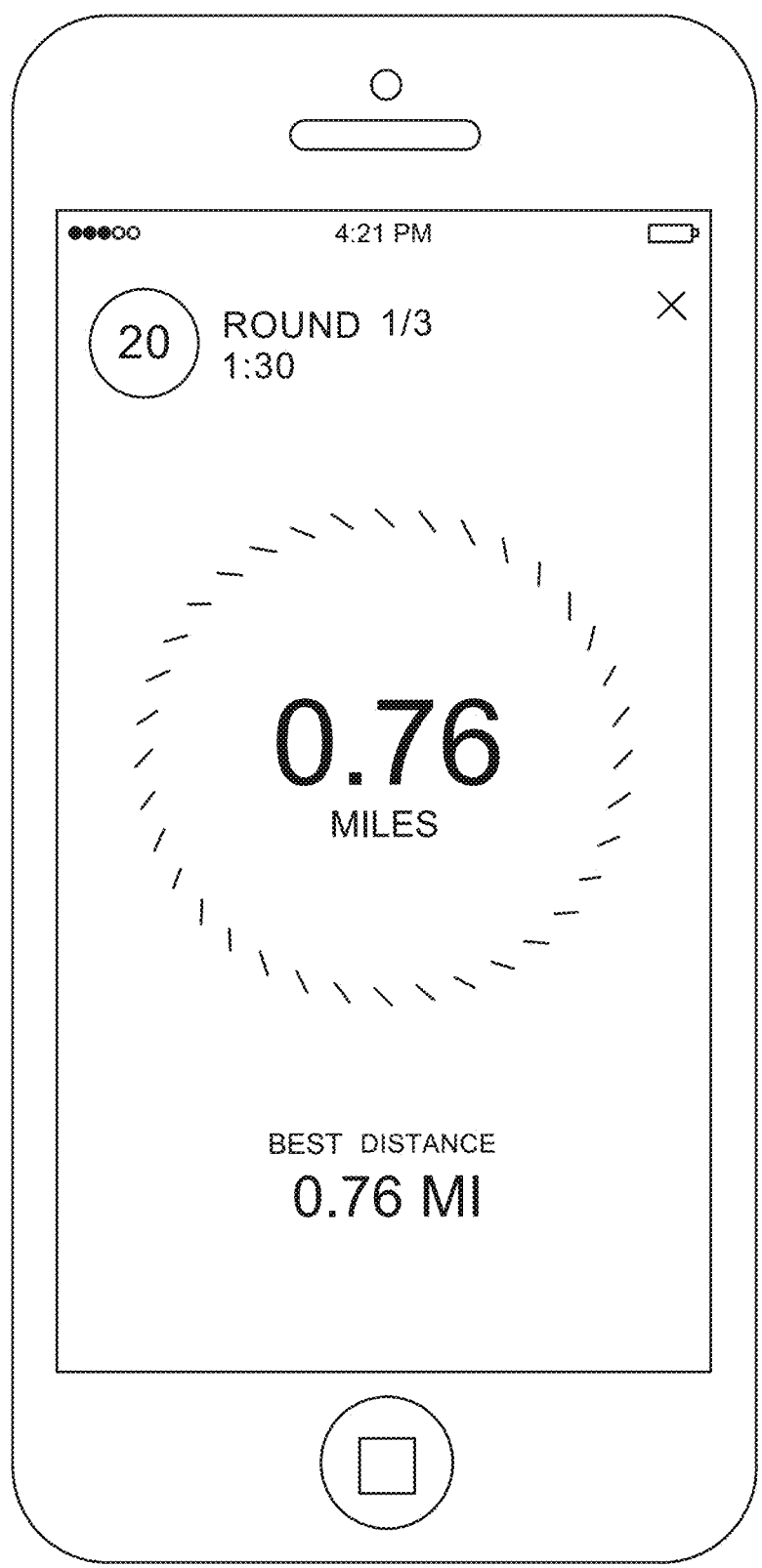

As illustrated in FIG. 10, as the first round proceeds, the circle for each participant begins to rise along a track to indicate a distance measurement. The distance leader may be highlighted. The second screen 124 may display the image of FIG. 75 showing the individual member's power, speed, distance and best distance in a previous round (if a previous round has occurred).

Figure 11:
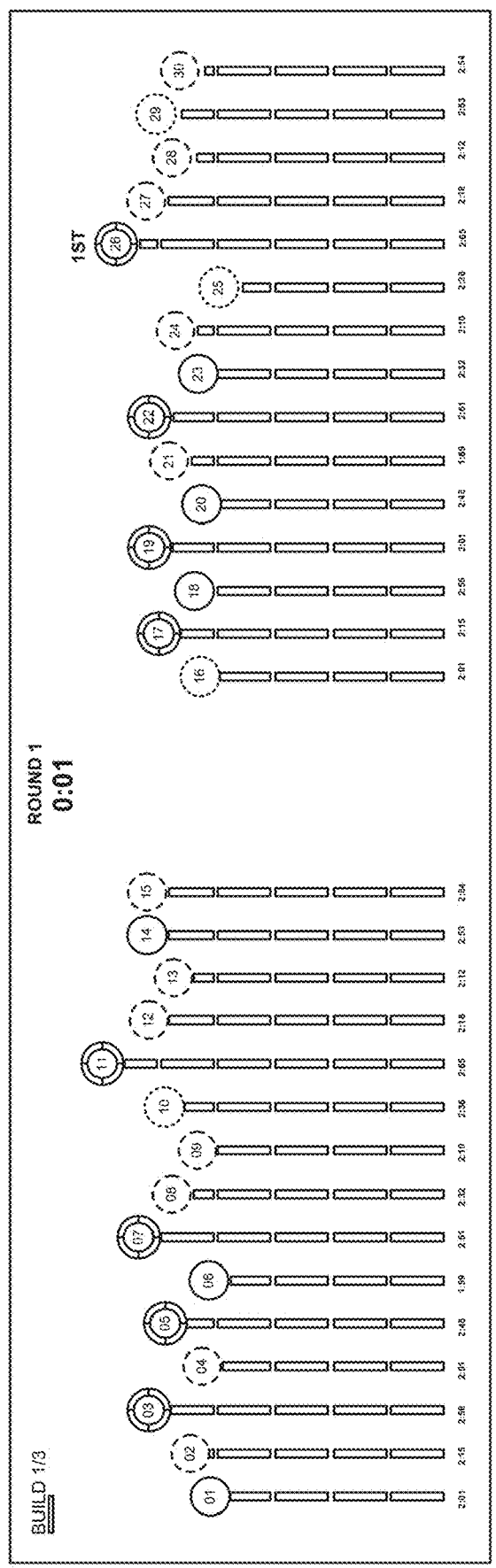

FIG. 11 illustrates nearly the end of the first round. The round leader may be indicated.

Figure 12:
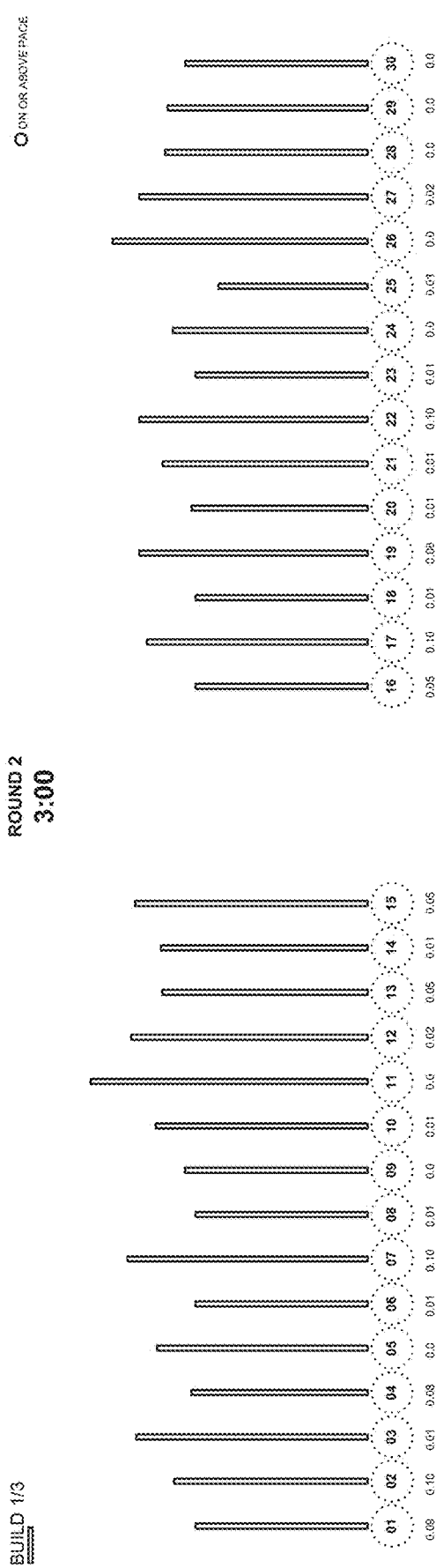

FIG. 12 illustrates the beginning of the second round. The circles of all of the participants may have been returned to near the bottom of the image. However, the track of the circle from the previous round may remain indicating the distance measurement.

Figure 13:
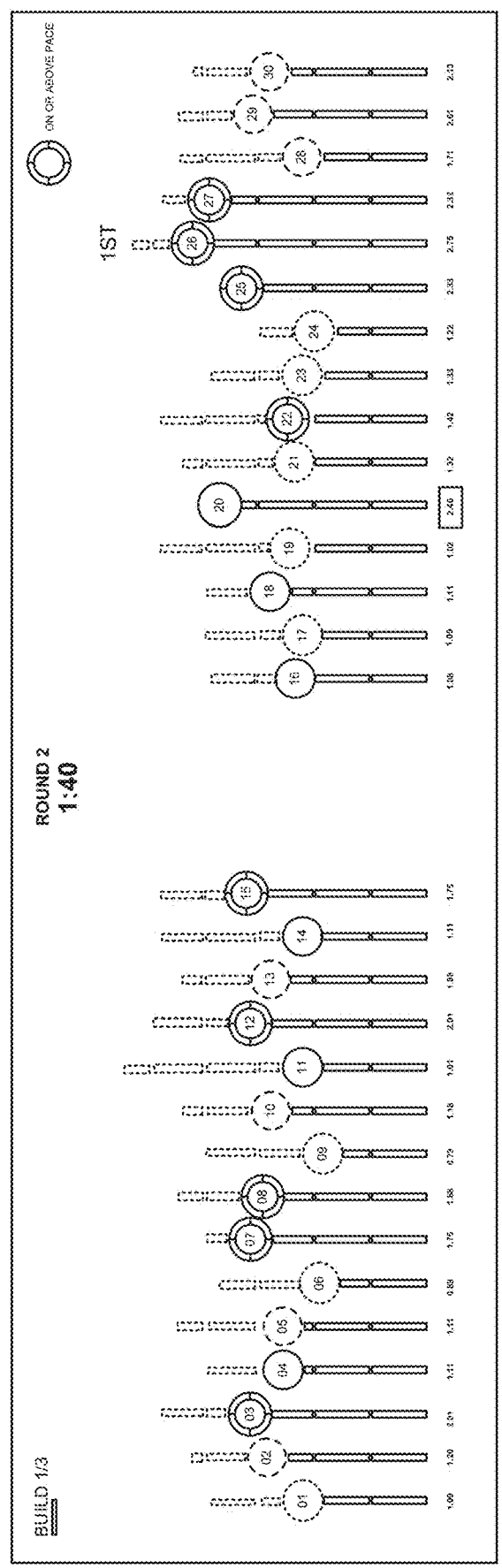
Figure 76:
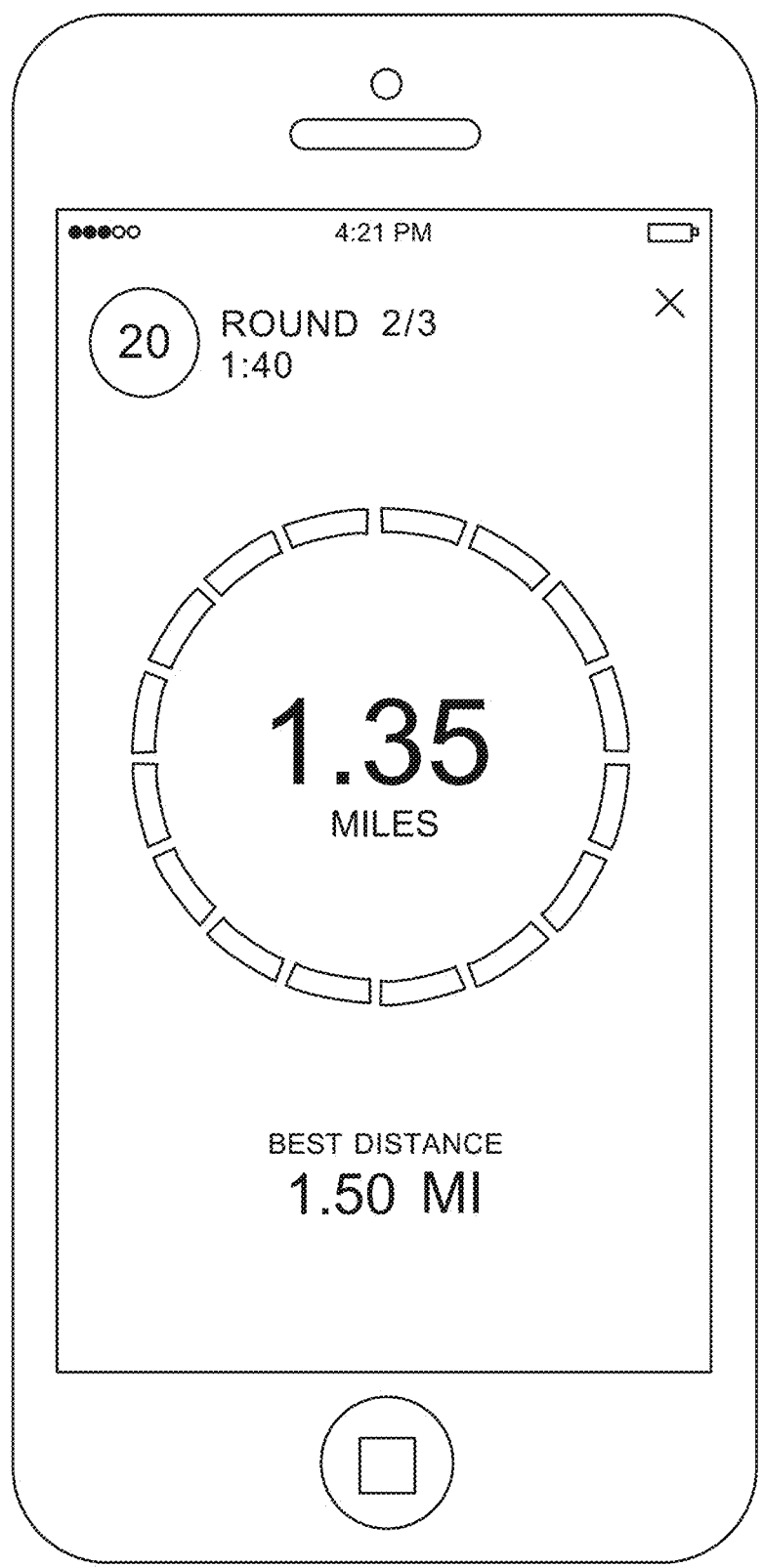

As the second round proceeds, FIG. 13 illustrates that the circle corresponding to each participant may begin to rise along the track corresponding to the distance measurement in the second round. The centers of some of the circles may be highlighted, noting that the participant has a distance measurement at a pace which is at or above the previous round. Once a participant has bested previous rounds, that participant's circle may so indicate, for example by changing color. For example, the participant on bicycle 20 has bested previous rounds. As indicated in FIG. 76, second screen 124 may indicate a pace which is at or above the previous round by showing a highlighted circle.

Figure 14:
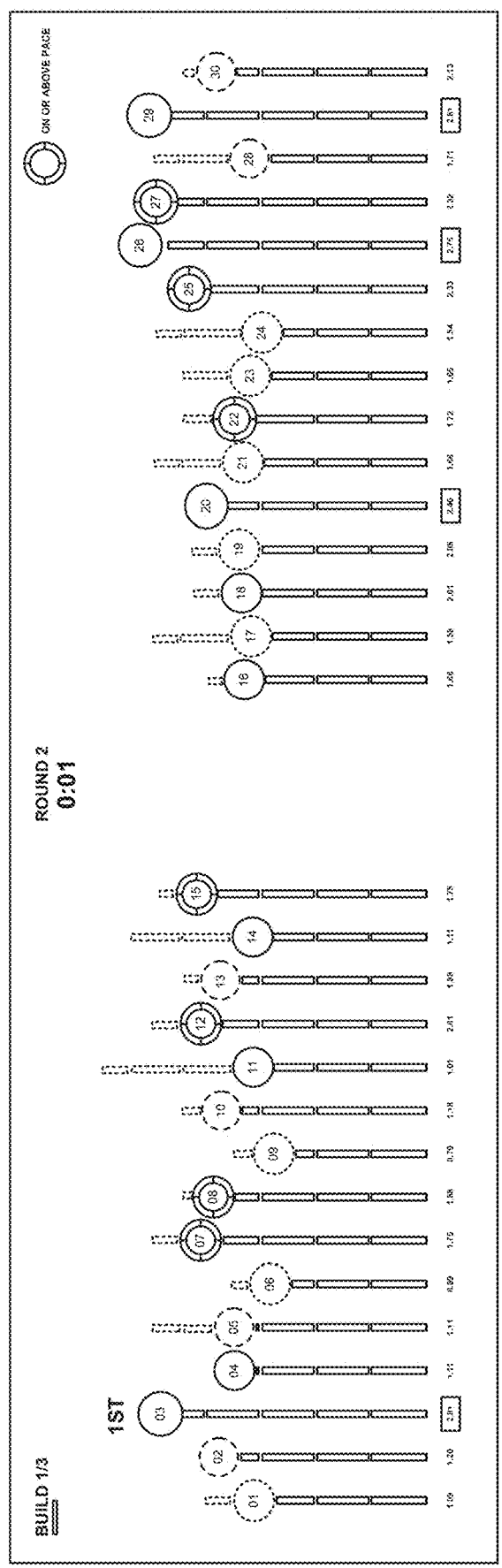
Figure 77:
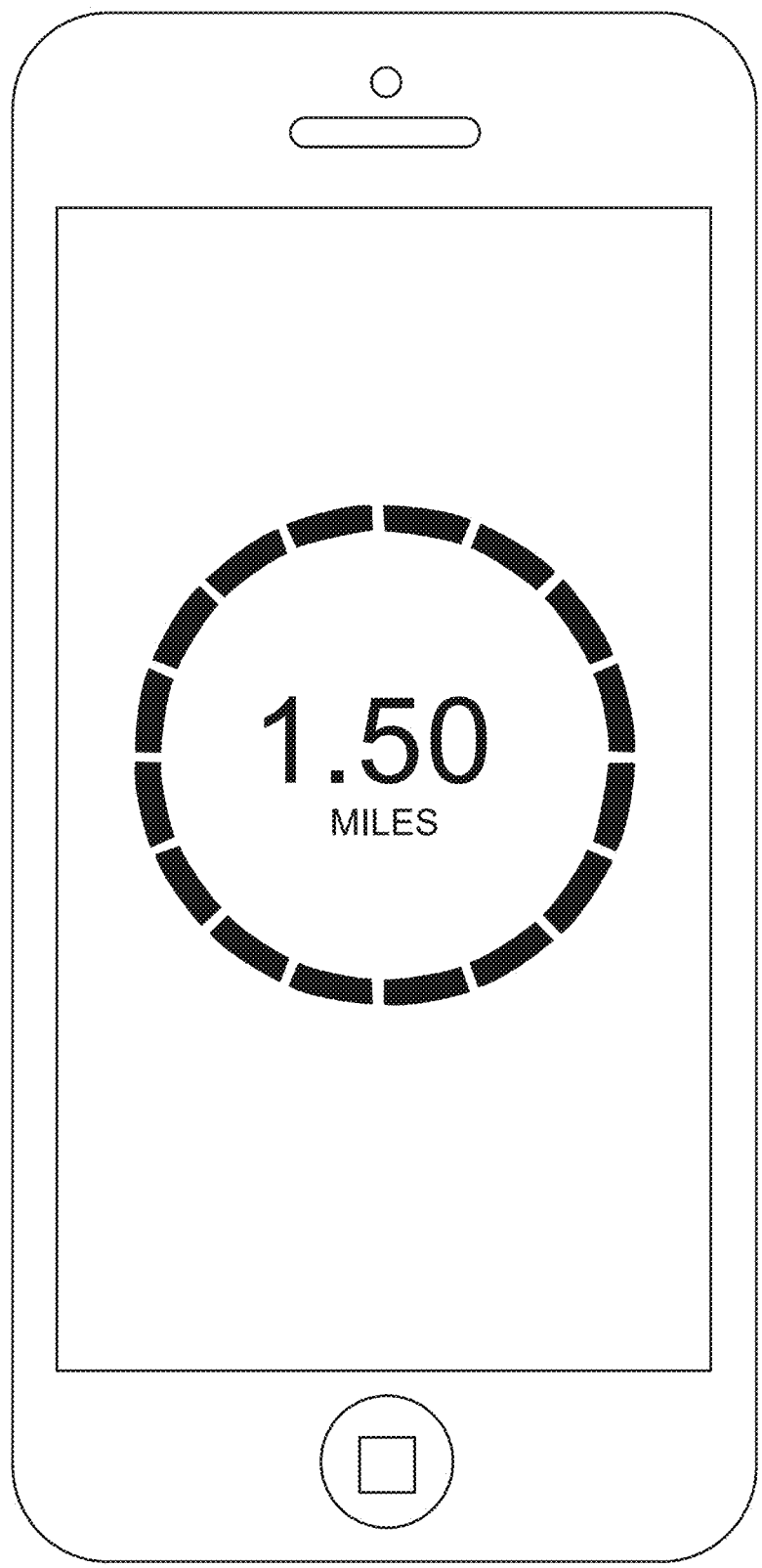
Figure 78:
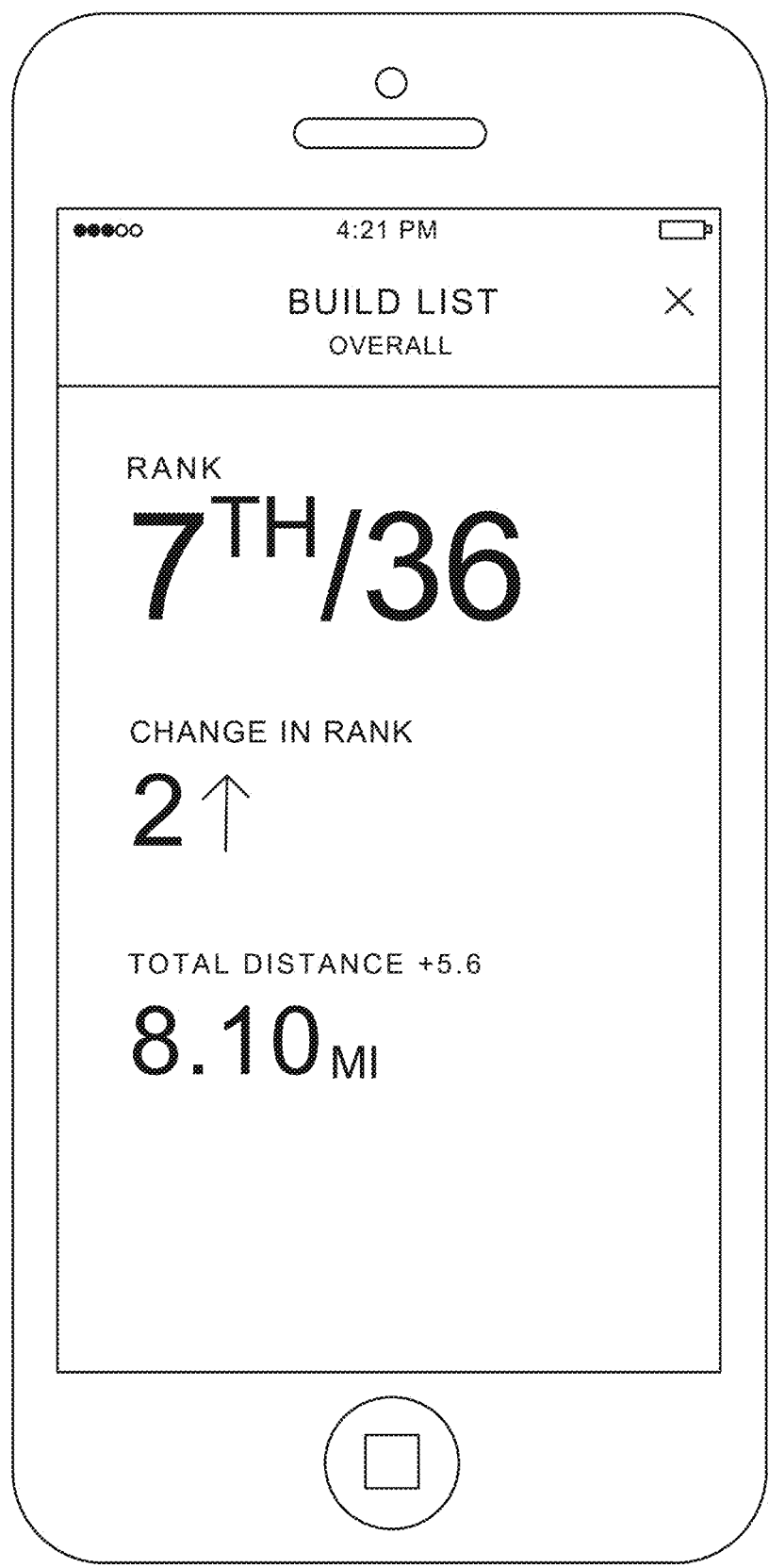

FIG. 14 illustrates nearly the end of the second round. The leader for the second round may be highlighted and the circles of those still on pace to hit the distance from the previous round may be highlighted. As illustrated in FIG. 77, once a member has surpassed their previous best round, second screen 124 may display a momentary celebration.

Figure 15:
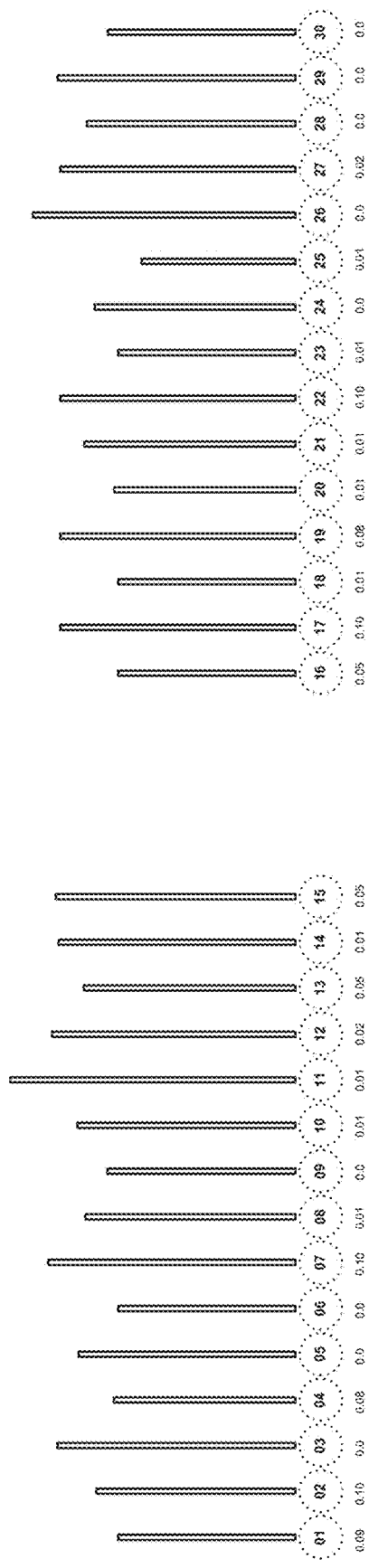

At the beginning on the third round, illustrated in FIG. 15, all circles may be returned to near the bottom of the image.

A track may be indicated having a height corresponding to the best distance performance for each participant in the first or second round.

Figure 16:
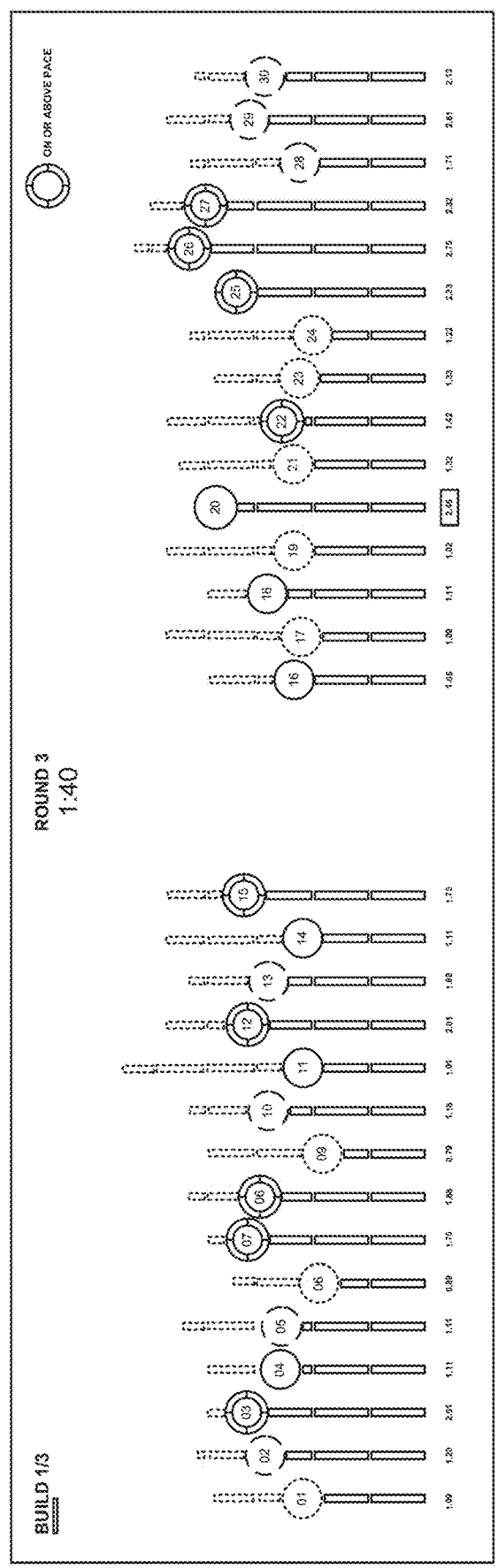

FIG. 16 illustrates the middle of the third round. As with the previous round, the leader for the round may be indicated. Also, the circles of those on track to surpass their previous best round may be highlighted.

Figure 17:
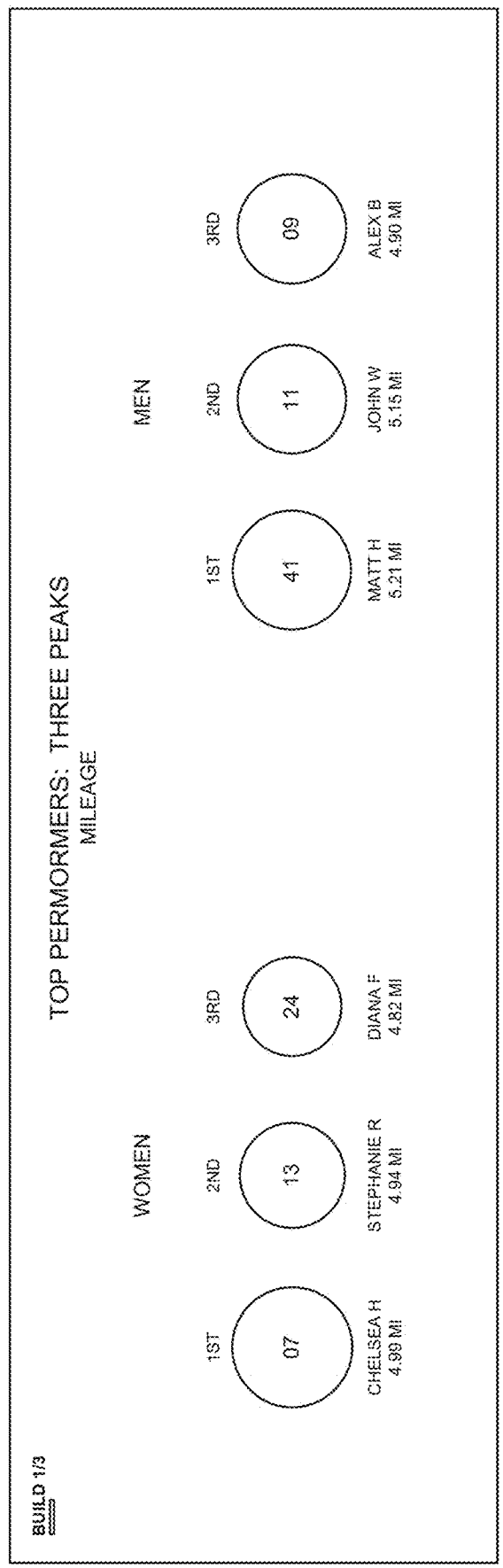
Figure 18:
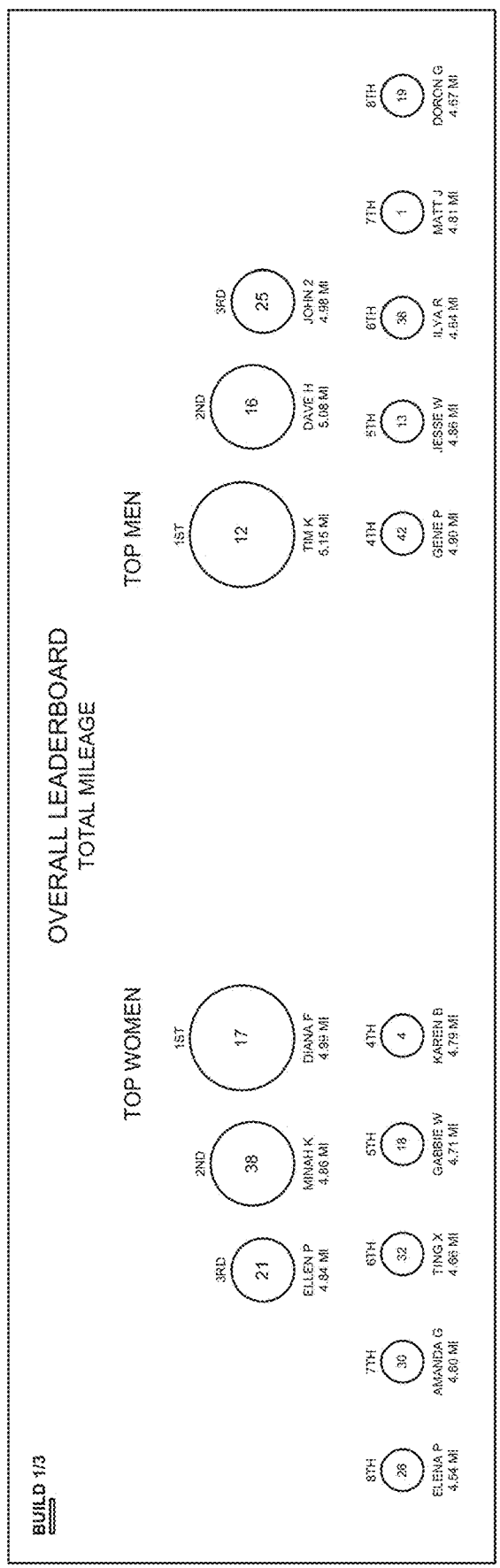
Figure 28:
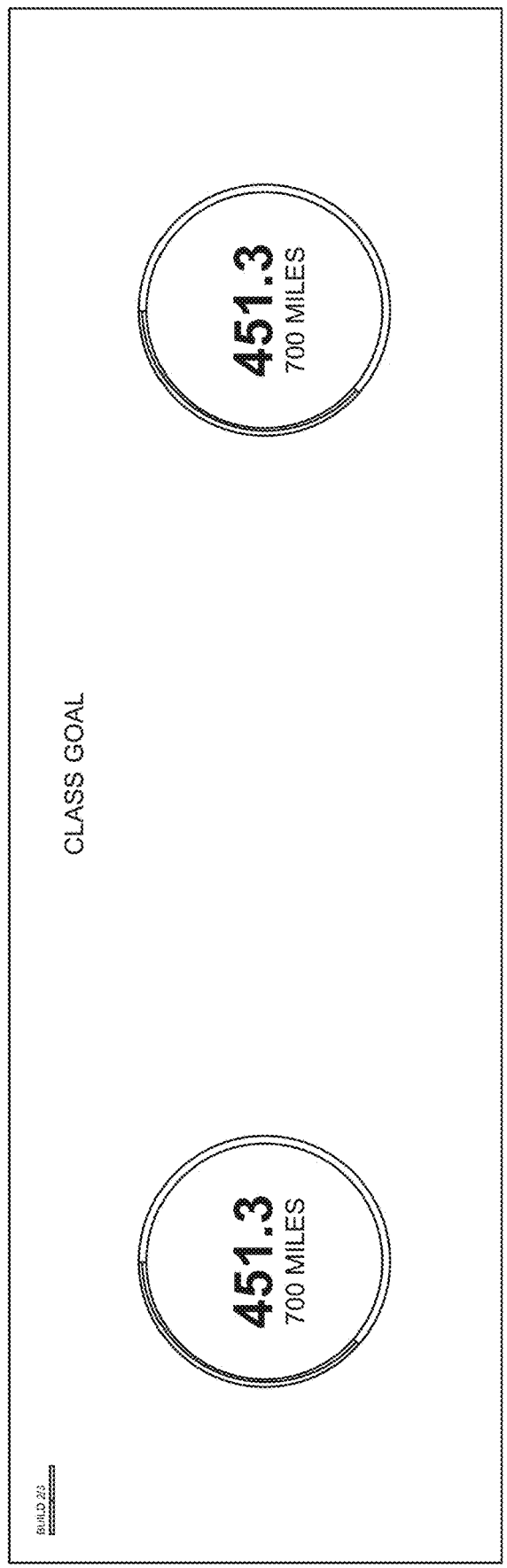
Figure 79:
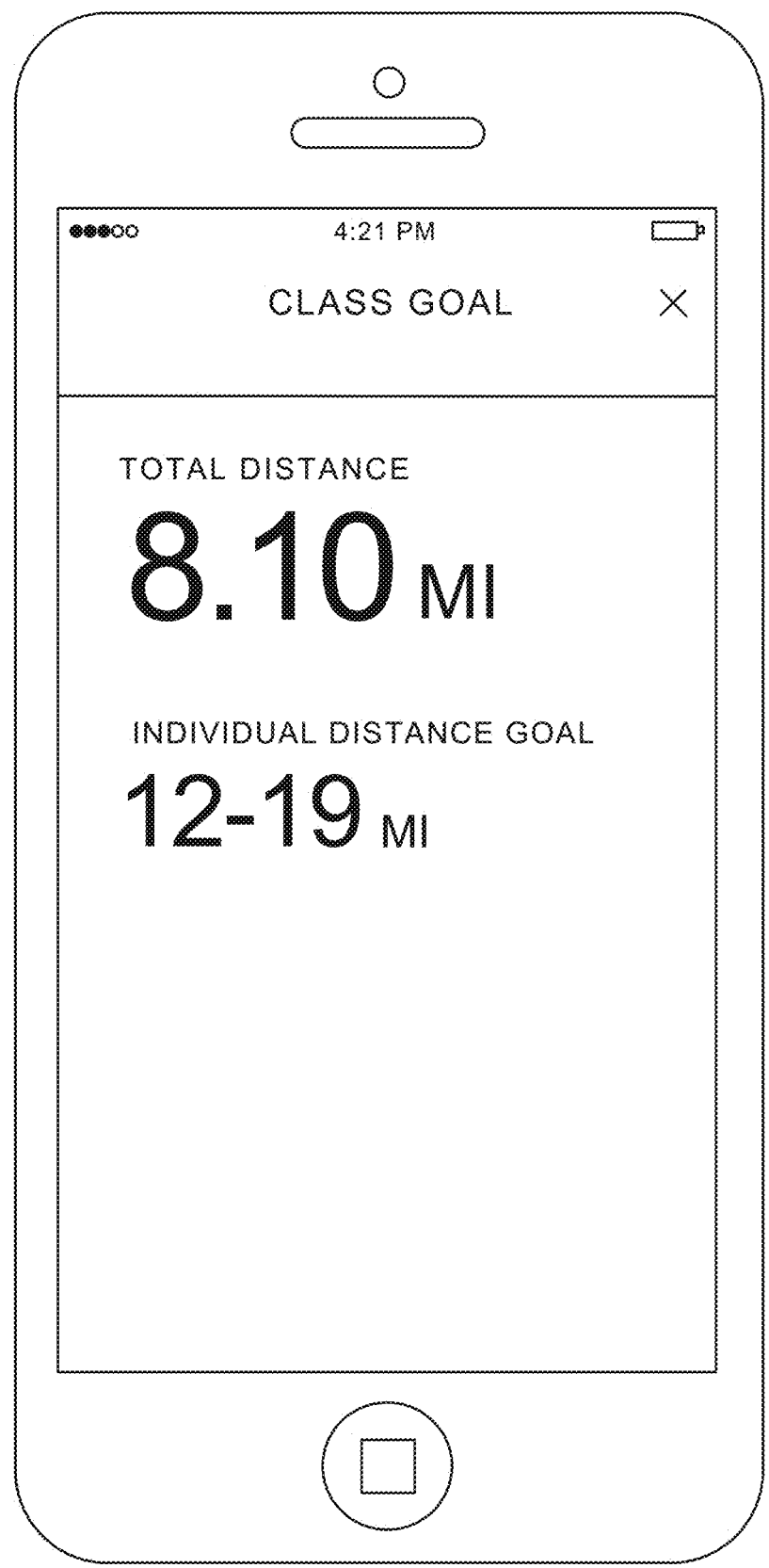

At the end of the third round, FIG. 17 illustrates an image that may display the top performers (optionally distinguishing top male and female participants) for the three-peaks game. The performances indicated may represent the sum of the three rounds making up the three-peaks game. FIG. 18 illustrates an overall leader board that may be displayed after the three-peaks game. At the same time, second screen 124 may display an image such as FIG. 78 which shows the individual member's ranking, the change in ranking since the previous round and the total distance traveled in the training session, including the addition to the total since the last time this screen was displayed. Thus, second screen 124 displays data comparing the individual member to the overall class. The leader board may represent overall class distance performance including the warm-up. An image, similar to FIG. 28, showing performance toward the class goal may also be displayed. At the same time, second screen 124 may display FIG. 79 showing the individual member's contribution to the class goal and the member's individual goal. Afterwards, an animation may be presented, similar to FIG. 7, dynamically driven by class performance, until the instructor triggers the second stage.

Figure 19:

FIG. 19 may provide a representation of the second stage named "avalanche." This stage may be a 10-minute stage. For this game, the class may be dynamically divided into two teams based on the number of riders in the room and the placement of the bicycles within the room. Each participant may be represented by a circle as in the first game, wherein the thickness of the line forming the circle corresponds to power. Each time a rider covers 0.25 miles or the like, a circle icon with that participant's bicycle number may drop down to the mountain corresponding to that participant's team. The thickness of the dropping circle indicates power at the time the rider covered the 0.25 miles. Each time that participant covers 0.25 miles or the like, another circle with that participant's bicycle number may drop onto the mountain corresponding to that participant's team.

Figure 20:
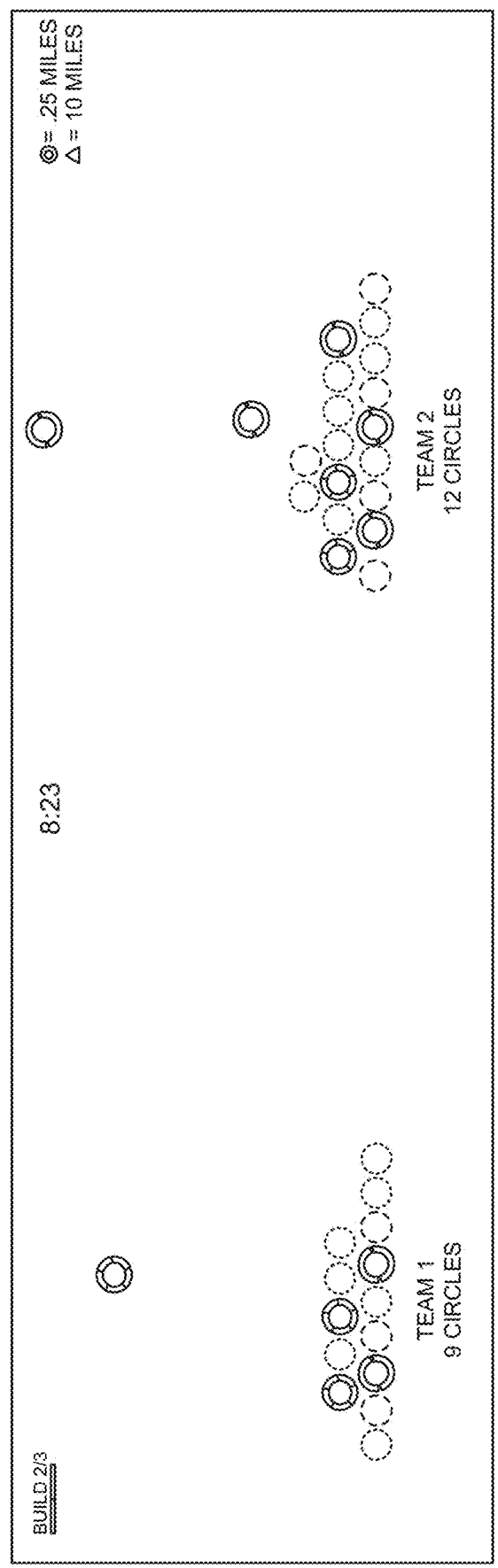

FIG. 20 illustrates an image from display 116 as both teams begin to collect circles to form their respective mountains. The idea of this game may be to form as many mountains as possible within the 10-minute period of the game.

Second screen 124 may display individually oriented images as in the previous stage for this and subsequent stages as well as the second training protocol.

Figure 21:
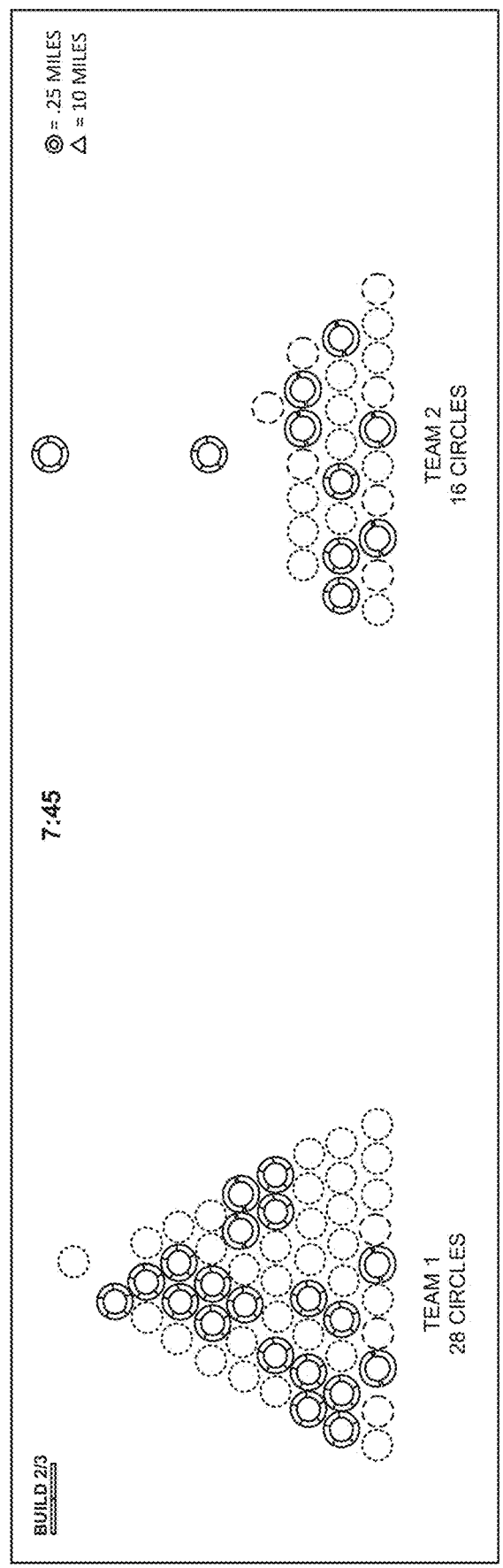
Figure 22:
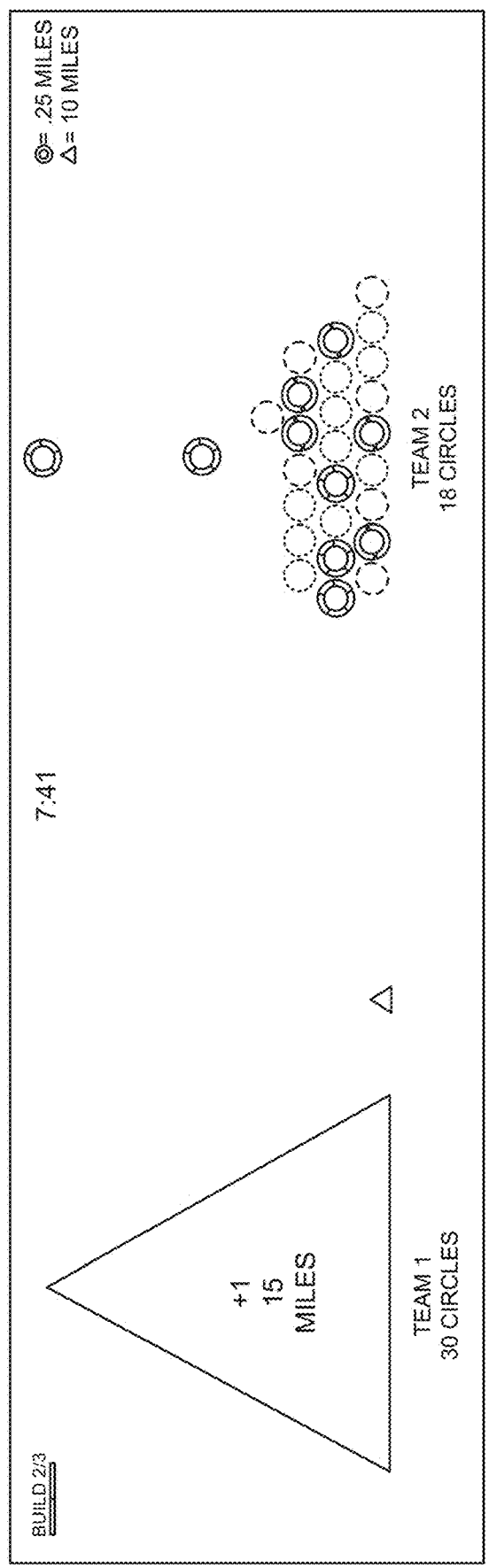
Figure 23:
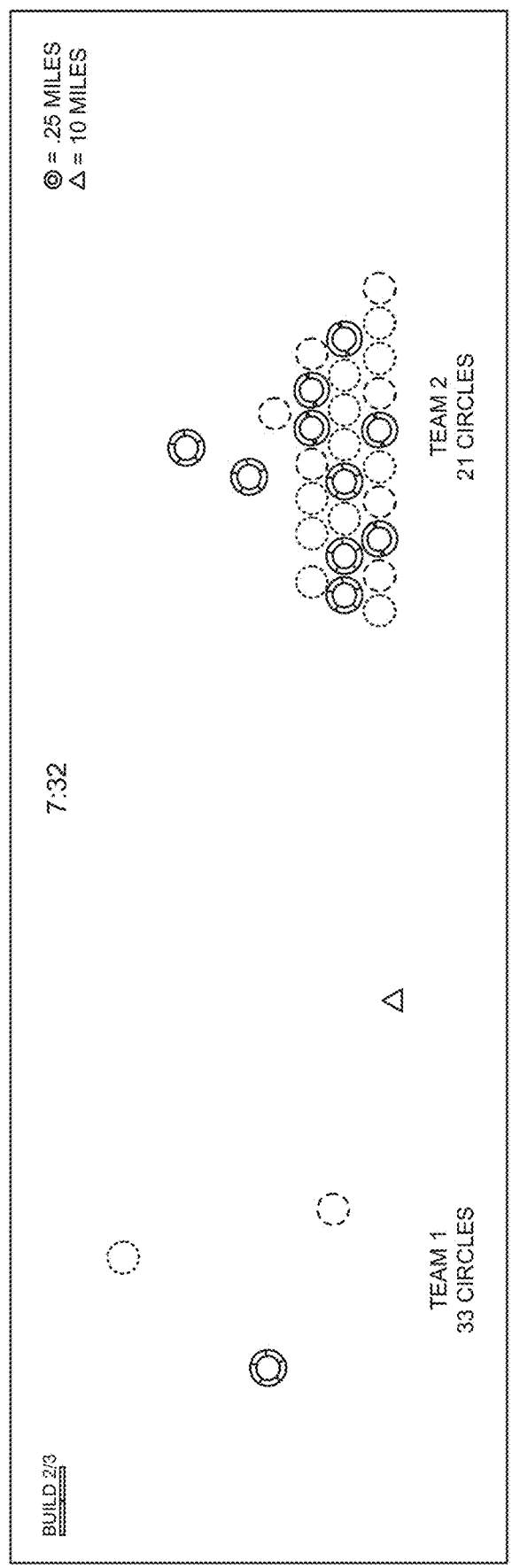

FIG. 21 illustrates an image in which Team 1 may be about to complete its first mountain. As illustrated in FIG. 22, when a team completes a mountain, then a display celebrating the completion may appear on display device 116. The team distance needed to complete a mountain may vary depending on class size. The size of the circles may vary, depending on class size, to accomplish this. As illustrated in FIG. 23, completion of the first mountain by Team 1 may be represented by a smaller triangle. Team 1 then may begin to build its second mountain.

Figure 24:
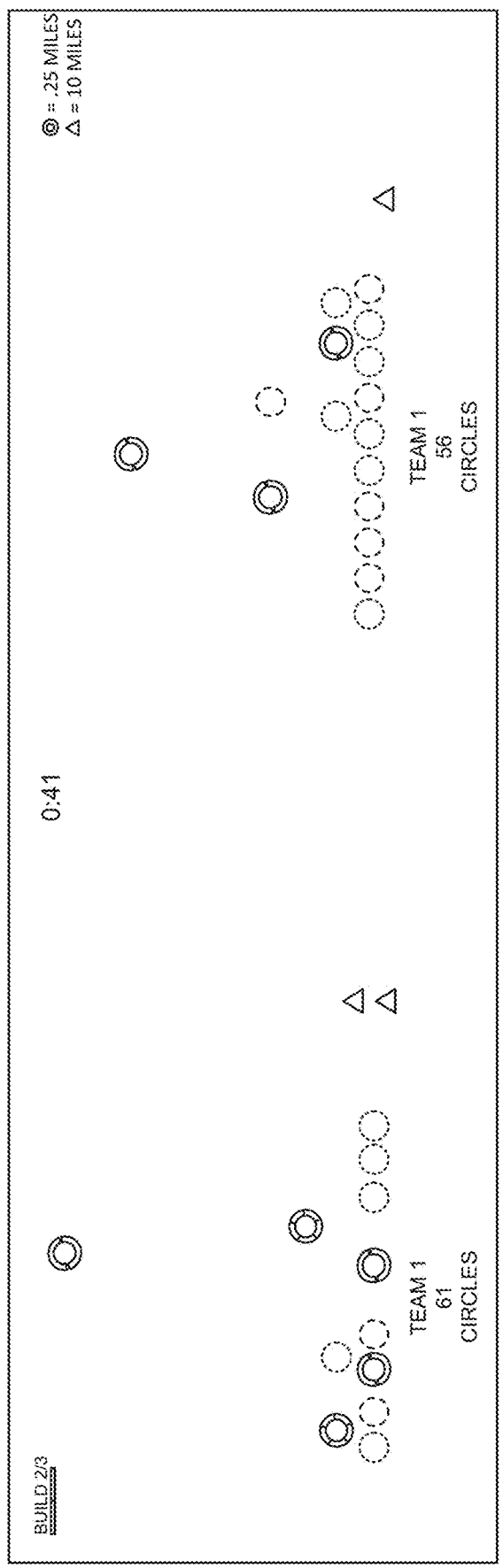

As illustrated in FIG. 24, each time a team completed a mountain, the mountain may be replaced with a triangular counter and the team may continue to build its next mountain. In this game, as with any of the other games, in view of the intensity of this game, an instructor controlling the game may cause the image displayed on display device 116 to change to an animation which may have an image which may be responsive to the collective performance of participants in the class. This may also be the case with the "summit push" "tour de force" games described with respect to FIGS. 29-32 and 60-66 below.

Figure 25:
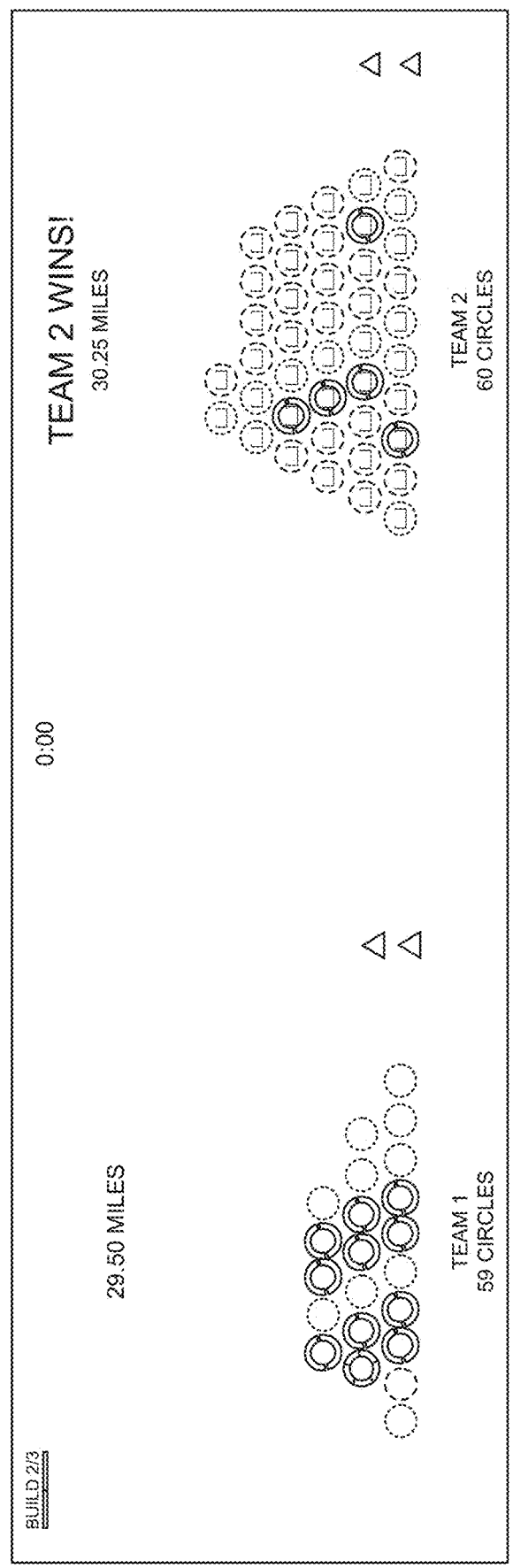

At the end of the game, as illustrated in FIG. 25, the team having the largest distance measurement may be declared the winner. This game may provide both individual and team measurements. The number of circles that an individual participant contributes to each mountain remains may be visible. At the same time, the number of mountains built by each team may also be indicated.

Figure 26:
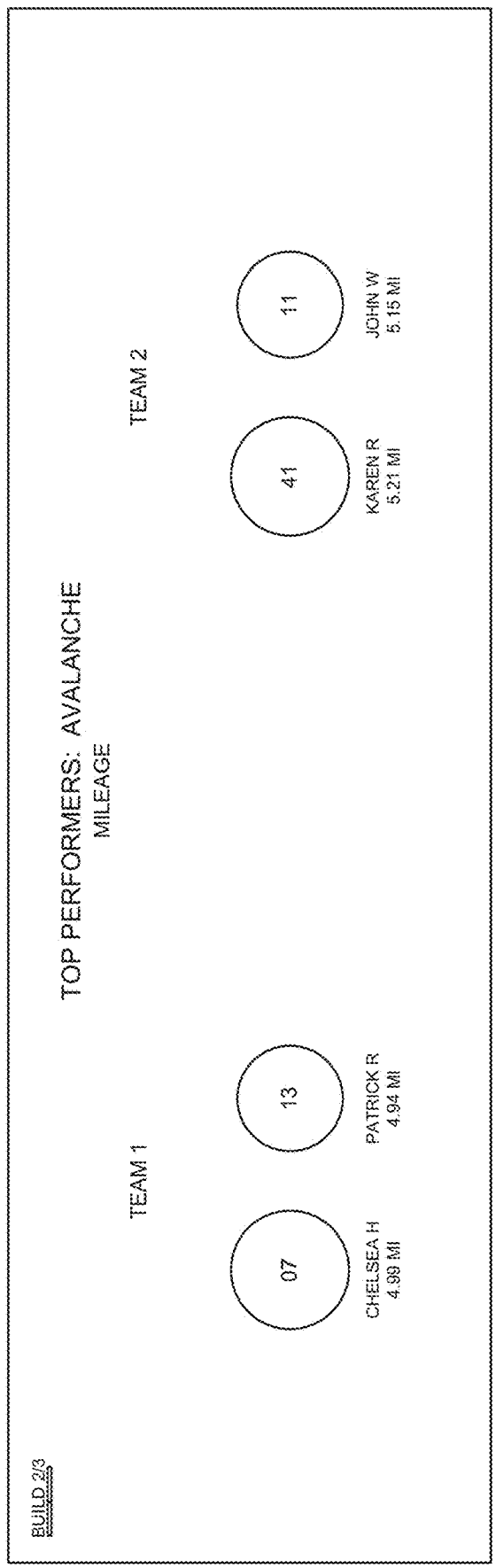
Figure 27:
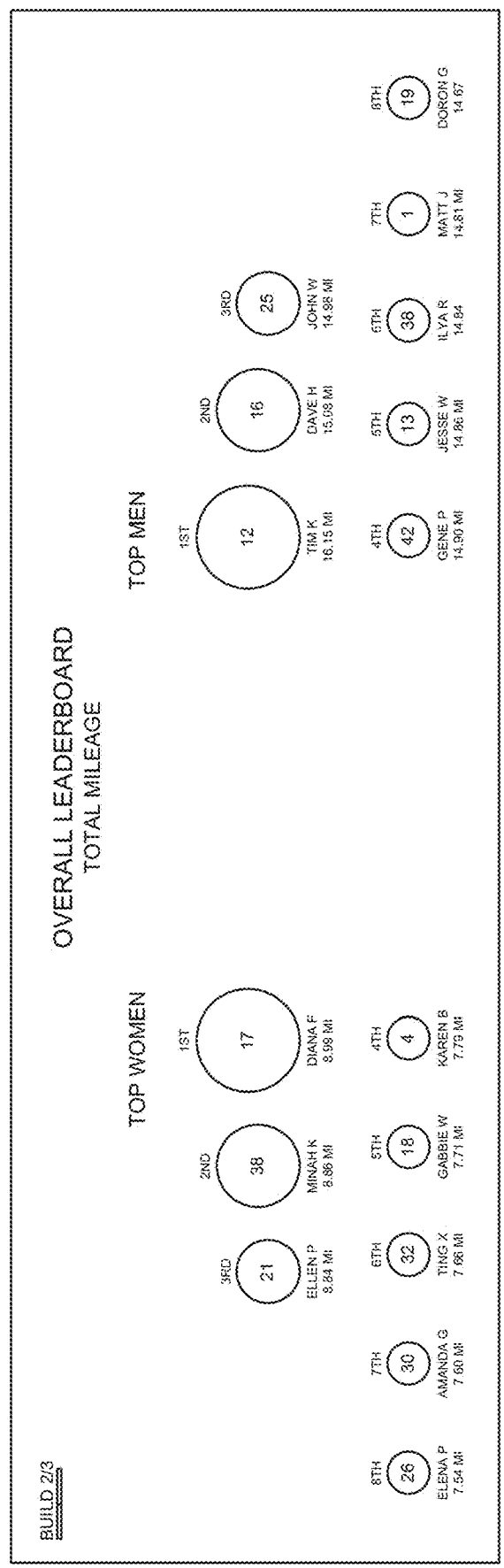

As illustrated in FIG. 26, after the second game, top male and female performers for each team may be celebrated. Also, as illustrated in FIG. 27, the overall leader board may also be displayed showing mileage leaders accumulated over the entire class. FIG. 28 illustrates that distance performance toward a class goal may also be indicated. Afterwards, an animation may be presented similar to FIG. 7.

Figure 29:
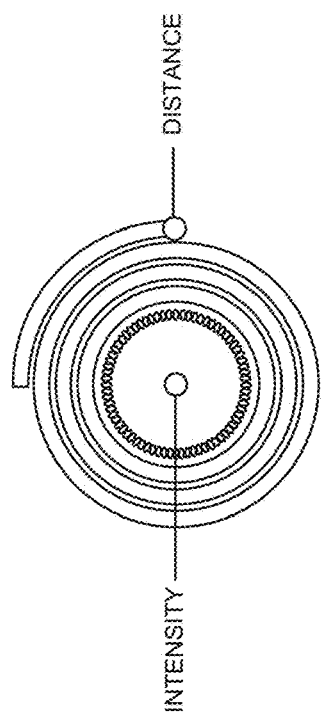
Figure 30:
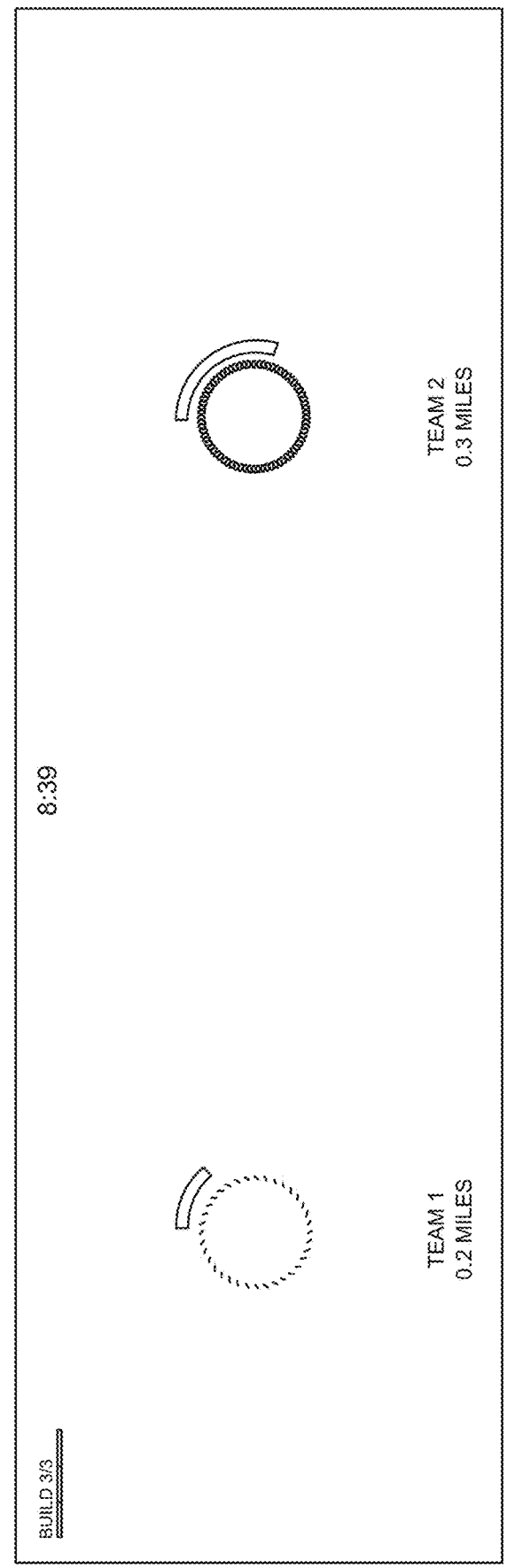

FIG. 29 represents the third stage of the class named "summit push." This is a game in which data may be graphically represented only for each of two teams, and not for the individual. The game may extend for ten minutes, for example. As with the previous game, the class may be dynamically divided into two teams based upon the number of participants in the room and the placement of bicycles within the room. As illustrated in FIG. 30, as the game begins, each team may have a rotating circle. The rate of rotation of the circle may correspond to the average rotational speed of the team, and the thickness of the line forming the circle may be representative of the average power of participants on that team. A band may surround the circle and may gradually progress around the circle. The band may represent the average distance measurement of participants on each team.

As illustrated in FIG. 31, each time a band is completed, a congratulatory animation may be displayed. The team then may begin to build its next ring around the circle.

FIG. 32 illustrates the end of the third stage. As illustrated, Team 1 is the winner because it has the greatest average distance as indicated by the rings around its circle. Each ring may represent a fixed distance measurement, such as 0.5 miles.

As with the previous games, after the third game is completed, top performers for the third game may be displayed and the overall leader board for the entire class may be displayed. An animation may also be presented which illustrates whether or not the class collectively made its class goal announced at the beginning of the class. Text may also be included that is driven by the relationship of class performance to class goal. Afterwards, an animation may display, similar to FIG. 7, for a cool down period.

Figure 60:
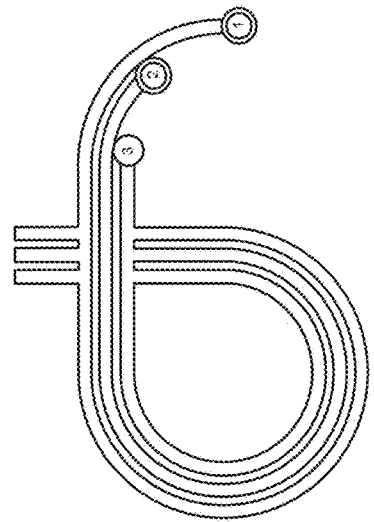
FIGS. 60-66 illustrate a game for an exercise system according to an embodiment of the invention.
Figure 61:
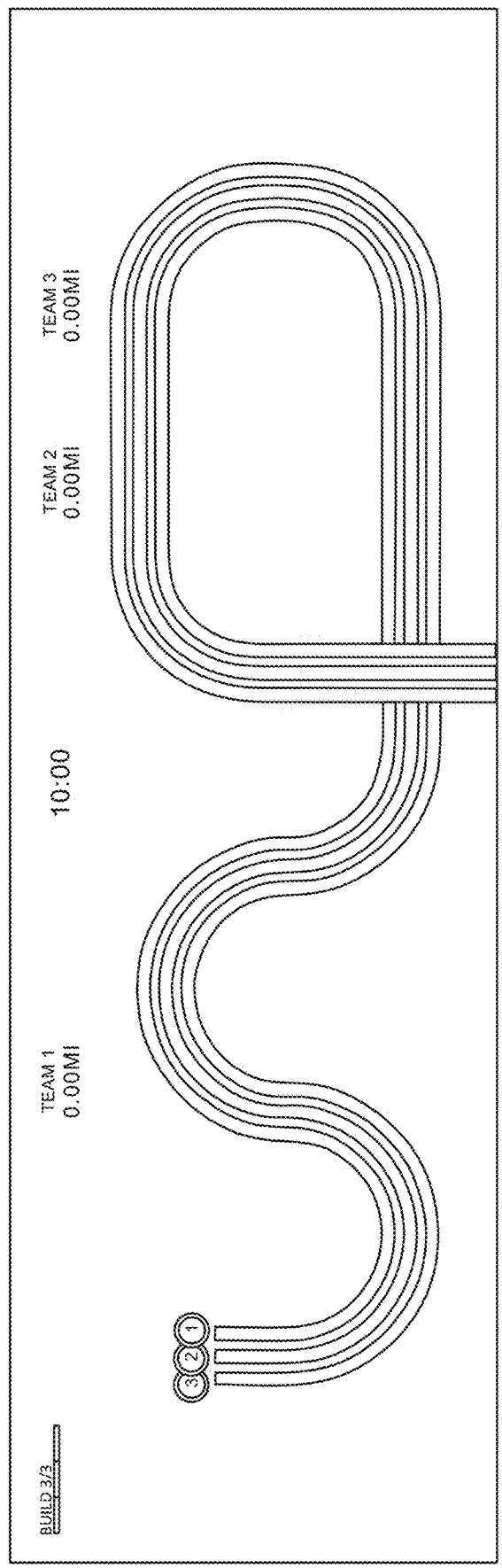

As an alternative for the third stage, a game called "tour de force" may be played as illustrated in FIGS. 60-66. This is a game in which data may be graphically represented only for each of three, or any other number of, teams, and not for the individual. The game may extend for 10 minutes, for example. The class may be dynamically divided into three teams based on the number of participants in the room and the placement of bicycles within the room. As illustrated in FIG. 60, this game involves each team following along a course where progress along the course is indicated based on a team's average distance. FIG. 61 shows the three teams at the beginning of the game. As with previous illustrations, the speed of rotation of each team's circle represents the average rotational rate of each team and the thickness of the circle represents the average power being generated by each team.

Figure 62:
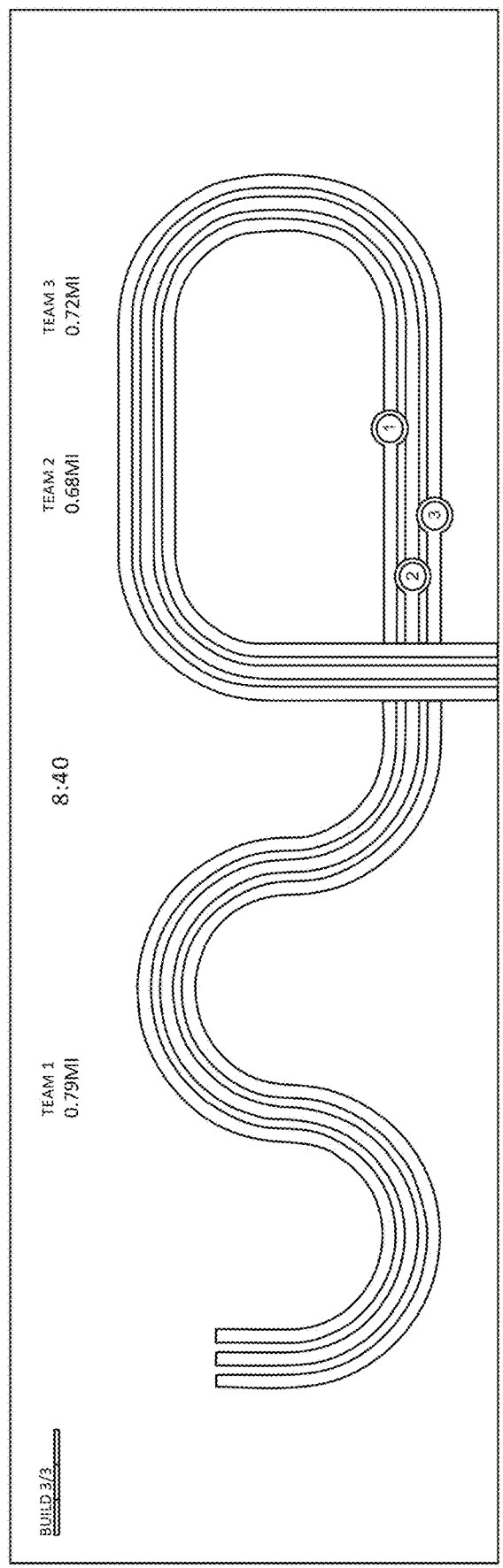
Figure 63:
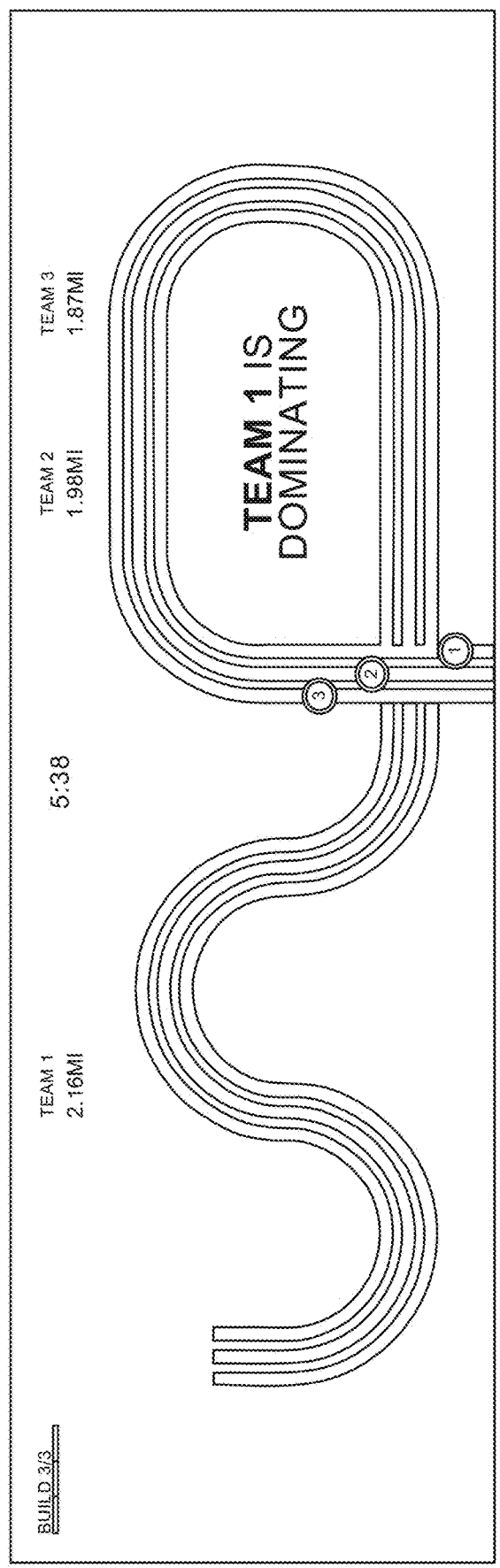
Figure 64:
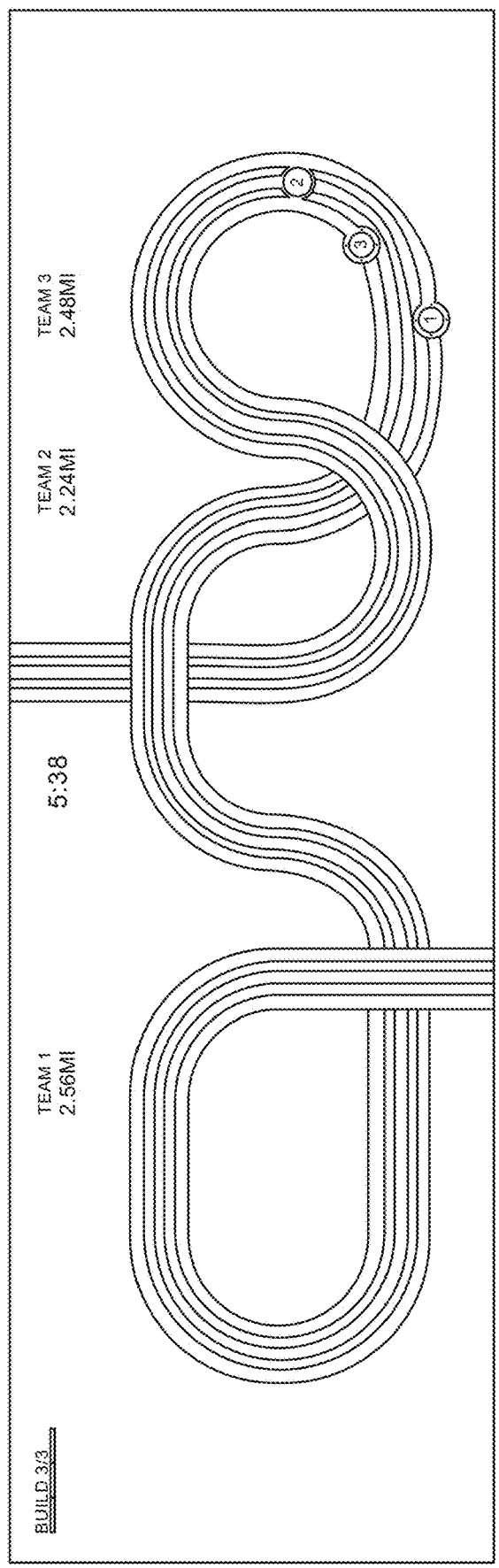

FIG. 62 illustrates that team 1 has covered the greater distance. Once a team's average distance covers a fixed distance, such as a mile, the accomplishment of that team may be celebrated by changing the image, such as the color of the display. As illustrated in FIG. 63, as the teams approach the end of the track on a screen, the screen may indicate the leading team and then slowly pan to show the next segment of track as illustrated in FIG. 64. The scale of each track may be adjusted so that all teams remain on the same screen.

This process may continue each time the teams cover all of the track on a screen for the 10 minutes that the game is in progress. The distance that the tracks cover is based on how far the slowest team will cover in the 10 minutes.

Figure 65:
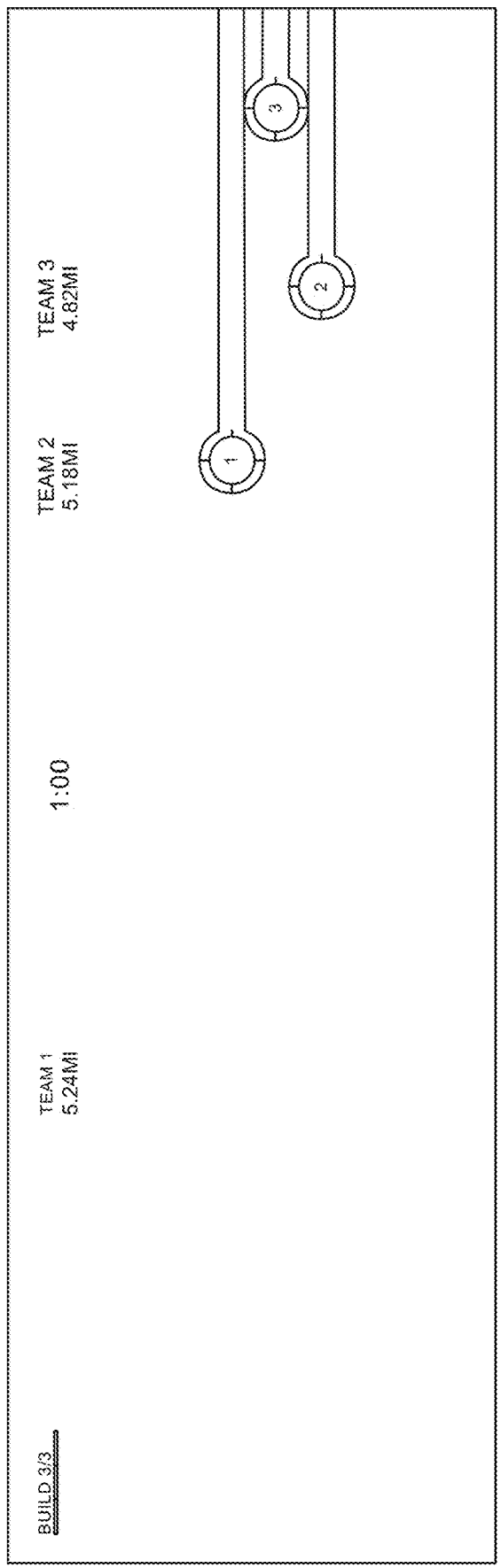
Figure 66:
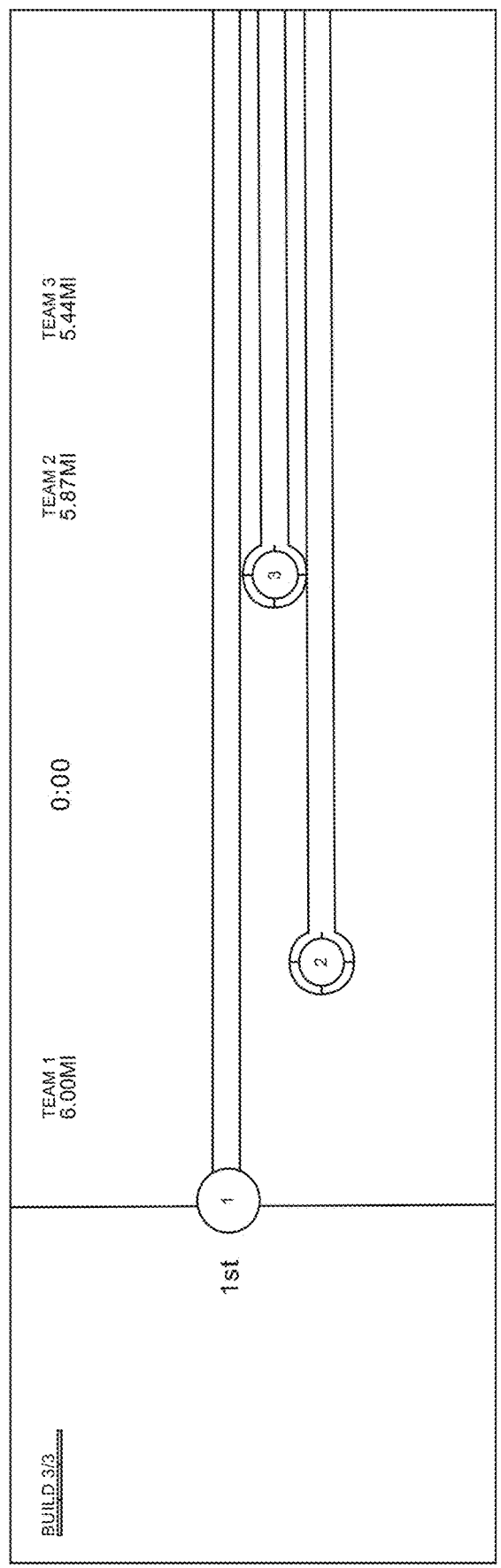

For the last fixed period of time, such as, for example, 30 seconds, the screen changes to the home stretch as illustrated in FIG. 64. The slowest team will be displayed on the right side of the display with faster teams further advanced to the left. At the end of the 10 minutes allotted for the game, the team covering the most distance is declared the winner as illustrated in FIG. 65. Subsequently, a leaderboard may be displayed as in previous games, illustrating the top male and female participants for each team. As described previously, if a team consists only of males or females, the top two performers may be indicated on the leaderboard. Class progress to the class goal may also be illustrated.

As noted above, the class of the second training protocol may focus on optimizing caloric expenditure and performance. This class may include 5 stages of 4-6 minutes in length. Each stage may have a different high intensity interval training protocol with 2 minutes of recovery between each stage. The first stage may provide an animation representing individual performance. The third stage may provide an animation of performance based on partners. The fifth stage may provide an animation of performance based only on a team. The second and fourth stages may not have games, providing an instructor more flexibility in coaching these segments. During these segments, an abstract animation may be provided which is responsive to the exercise signals from the participants of the class.

Figure 33:
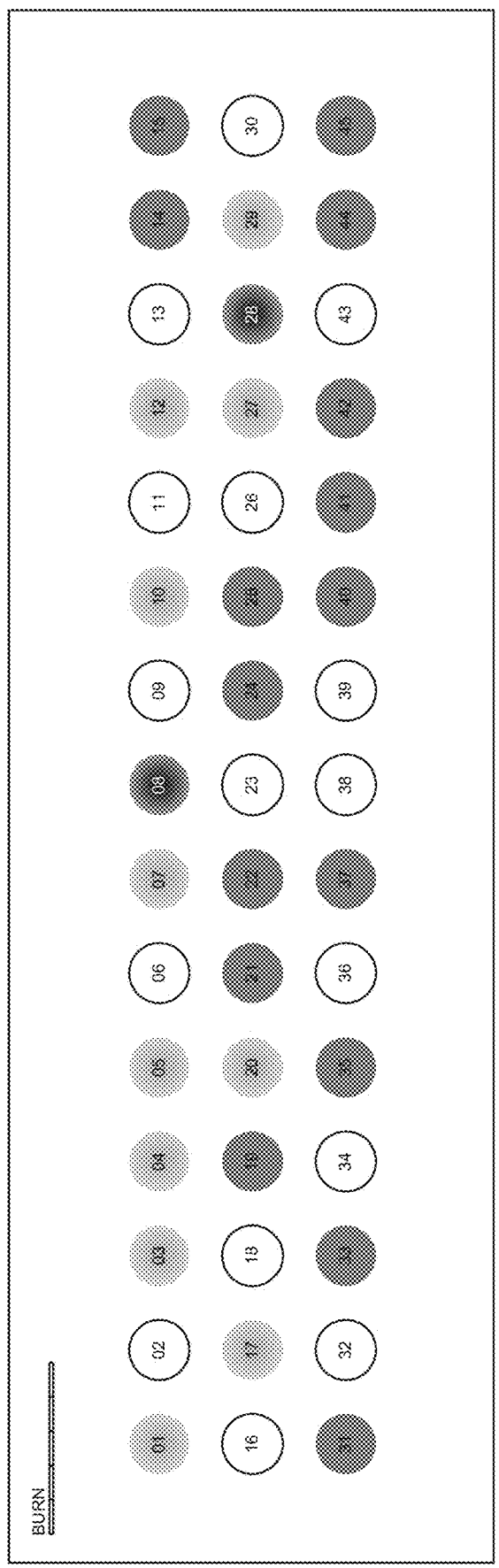

FIG. 33 shows an image on display device 116 generated by the output signal from web application module 112 before class begins. Each bicycle in the class may be represented as a circle. The circle may also or alternatively rotate in relation to rate of rotation. As a participant's power increases, that participant's circle may become brighter and fill in. As noted above, a participant's ability to generate power is dependent upon the participant's weight. That is, it is much easier for a participant weighing 250*lbs*. to generate higher watts than a participant weighing 120*lbs*. As a result, the power required to light up each circle may vary for men and women, using gender as a proxy for weight.

Figure 34:
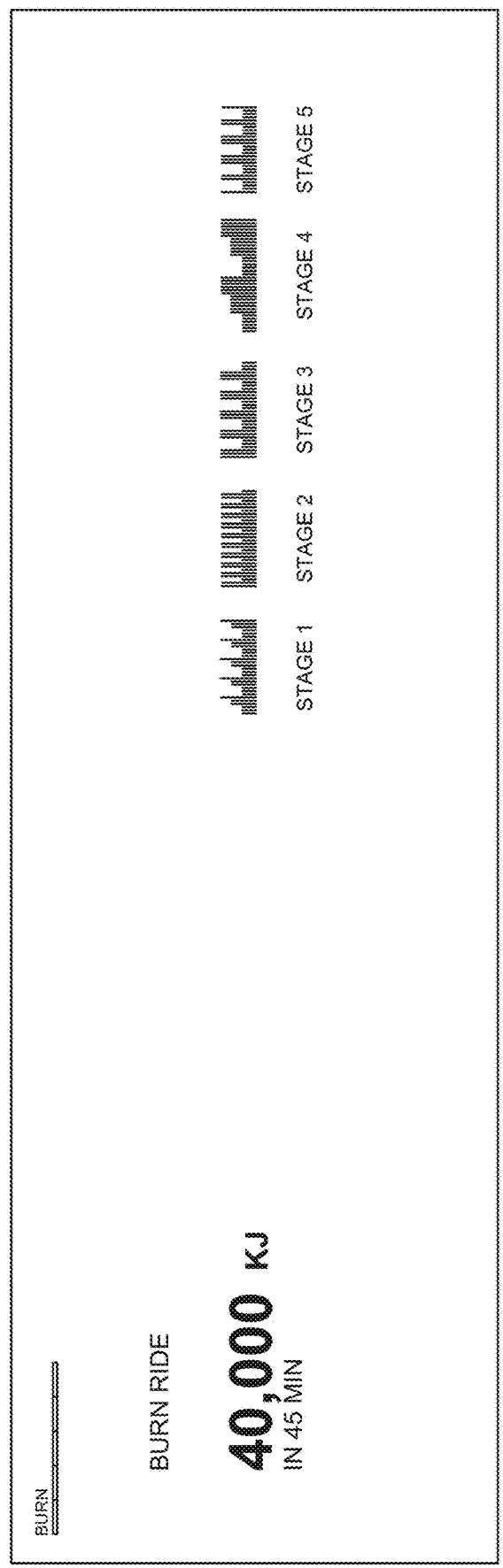

As illustrated in FIG. 34, as the class begins, an overview of the class may be provided. The left side of the image on display device 116 may indicate the overall class objective, such as burning 40,000 kilojoules in 45 minutes. This may be adjusted dynamically based on the number of riders in the class (e.g., 400 kilojoules per rider). The right portion of the display may graphically illustrate the stages that will make up the class. As noted above, the class of the second training protocol may include 5 stages, separated by recovery periods.

Figure 35:
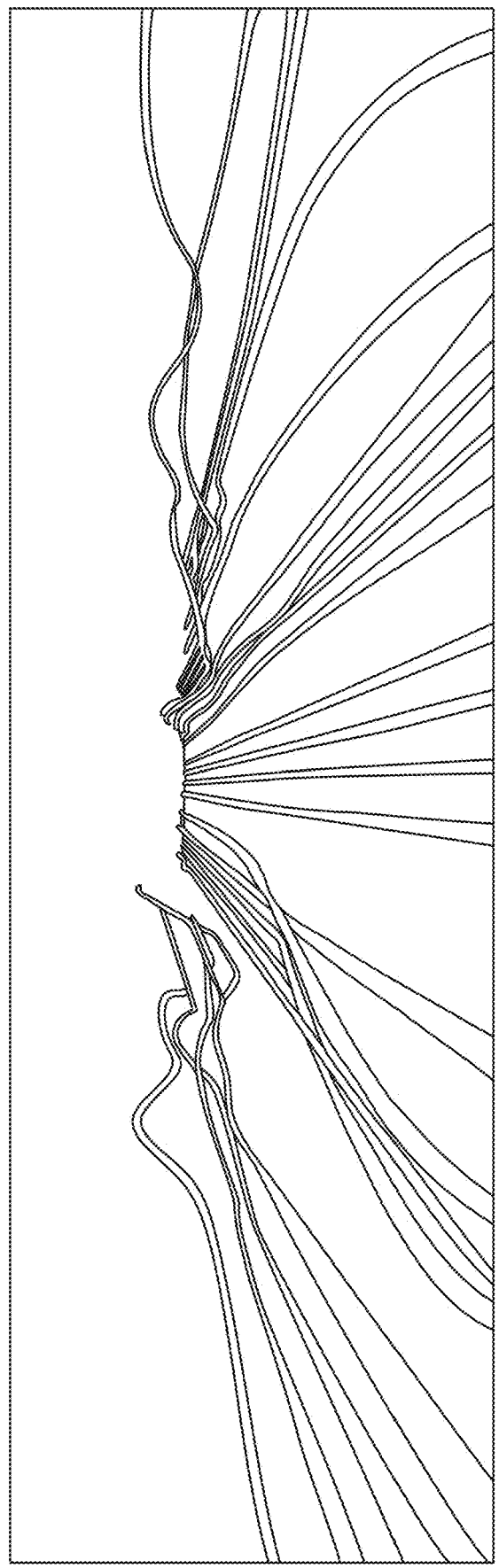

FIG. 35 illustrates an animation corresponding to an output signal from web application module 112, which may be displayed on display device 116 during a warm-up period prior to the first stage. The abstract animation may be responsive to the exercise signals from the class. For example, the animation may include a number of wavy lines made up of particles. As the power generated by participants increases, the lines may increase in brightness and the movement of particles making up the lines may increase in speed.

Figure 36:
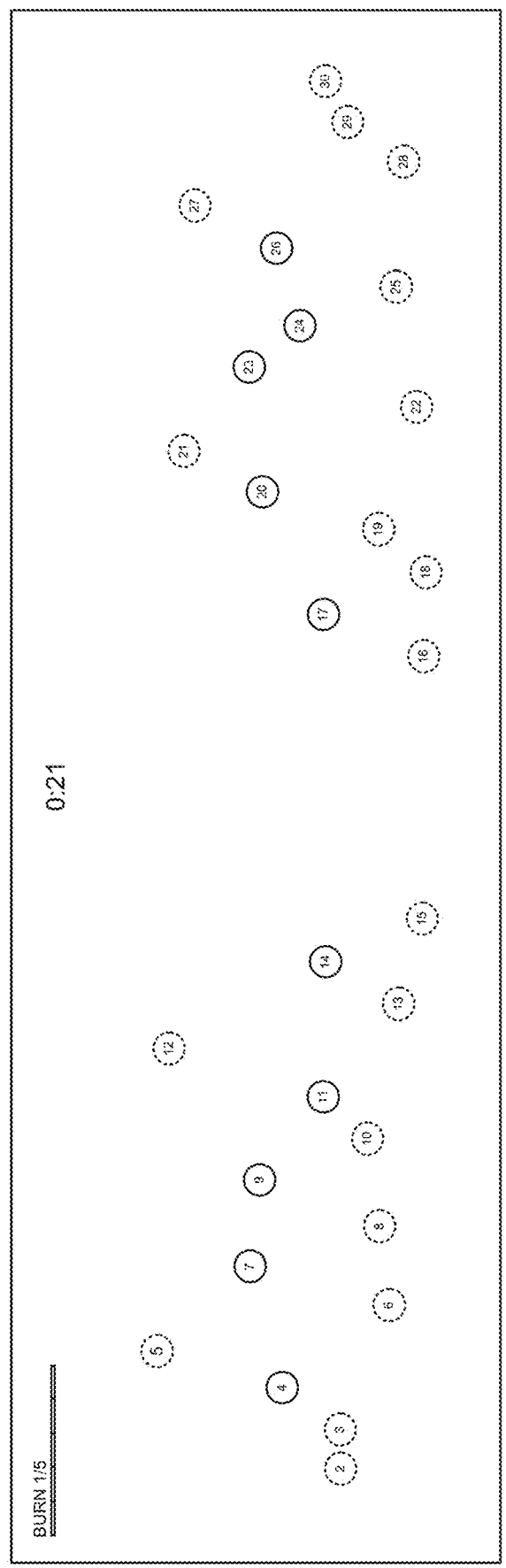
Figure 37:
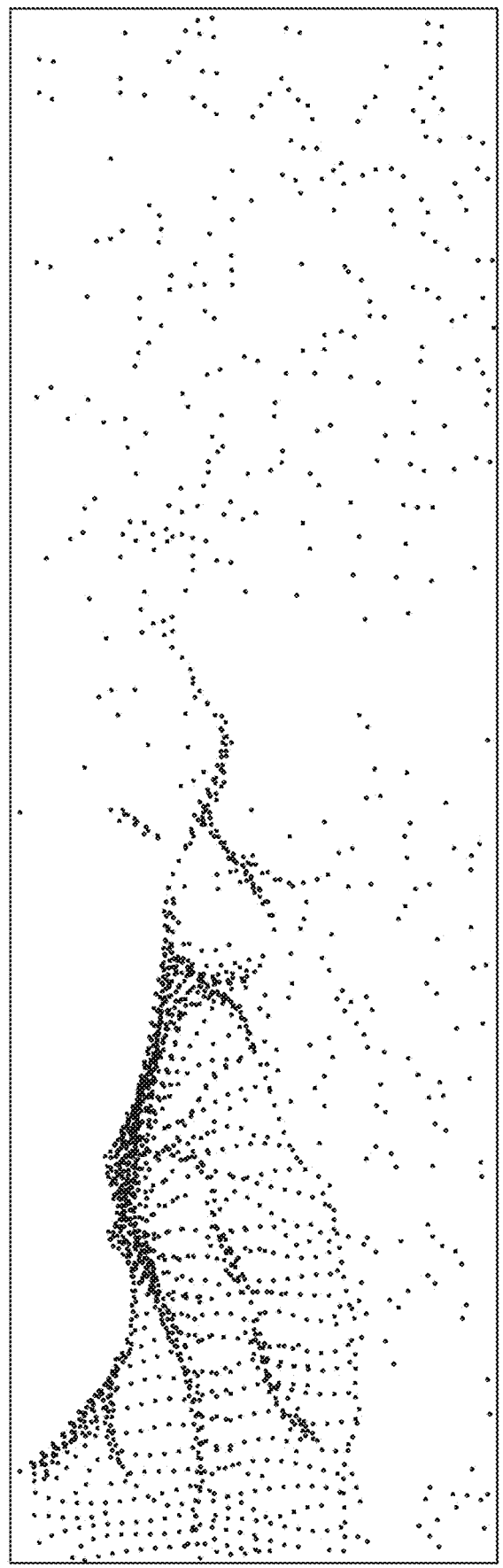

The first stage is named "fire up." This game may include several rounds. The object may be to motivate participants to push for a high level of power. Circles corresponding to participants may become brighter and fill-in as the power increases. The circles may also rise based on power. FIG. 36 shows an image from display device 116 during the first stage. The object may be for each participant to keep his/her circle as high and as bright as possible during intervals which may each be 1 minute, for example. After each round, top male and female performers, based on average power, may be displayed for that round. After each round, an abstract animation may be displayed on display device 116 as illustrated in FIG. 37. This dynamic animation may be driven by the power generated by class participants. As power increases, the animation may become brighter and movement within the animation may become faster.

After the first stage has finished, an image may be displayed on display device 116 that may indicate the overall leaderboard for the class, based on the energy expended. The leaderboard may be divided based on gender.

After the first stage, a recovery period may be provided during which an abstract dynamic animation may be displayed, where the animation may be dynamic based on the power generated by participants in the class.

Between stages, an image may also be displayed on display device 116 that indicates progress of the class toward the class goal mentioned above.

Figure 38:

As noted above, no game may be provided during the second stage of this class. Instead, throughout this stage, an abstract animation may be provided on display device 116. The animation may be responsive to the collective power generated by class participant. FIG. 38 illustrates such an abstract animation. The brightness and speed of movement of the animation may increase in response to the cumulative power generated by participants in the class.

At the end of the second stage, an overall leaderboard may be displayed showing the leaders in terms of energy expended among participants over the class to this point. Also, an image may be displayed on display device 116 which indicates the progress of the class toward the class goal.

After the second stage, a recovery period may be provided with an abstract animation, which again may be driven by the exercise signals related to power generated by the participants of the class.

Figure 39:
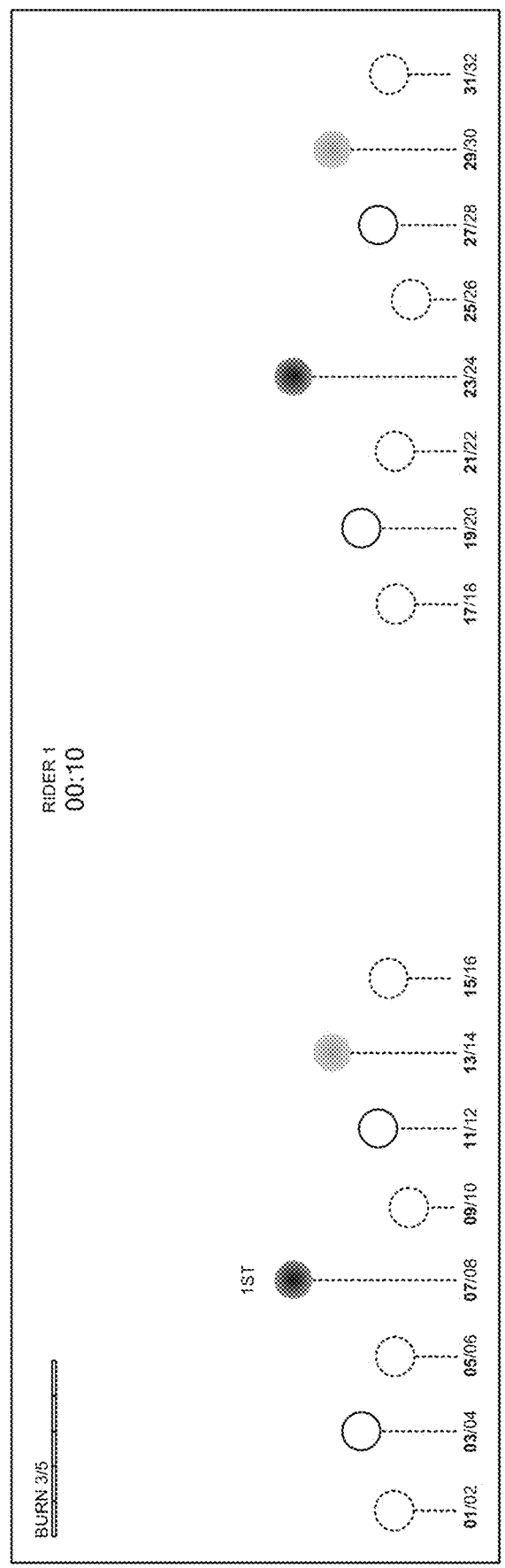
Figure 40:
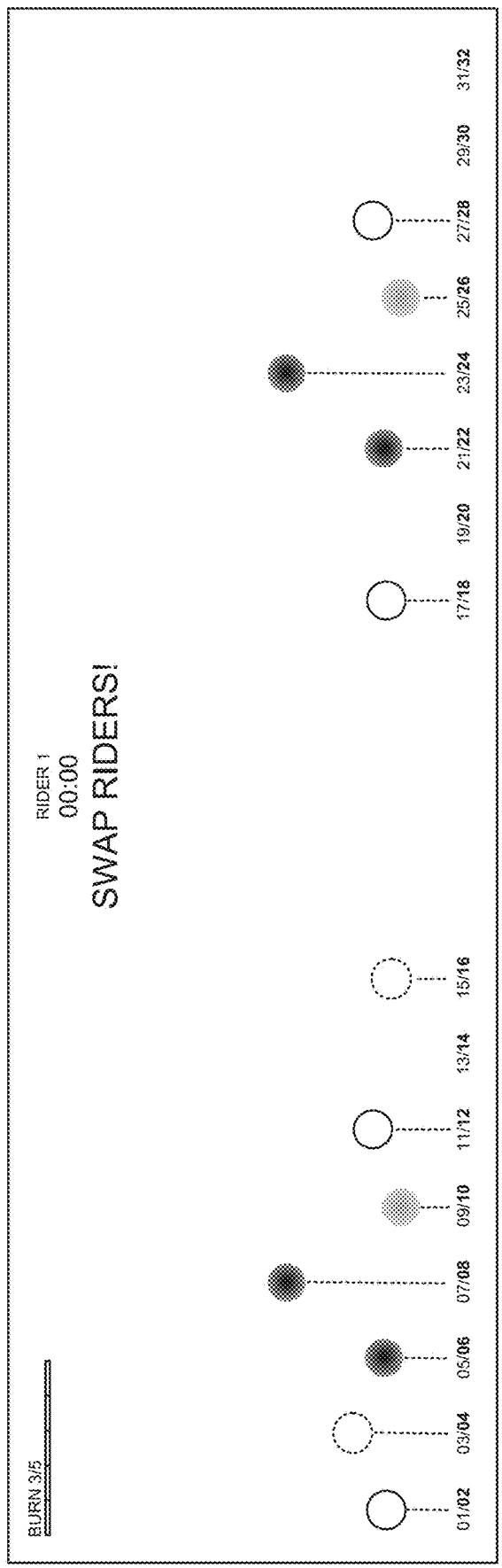

The third stage of this class may represent a pairs game. Each participant may be paired dynamically with another participant, for example a participant located near them. The game may run like a relay race. The goal may be to maximize the distance measurement during the game period. Partners may alternate back and forth between racing and resting. As illustrated in FIG. 39, a single circle may be illustrated for each pair of participants. In FIG. 39, the image shows that one of each pair of bicycles (indicated by a bolded number) may be driving the circle. The intensity of the circle may be related to the power generated by the active participant and the movement of the circle may be related to the distance measurement from the active participant. At the end of a predetermined time, the first of each pair of riders may stop controlling the circle and the second of each pair of participants may begin to control the circle. Thus, as illustrated in FIG. 40, the other of each pair bicycles of each pair may now control the circle. The intensity of the circle may be related to the power generated by the active participant. The circle for each may pair continue to move from where the circle left off based on the other participant in the pair so that the distance the circle moves may represent the distance measure for each participant of the pair during the time that that participant is active. Once each circle reaches the top of the display, web application module 112 may cause the circle to reverse direction. A label may indicate which team is leading.

At the end of this stage, the top performing pairs may be displayed indicating the cumulative distance measure of the team. Again, the overall leaderboard for the class up to this point may be displayed based on cumulative energy expended. An image indicating progress toward the class goal may also be created on display device 116.

After the third stage, a recovery period may be provided with a dynamic animation which again may be driven by the collective power of the participants in the class.

The fourth stage may be similar to the second stage. No game may be provided but an abstract animation may be displayed on display device 116 which is driven by the collective power generated by participants in the class. After the fourth stage, a class leaderboard may be displayed as well as an image illustrating progress of the class toward the class goal. After the fourth stage, a recovery period may be provided during which time an abstract animation may be displayed on display device 116 that varies based upon the collective intensity riders in the room.

Figure 41:
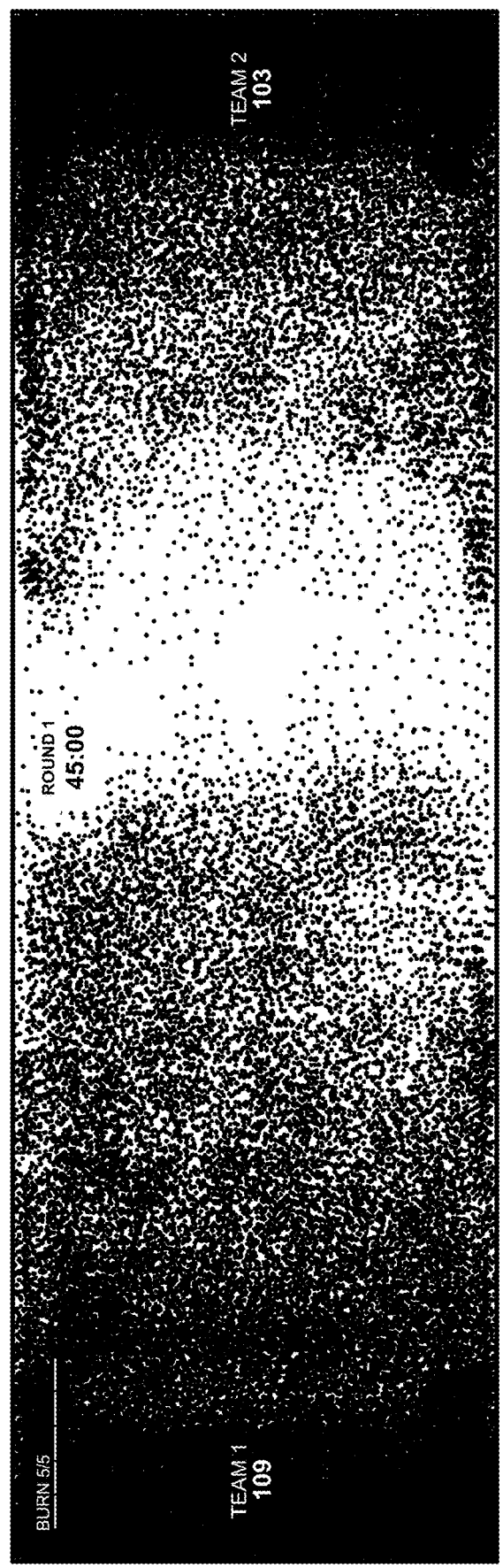

Stage 5 of this class is named "heat wave." For this game, the class may be dynamically divided into two teams. In a first portion of this stage, an abstract animation may be displayed on display device 116, driven by the collective power exerted by the participants in the stage. The game may begin during the second half of the stage. As illustrated in FIG. 41, web application module 112 may generate an output signal to cause display 116 to display an image that may include a brighter area in the middle of the screen that fades to darker colors in opposite directions from the middle portion. The image may then shift based on the average power being generated by each team. As illustrated in FIG. 41, as team 1 exerts a higher average team power (e.g., wattage), the brighter central area of the image may be pushed toward team 2. The game may be played in three rounds of fixed periods. Alternatively, the game may be played until the central portion of the image has been pushed all the way to one edge. Alternatively, it may be desirable to weight the average team power by a factor related to the distance that the central portion of the image has been displaced. For example, at the beginning of the game, this the weighing factor may be 1.0 for each team. As team 1 begins to push the central area of the image toward team 2, team 1's average power may be weighted by a factor that decreases based on the distance that team 1 has pushed the central portion of the image towards team 2. That is, the further team 1 pushes the central portion of the image, the more difficult it becomes for team 1 to push it any further. Alternatively, movement based on average team power may be less dramatic toward the beginning of the game and may become more dramatic by the end of the game.

After each round of this game, the winning team may be acknowledged. Display device 116 may also display the top male and female performers in terms of average power for each of the two teams. If a team includes members of a single gender, the top two performers may be displayed. At the end of the stage, the overall leaderboard may be displayed showing top performance in total energy throughout the class. The leaders may be divided by gender. Also at the end of the game, display device 116 may also display whether or not at the end of the class the class goal has been achieved. After stage 5, a recovery animation may be displayed to end the class. As with previous recovery animation, the abstract animation may be altered based on power generated by participants.

Figure 42:
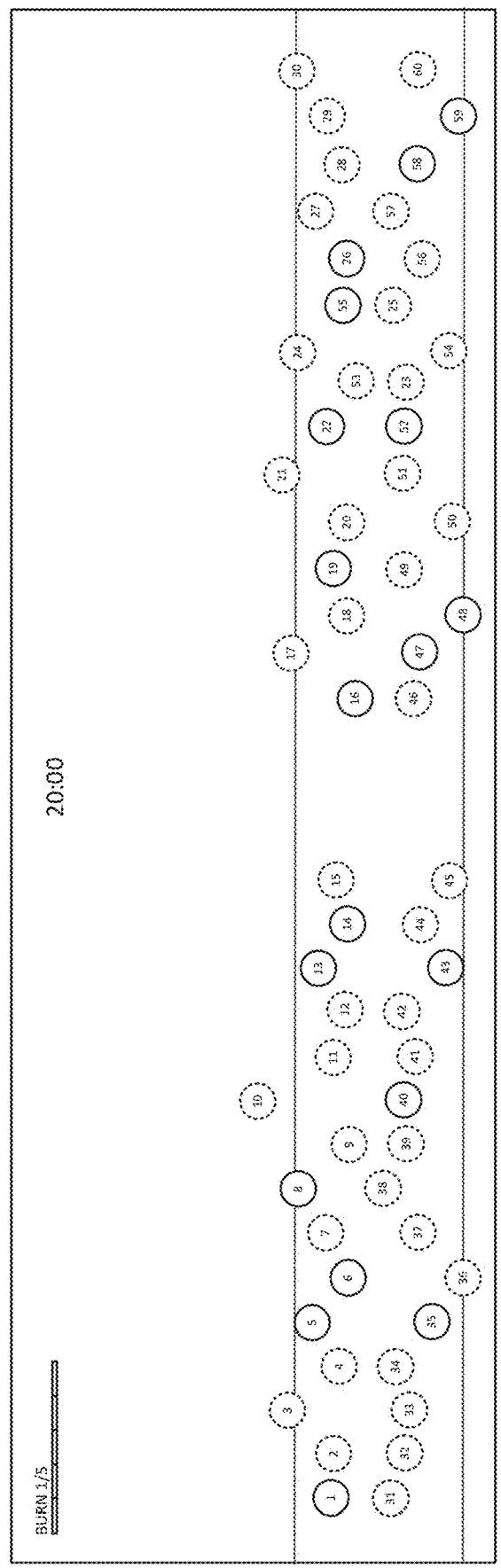
Figure 43:
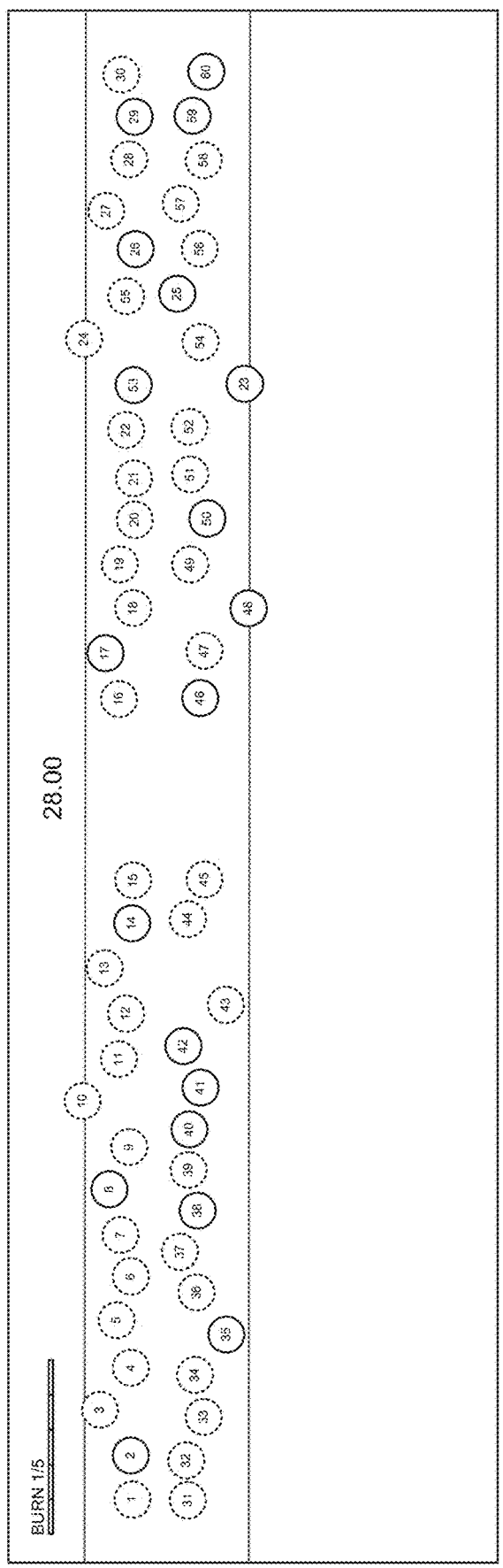

The games in either class may be played in any order. Furthermore, other games may be substituted for those described above. An example of a substitute game for this class is illustrated in FIGS. 42 and 43. This game is played on an individual basis, and thus may be substituted for the game of stage 1, for example. This game may use a training protocol called 30-20-10, where the object is to ride at a moderate intensity for 30 seconds, a hard intensity for 20 seconds and a very hard intensity for 10 seconds. Alternatively, a training protocol of three one minute periods of increasing rotation rate may be employed. This may be repeated a series of times, for example 5 times. Participants may compete individually. The circle corresponding to each participant may change in the same manner as previously described with other games in this class. That is, as the power of each participant increases, the circle may become more intense and fill in. For each participant, the movement of the circle in a vertical direction may be driven by the participant's rotational rate. Horizontal bands may mark the safe area in which the participant may peddle. As a participant reaches the top boundary, an instructor may suggest to that participant to increase his/her power (resistance) to make it more difficult to maintain that rotational rate. The converse may also be true when a participant reaches the lower boundary. When it is time to increase the intensity, the horizontal lines may move upwardly as illustrated in FIG. 43 as compared to FIG. 42.

The coding for the games generated by the web application 112 may be organized in an architecture that may be modular and expandable. The code may include a core module to perform functions common to all of the games. The code unique to each game may be plugged into the application and call the common functions as needed.

The games described above may be implemented with one or more rounds of each game. Also, the games can be implemented for any number of teams.

Figure 45:
Figure 46:
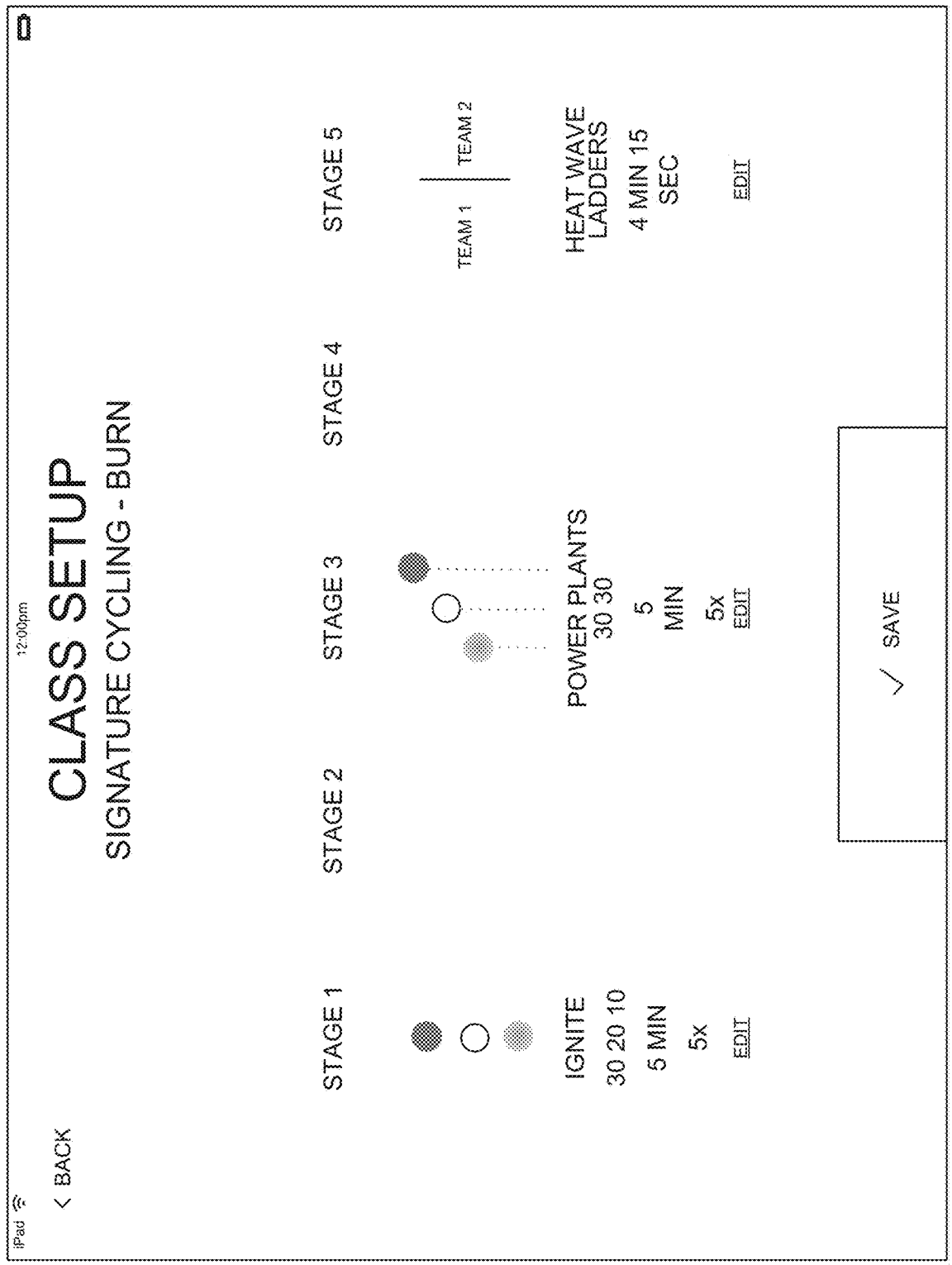
Figure 47:
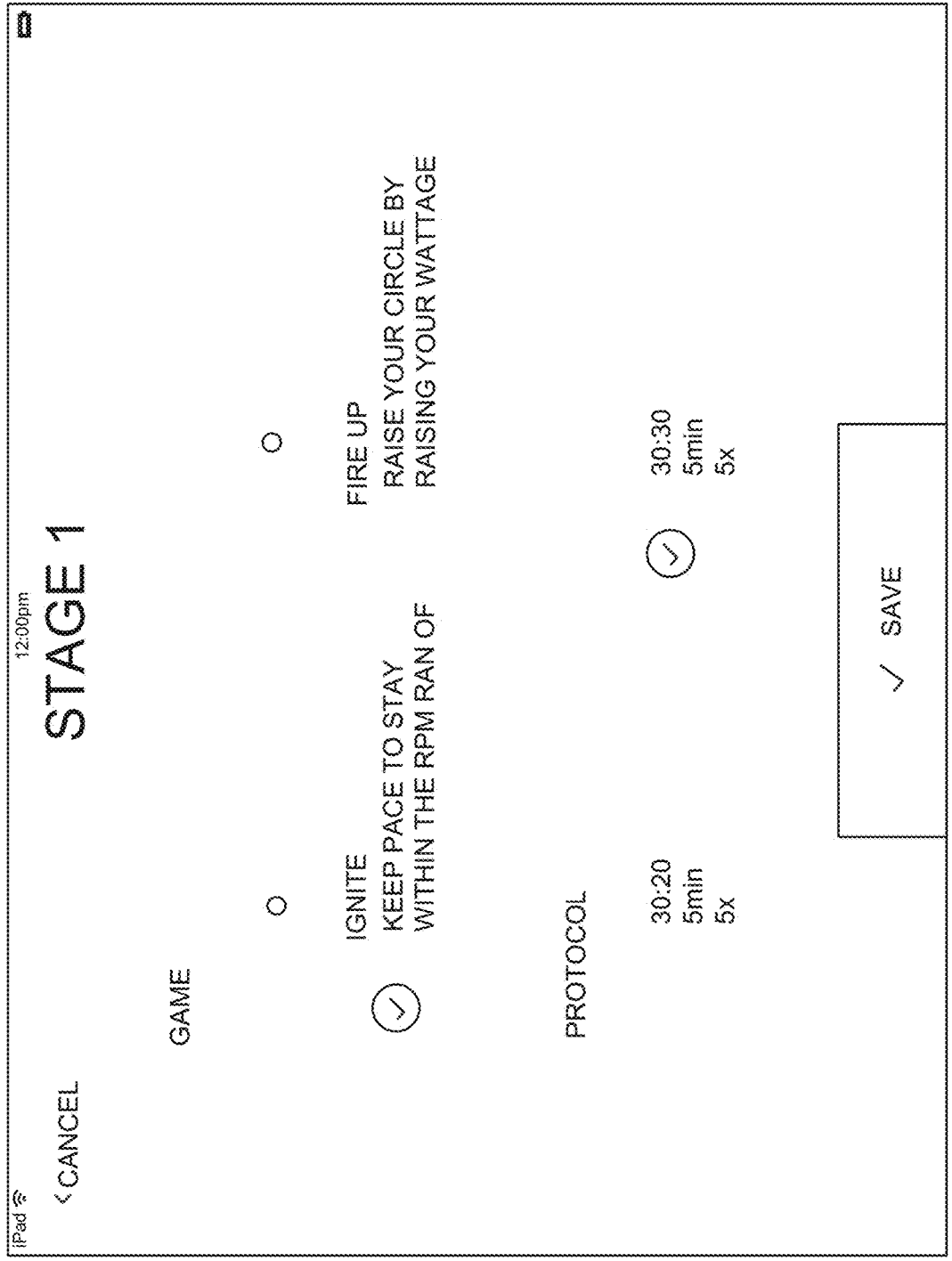

FIGS. 44-52 provide examples of images that web application module 112 may cause to be displayed on instructor console 122. As illustrated in FIG. 44, when an instructor first logs into the system to conduct a class, the system may request the instructor to confirm the class. As illustrated in FIG. 45, the instructor may then have an opportunity to confirm and/or change the class to be taught. The class designation may include information concerning the location and time of the class, the instructor and whether the class is of the first training protocol (called "Build") or of the second training protocol (called "Burn"). Web application module 112 may provide instructor console 122 with the opportunity to setup the stages in the class. As illustrated in FIG. 46, this may involve picking an appropriate game for each stage, picking a training protocol for each game, setting a time for each stage and the number of rounds within each stage. FIG. 47 illustrates a screen which may be provided to instructor console 120 by web application module 112 to edit stage 1. The instructor may choose which of two games to play in stage 1 and the training protocol for either of the games.

Figure 48:
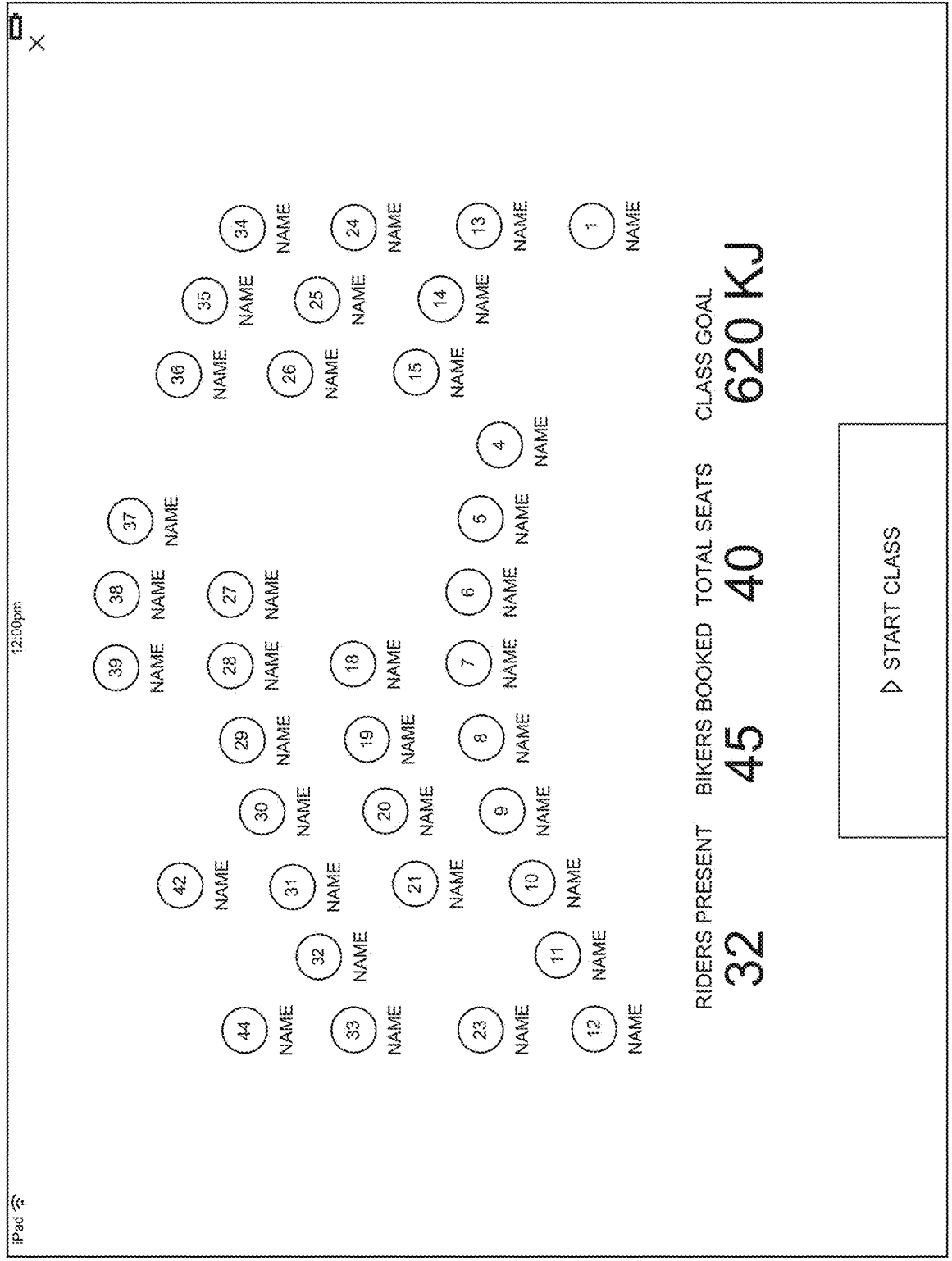

Once setup is completed, and the class is about to start, web application module 112 may provide instructor console 122 with a display of the room indicating all of the occupied bicycles and the names of the participants riding the bicycles as illustrated in FIG. 48. The instructor also may move participants to other bicycles and/or opt participants out of the games (changing the nature, e.g., color, of the circle). This display also provides a button for the instructor to start the class.

Figure 49:
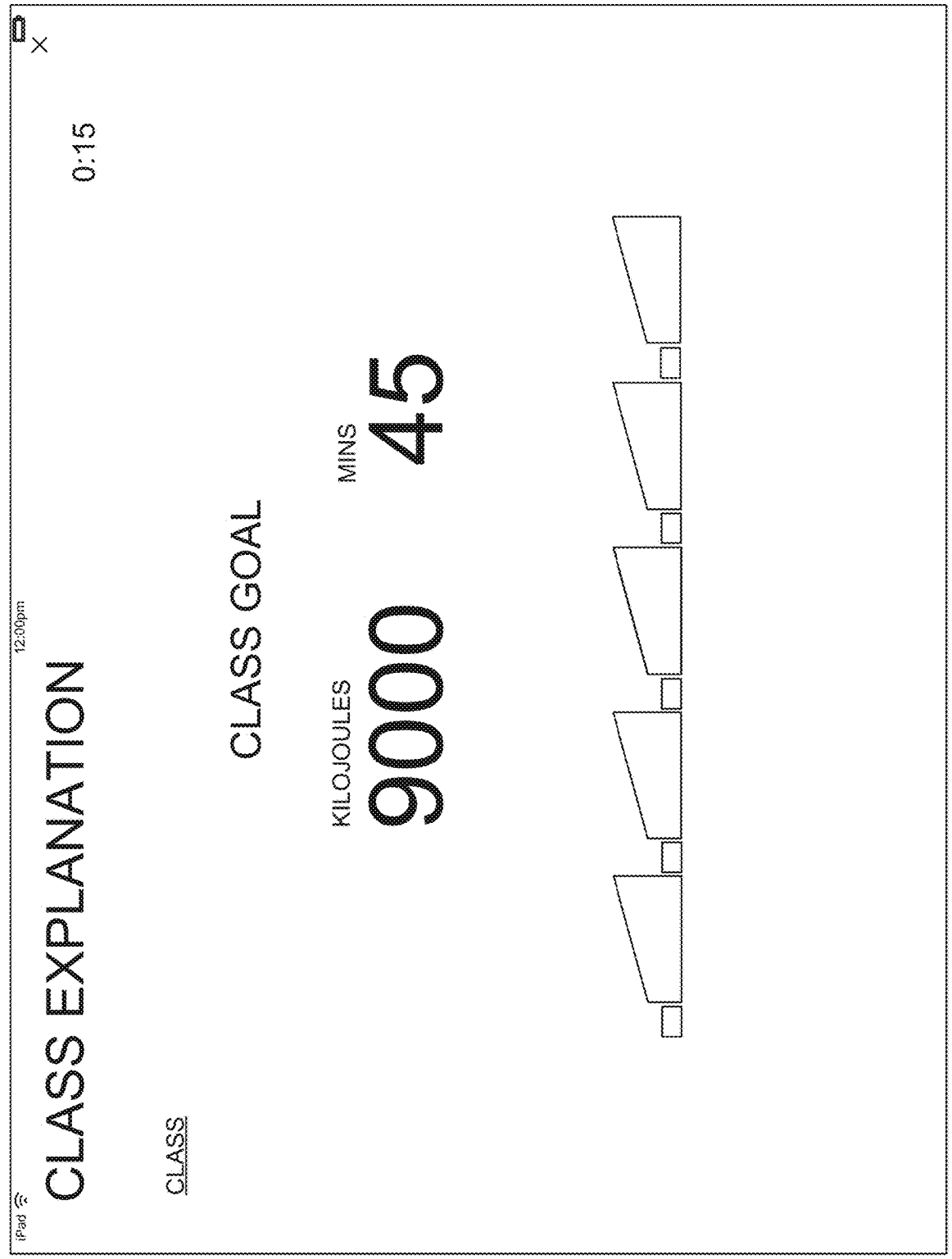
Figure 50:

When the instructor presses the start class button, web application module 112 may provide to instructor console 122 a screen as illustrated in FIG. 49 which may provide a summary of the class. An instructor may share with the class the overall class goal and the structure of stages and warm-up/recovery periods associated with the class. Web application module 112 may then present to instructor console 122 a screen indicating a warm-up period, as illustrated in FIG. 50. At the bottom of the screen, the instructor may be presented with a button to allow for the initiation of the first game.

Figure 51:
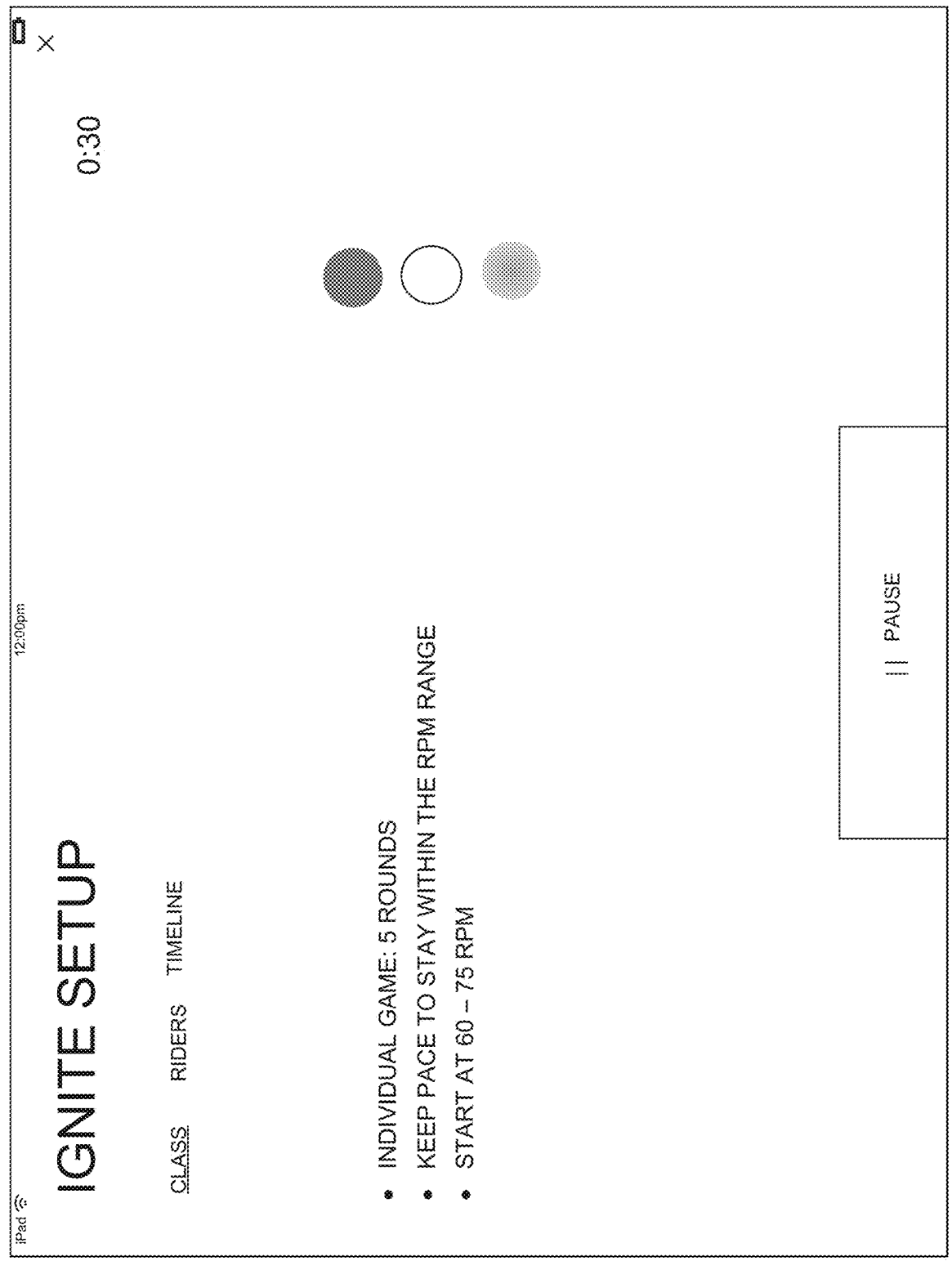

When that button is pressed, web application module 112 may cause instructor module 122 to display information about the first game, as illustrated in FIG. 51. This may be the information that the instructor shares with participants in the class. The button also causes the display device 116 to display the games as illustrated in FIGS. 5-32.

Figure 52:
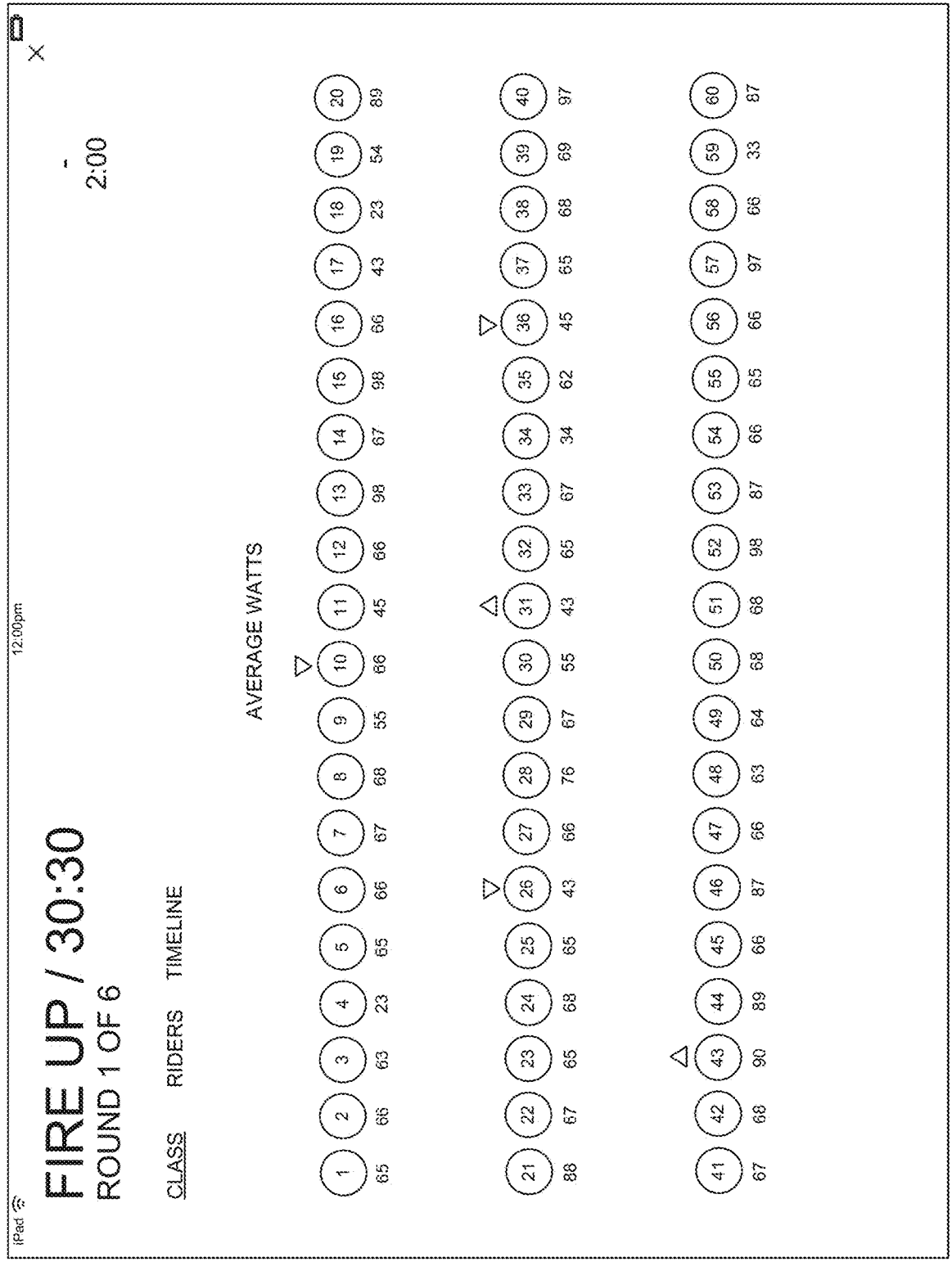

As illustrated in FIG. 52, as the game begins, all bicycles may be arranged in sequence with a performance measurement indicated associated with each bicycle. Web application module 112 may cause instructor console 122 to display upwardly pointing arrows or downwardly pointing arrows with participants who are determined to be best or worse performing to assist the instructor in coaching the class.

Figure 58:
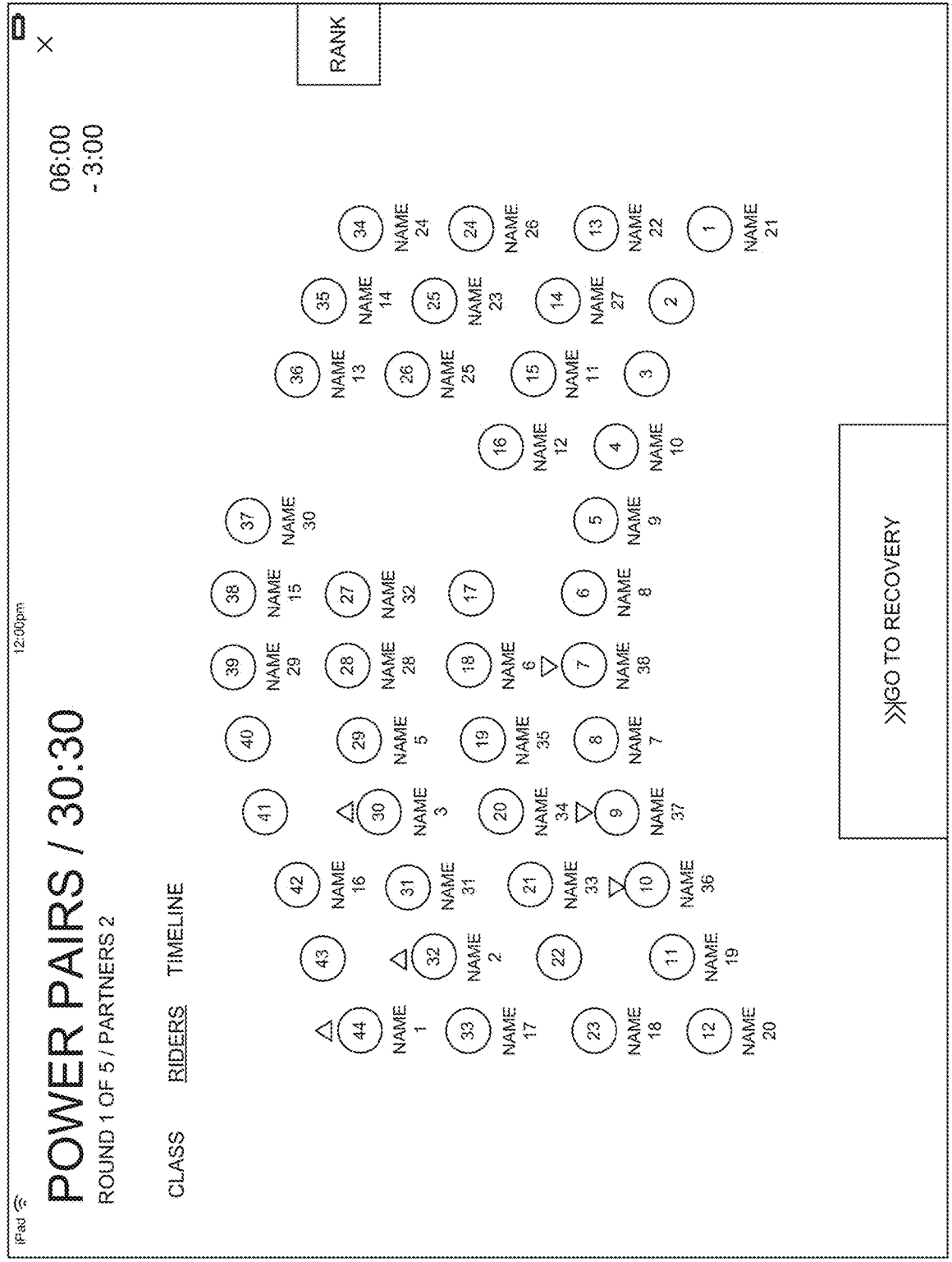
FIGS. 58-59 illustrate displays of an instructor console in an exercise system according to an embodiment of the invention.

As indicated in the upper left corner of a screen during a class, the instructor may change a class view to a rider view or a timeline view. FIG. 58 illustrates a rider view. All of the participants are displayed with their names in a layout that reflects the studio layout. Performance values are also displayed. The buttons along the right side allow the instructor to select to display either rank, watts, distance or rotation rate.

Figure 59:
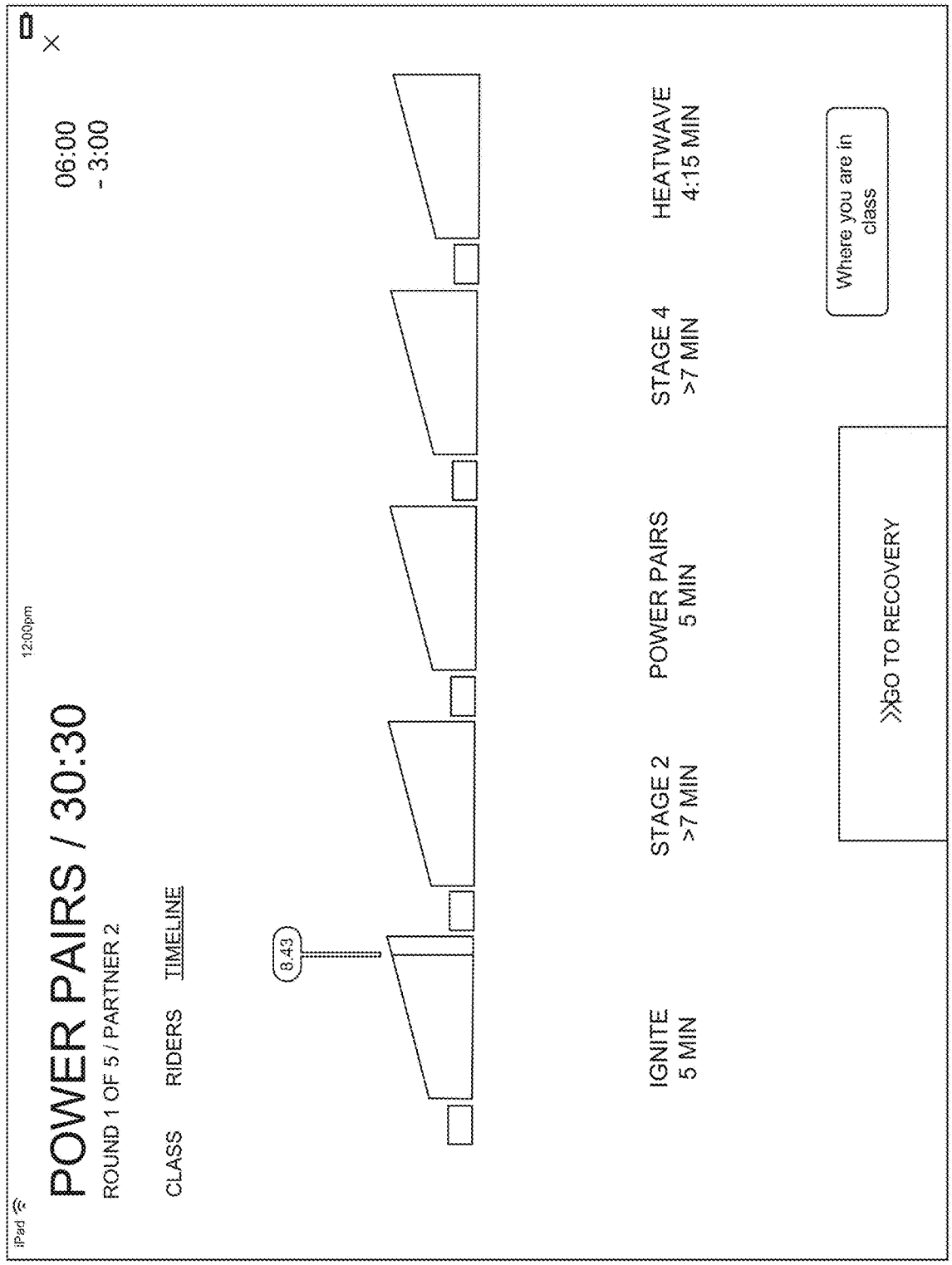

When the timeline view is selected as illustrated in FIG. 59, the overall layout of the class is displayed, along with an indication of where the class is in the overall class layout.

Figure 53:
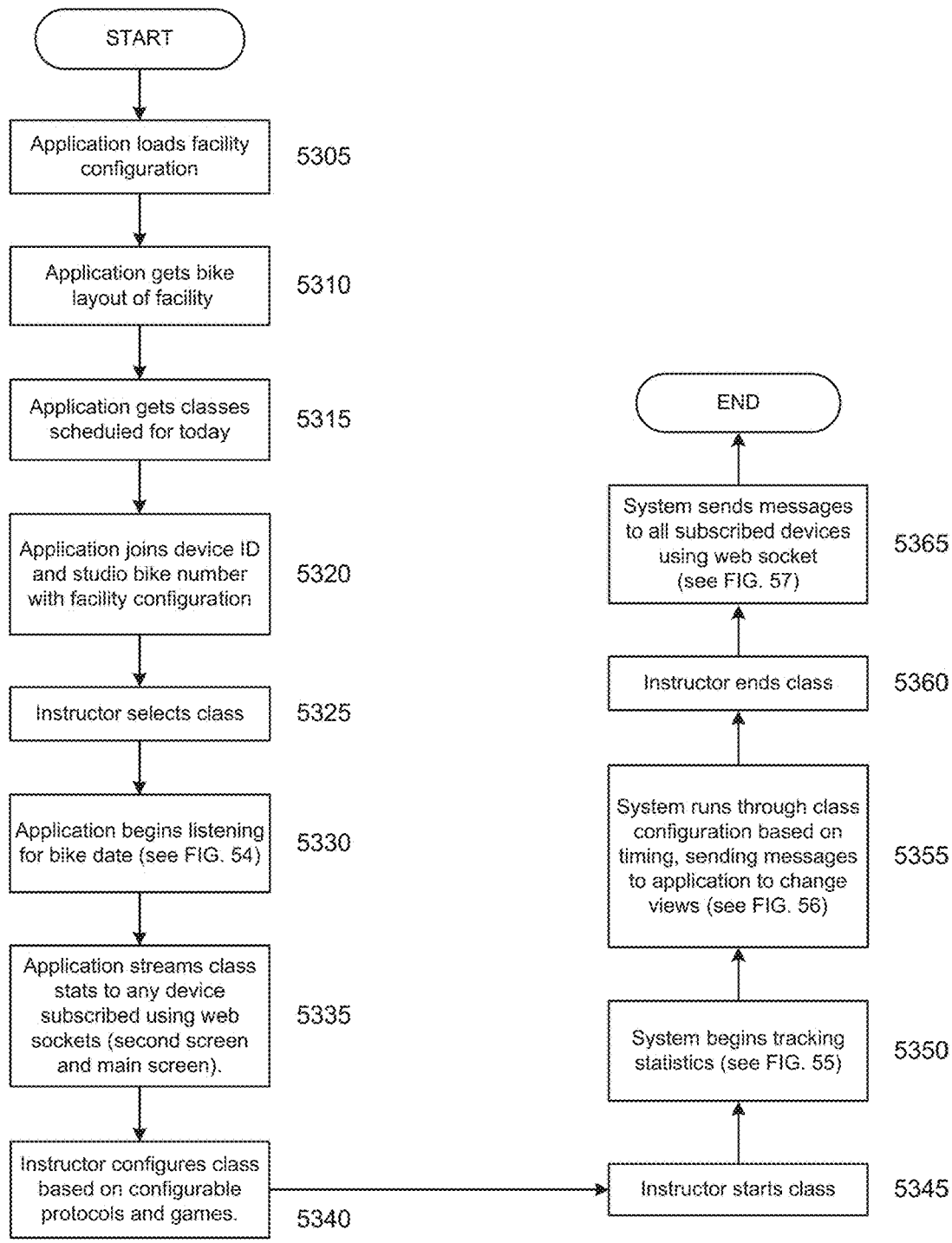
FIG. 53 illustrates an overall application flow of an exercise system according to an embodiment of the invention.

FIGS. 53-57 provide example process flows for various elements and embodiments of the exercise system. FIG. 53 shows how data from connected bicycles 102 may be streamed to multiple devices during a class. At the start of a session, pre-processor module 110 may load the facility configuration 5305, get bicycle 102 layout for the facility 5310, and get classes scheduled for the day (or other time period) 5315. At this time, data may be obtained from local database 108, permanent database 120 and/or reference data 216 related to participants who have registered for the class and information related to the participants (e.g., gender, alias, statistics, etc.). As noted above, in some games the class may be divided into teams based on bicycle placement. Loading the facility configuration, bicycle 102 layout, and class may allow web application 112 to perform the dynamic assignment of bicycles 102 to teams. Pre-processor module 110 may join the device ID and studio bicycle number for each bicycle 102 to the facility configuration 5320. A class selection may be entered 5325 via instructor console 122. Pre-processor module 110 may listen for bicycle 102 data 5330, as described below in relation to FIG. 54. Web application software module 112 and/or cycling processor module 114 may stream class statistics to any device subscribed using web sockets 5335, as discussed above, during the class. The class may be configured based on configurable protocols and games 5340, such as the games described above, via instructor console 122. When the class begins 5345 via instruction from instructor console 122, web application software module 112 and/or cycling processor module 114 may track statistics 5350 from the bicycles 102, as described below in relation to FIG. 55. Pre-processor module 110 may run through the class configuration based on timing and send messages to web application software module 112 and/or cycling processor module 114 to change views (e.g., change information being displayed) 5355, as described below in relation to FIG. 56. The class may end 5360 via instruction from instructor console 122, and web application software module 112 and/or cycling processor module 114 may send messages to all subscribed devices using web socket 5365, as described below in relation to FIG. 57.

Figure 54:
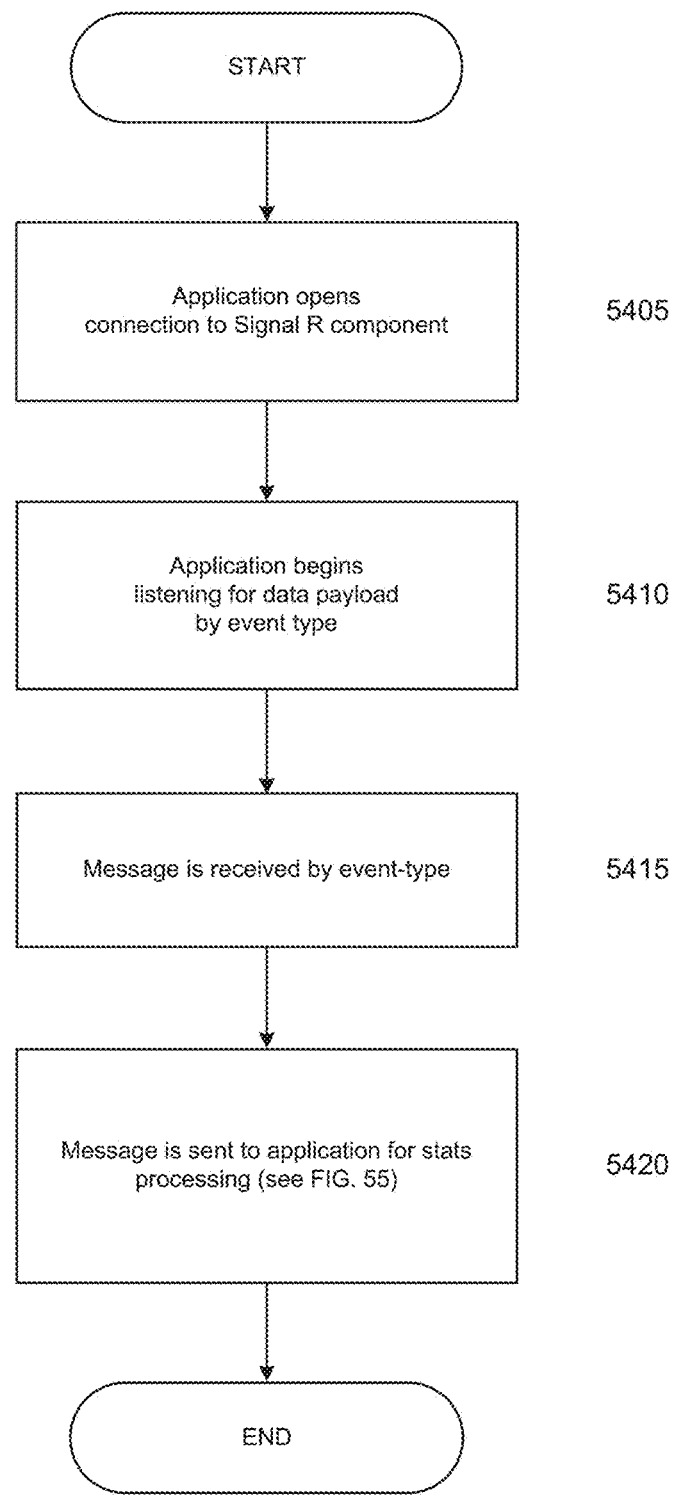
FIG. 54 illustrates a bicycle data flow of an exercise system according to an embodiment of the invention.

FIG. 54 shows how bicycle 102 data can be sent from pre-processor module 110 to web application software module 112 and/or cycling processor module 114. Pre-processor module 110 opens a connection to bicycle 102 to receive bicycle 102 data 5405. Pre-processor module 110 may start listening for data payload by event type 5410. For example, bicycles 102 and/or other exercise equipment may generate various data signals which may be applicable in various ways depending on game type or class type, etc., as discussed above. Pre-processor module 110 may receive data from bicycle 102 by event type 5415 after a class begins. The received data may be used for stats processing 5420, as described below in relation to FIG. 55.

Figure 55:
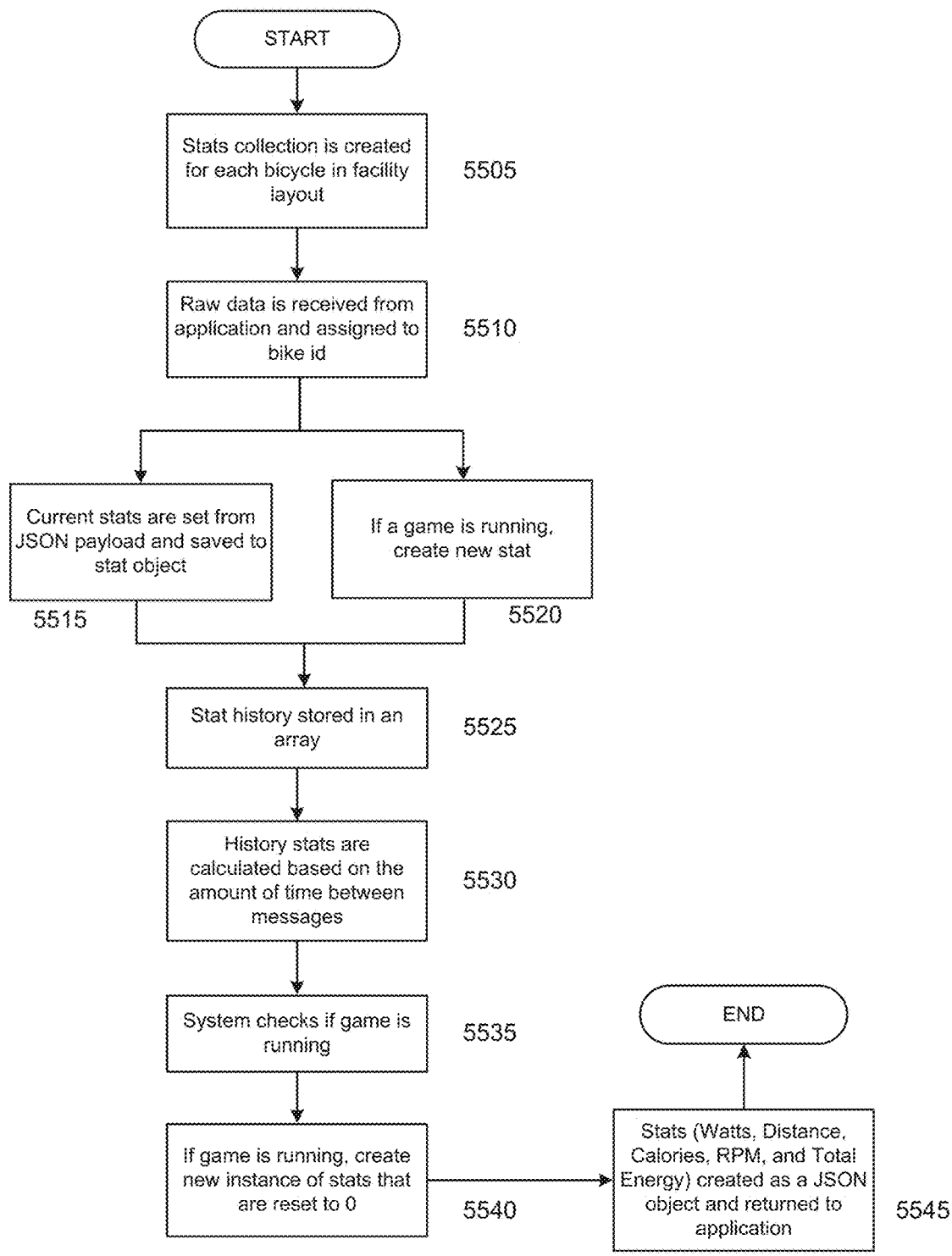
FIG. 55 illustrates a flowchart for collecting statistics according to an embodiment of the invention.

FIG. 55 shows how stats can be generated for individual bicycles 102 both for games and for overall class reporting. Pre-processor module 110 may create a stats collection for each bicycle 102 in the facility layout 5505. Raw data may be received from each bicycle 102 and assigned to the stats collection associated with each respective bicycle 102 (for example, based on bicycle ID) 5510. Current stats for each bicycle 102 may be set from the received JSON payload and saved to stat object 5515. If a game is running, new stats for the game can be created 5520. Stat history may be stored in an array 5525, and history stats can be calculated based on the amount of time between messages 5530 received from bicycle 102. Historical stat data may be used to track a user's individual exercise progress. Pre-processor module 110 may also check to see if a game is running 5535 (for example, as set by instructor console 122 as described above). If so, a new instance of stats may be created 5540. This new instance may be reset to 0 (i.e., may not be linked to the historical data) upon creation, so that it may be used for the game only. Stats can be created as a JSON object and returned to web application software module 112 and/or cycling processor module 114 for display 5545.

Figure 56:
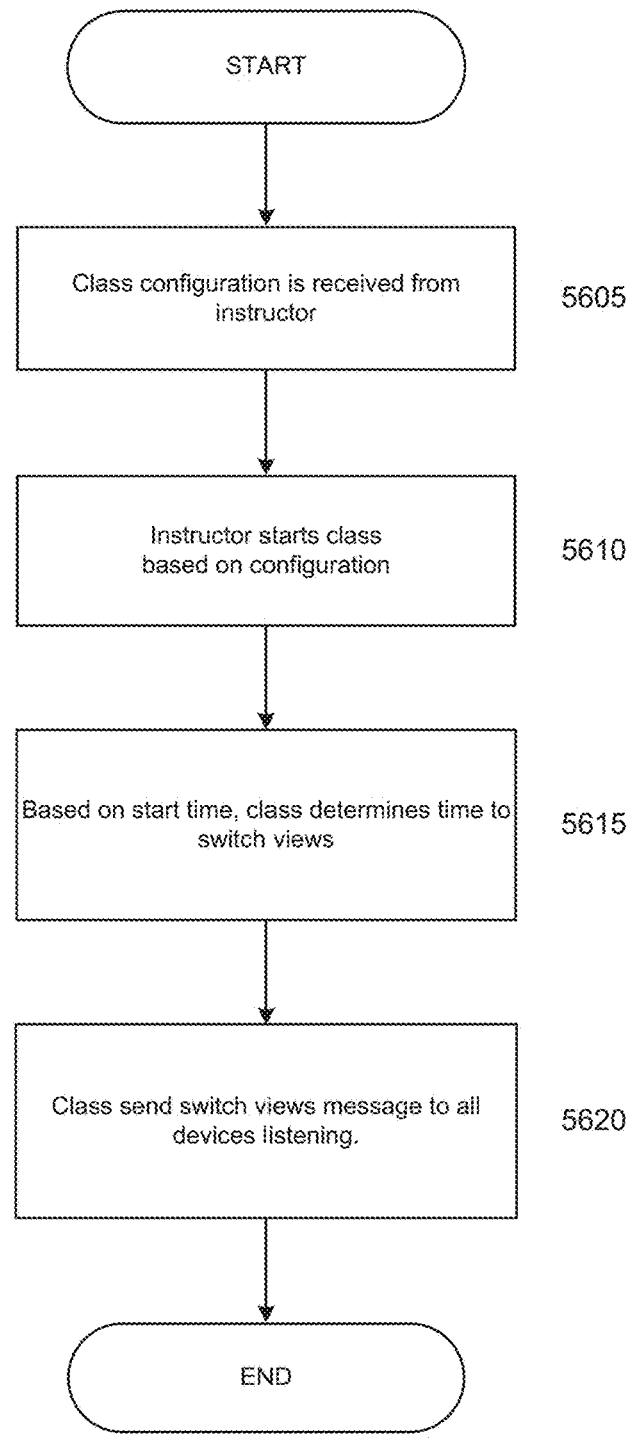
FIG. 56 illustrates a flowchart for synchronizing devices in an exercise system according to the invention.

FIG. 56 shows how devices listening to web application software module 112 and/or cycling processor module 114 can stay in sync. Pre-processor module 110 may receive class configuration 5605 from instructor console 122, and the class may begin 5610. Based on class start time, web application module 112 may determine time to switch views to be displayed 5615. Web application module 112 and/or cycling processor module 114 may send switch view messages to all devices listening at the determined time 5620. Thus, all users of all bicycles 102 in the class may see the same information about the class or game in sync.

Figure 57:
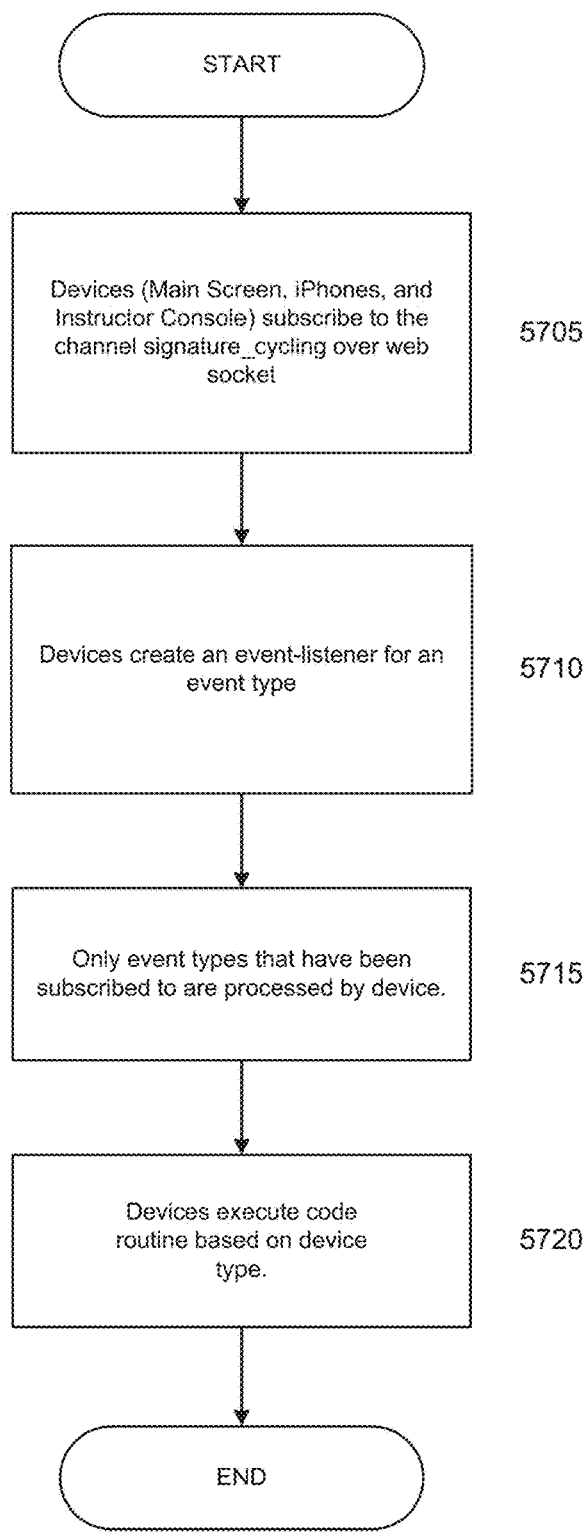
FIG. 57 illustrates a flowchart for connecting each device to a cycling application in an exercise system according to the invention.

FIG. 57 shows how devices connect to the system and listen for data. Devices (e.g., display 116, smart phones, tablets, instructor console 122, any digital devices associated with digital platform 204, etc.) can subscribe to a web socket channel (e.g., channel "signature cycling") 5705. The subscribed devices may create an event listener for an event type 5710. Those event types for which a device has created an event listener may be processed by the device. When such events are received by the device, they may be processed 5715. Devices may execute code based on device type to handle the events (e.g., display data relating to a game or class, as discussed above) 5720.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

What is claimed is:

1. An exercise class apparatus used in a class, the apparatus comprising:
   a plurality of pieces of exercise equipment, each piece of the plurality of pieces of exercise equipment configured to output a plurality of exercise signals relating to exercise performance;
   a computer system including:
      at least one electronic storage device configured to store the plurality of exercise signals;
      at least one processor configured to generate an output signal containing an animation, the animation including at least one graphic shape, each graphic shape of the at least one graphic shape corresponding to at least two different exercise signals from one piece of the plurality of pieces of exercise equipment, a first exercise signal of the at least two different exercise signals including data relating to a first aspect of exercise performance from the one piece of the plurality of pieces of exercise equipment, and a second exercise signal of the at least two different exercise signals including data relating to a second aspect of exercise performance from the one piece of the plurality of pieces of exercise equipment, each graphic shape animated with a first animated feature corresponding to the first exercise signal and a second animated feature corresponding to the second exercise signal; and
   at least one display device, visible from each piece of the plurality of pieces of exercise equipment, configured to receive the output signal and display the animation.

2. The apparatus of claim 1 wherein the at least one processor is configured to, for each graphic shape:
   generate the output signal to define the graphic shape; and
   cause the graphic shape to spin at a rate related to the first exercise signal and move along a path based on the second exercise signal, wherein the first animated feature includes the spin and the second animated feature includes the move along the path.

3. The apparatus of claim 2, wherein a thickness of a line forming the graphic shape corresponds to a third exercise signal of the plurality of exercise signals.

4. The apparatus of claim 3 wherein the third exercise signal corresponds to power.

5. The apparatus of claim 2 wherein:
   the first exercise signal indicates rotation rate or speed of the one piece of the plurality of pieces of exercise equipment; and
   the second exercise signal corresponds to distance of the corresponding one piece of the plurality of pieces of exercise equipment or sensing system.

6. The apparatus of claim 2 wherein, for each graphic shape, the at least one processor is configured to cause the graphic shape to change color when a user exercising on the one piece of the plurality of pieces of exercise equipment is on track to at least match a distance from a previous session.

7. The apparatus of claim 2 wherein the at least one processor is configured to cause the output signal to produce a display indicating top performers after a predetermined time.

8. The apparatus of claim 1 further comprising a user display device associated with a user and coupled to the at least one processor,
   the user display device being constructed and arranged to display individual information concerning the user.

9. The apparatus of claim 8 wherein the individual information includes cumulative data for the user over the class.

10. The apparatus of claim 9 wherein the individual information includes data comparing the user to the overall class.

11. The apparatus of claim 8 wherein the user display device provides a software application to enable the user to register for the class.

12. The apparatus of claim 8 wherein the user display device is configured to receive data from the at least one processor and not directly from the plurality of pieces of exercise equipment.

13. The apparatus of claim 8 wherein the user display device is removable from the one piece of the plurality of pieces of exercise equipment.

14. The apparatus of claim 1 wherein:
   each piece of the plurality of pieces of exercise equipment in the class is organized in one of two or more teams; and
   for each graphic shape, the at least one processor is configured to generate the output signal so that the graphic shape drops into a second graphic shape for a corresponding team when at least one exercise signal of the at least two different exercise signals corresponding to the graphic shape achieves a predetermined value, wherein the second graphic shape is different from the graphic shape.

15. The apparatus of claim 14 wherein the graphic shape rotates in response to the second exercise signal and a thickness of a line forming the graphic shape corresponds to a third exercise signal of the plurality of exercise signals, wherein the second animated feature includes rotating of the graphic shape in response to the second exercise signal.

16. The apparatus of claim 15 wherein:
   the plurality of pieces of exercise equipment include stationary bicycles; and the second exercise signal corresponds to rotation rate of a corresponding stationary bicycle and the third exercise signal corresponds to power from the corresponding stationary bicycle.

17. The apparatus of claim 14 wherein the plurality of pieces of exercise equipment are stationary bicycles and the at least one exercise signal corresponds to distance of a corresponding stationary bicycle.

18. The apparatus of claim 14 wherein the at least one processor is configured to generate the output signal, when the second graphic shape is completed, to cause another second graphic shape to be built from a dropping of graphic shapes.

19. The apparatus of claim 1 wherein the at least one processor is configured to generate each graphic shape moving along a path in response to the first exercise signal, the at least one processor being configured to generate the output signal to cause the animation to include upper and lower boundaries along the path for a user to keep a graphic shape of the at least one graphic shape corresponding to the one piece of the plurality of pieces of exercise equipment between the upper and lower boundaries, wherein the first animated feature includes the moving along the path.

20. The apparatus of claim 19 wherein, for each graphic shape, the at least one processor is configured to generate the output signal to cause an appearance of the graphic shape to change based on the second exercise signal, wherein the second animated feature includes the change in appearance.

21. The apparatus of claim 20 wherein:
the plurality of pieces of exercise equipment include stationary bicycles; and
the second exercise signal corresponds to power.

22. The apparatus of claim 19 wherein the at least one processor is configured to generate the output signal to cause the animation to move the upper and lower boundaries after a predetermined time.

23. The apparatus of claim 19 wherein:
the plurality of pieces of exercise equipment include stationary bicycles; and
one of the first exercise signal and the second exercise signal corresponds to rotation rate.

24. The apparatus of claim 1 wherein the plurality of pieces of exercise equipment include a plurality of stationary bicycles.

25. The apparatus of claim 24 wherein the plurality of exercise signals include signals representing two or more of rotation rate, distance, power and energy.

26. The apparatus of claim 25 wherein one of the plurality of exercise signals representing distance represents a combination of rotation rate and power.

27. The apparatus of claim 1 wherein the at least one processor is configured to:
generate the output signal to display the graphic shape for each piece of the plurality of pieces of exercise equipment;
generate the output signal to cause the graphic shape for each piece of the plurality of pieces of exercise equipment to change appearance based on the first exercise signal, wherein the first animated feature includes the change in appearance; and
generate the output signal to cause the graphic shape for each piece of the plurality of pieces of exercise equipment to move a distance corresponding to the second exercise signal, wherein the second animated feature includes the move.

28. The apparatus of claim 27 wherein:
the plurality of pieces of exercise equipment include stationary bicycles; and one of the first exercise signal and the second exercise signal corresponds to power.

29. The apparatus of claim 1 wherein the at least one processor is configured to cause the output signal to display on the at least one display device an abstract animation included in the animation that varies in response to the at least two different exercise signals.

30. The apparatus of claim 1 wherein the at least one processor is configured to generate the output signal to cause the animation to provide at least three games wherein in a first game, the animation illustrates an individual effort of each user, in a second game, the animation illustrates both the individual effort of each user and an effort of a group of users, and in a third game, the animation illustrates the effort of a group of users without illustrating individual effort.

31. The apparatus of claim 1 wherein the plurality of exercise signals relating to exercise performance comprise at least one of speed of motion, distance traveled, energy expended, heart rate, blood pressure, blood-oxygen content, and blood-sugar content.

32. A method of communicating exercise results of a class in a graphic form comprising:
receiving, by a computer system, a plurality of exercise signals from each of a plurality of pieces of in the class relating to exercise performance and storing the exercise signals in at least one electronic storage device included in the computer system;
generating, by at least one processor included in the computer system, an output signal containing an animation, the animation including at least one graphic shape, each graphic shape of the at least one graphic shape corresponding to at least two different exercise signals from one piece of the plurality of pieces of exercise equipment, a first exercise signal of the at least two different exercise signals including data relating to a first aspect of exercise performance from the one piece of the plurality of pieces of exercise equipment, and a second exercise signal of the at least two different exercise signals including data relating to a second aspect of exercise performance from the one piece of the plurality of pieces of exercise equipment, each graphic shape animated with a first animated feature corresponding to the first exercise signal and a second animated feature corresponding to the second exercise signal; and
generating a display on at least one display device visible from each piece of the plurality of pieces of exercise equipment in the class from the output signal including the animation.

33. The method of claim 32 wherein the method further comprises, for each graphic shape:
generating, by the at least one processor, the output signal to define the graphic shape; and
causing, by the at least one processor, the graphic shape to spin at a rate related to the first exercise signal and move along a path based on the second exercise signal, wherein the first animated feature includes the spin and the second animated feature includes the move along the path.

34. The method of claim 33 wherein a thickness of a line forming the graphic shape corresponds to a third exercise signal of the plurality of exercise signals.

35. The method of claim 34 wherein the third exercise signal corresponds to power.

36. The method of claim 33 wherein:
the first exercise signal indicates rotation rate or speed of the one piece of the plurality of pieces of exercise equipment; and
the second exercise signal corresponds to distance traveled of the one piece of the plurality of pieces of exercise equipment.

37. The method of claim 33 further comprising causing, by the at least one processor, the graphic shape to change color when a user exercising on the one piece of the plurality of pieces of exercise equipment is on track to at least match a distance from a previous session.

38. The method of claim 33 further comprising causing, by the at least one processor, causes the output signal to produce a display indicating top performers after a predetermined time.

39. The method of claim 32 wherein:
each piece of the plurality of pieces of exercise equipment in the class is organized in one of two or more teams; and
the method further comprises, for each graphic shape, generating, by the at least one processor, the output signal so that the graphic shape drops into a second graphic shape for a corresponding team when at least one exercise signal of the at least two different exercise signals corresponding to the graphic shape achieves a predetermined value, wherein the second graphic shape is different from the graphic shape.

40. The method of claim 39 wherein the graphic shape rotates in response to the second exercise signal and a thickness of a line forming the graphic shape corresponds to a third exercise signal of the plurality of exercise signals, wherein the second animated feature includes rotating.

41. The method of claim 40 wherein:
the plurality of pieces of exercise equipment include a plurality of stationary bicycles; and
the second exercise signal corresponds to rotation rate of a corresponding stationary bicycle and the third exercise signal corresponds to power from the corresponding stationary bicycle.

42. The method of claim 39 wherein the plurality of pieces of exercise equipment are stationary bicycles and the at least one exercise signal corresponds to distance of a corresponding stationary bicycle.

43. The method of claim 39 wherein the method further comprises, when the second graphic shape is completed, generating, by the at least one processor, the output signal to cause another second graphic shape to be built from dropping graphic shapes.

44. The method of claim 32 further comprising generating a display on a user display device of individual information concerning a user.

45. The method of claim 44 wherein the individual information includes cumulative data for the user over the class.

46. The method of claim 45 wherein the individual information includes data comparing the user to the class.

47. The method of claim 44 further comprising accepting, by the user display device, data from the user to register the user for the class.

48. The method of claim 44 further comprising receiving, by the user display device, receiving data from the at least one processor and not directly from the plurality of pieces of exercise equipment.

49. The method of claim 32 wherein the plurality of pieces of exercise equipment include a plurality of stationary bicycles.

50. The method of claim 49 wherein the plurality of exercise signals include signals representing two or more of rotation rate, distance, power and energy.

51. The method of claim 50 wherein one of the plurality of exercise signals representing distance represents a combination of rotation rate and power.

52. The method of claim 32 further comprising causing, by the at least one processor, causes the output signal to display on the at least one display device an abstract animation included in the animation that varies in response to the at least two different exercise signals.

53. The method of claim 32 wherein the plurality of exercise signals relating to exercise performance comprise at least one of speed of motion, distance traveled, energy expended, heart rate, blood pressure, blood-oxygen content, and blood-sugar content.

54. An exercise class apparatus used in a class, the apparatus comprising:
a plurality of pieces of exercise equipment, each piece of the plurality of pieces of exercise equipment configured to output a plurality of exercise signals relating to exercise performance of a user of each piece of the plurality of pieces of exercise equipment in the class, wherein the class includes the users grouped into two or more teams;
a computer system including:
at least one electronic storage device configured to store the plurality of exercise signals;
at least one processor configured to generate an output signal containing an animation, the animation including at least one graphic shape, each graphic shape of the at least one graphic shape corresponding to at least two different exercise signals from one piece of the plurality of pieces of exercise equipment, a first exercise signal of the at least two different exercise signals including data relating to a first aspect of exercise performance from the one piece of the plurality of pieces of exercise equipment, and a second exercise signal of the at least two different exercise signals including data relating to a second aspect of exercise performance from the one piece of the plurality of pieces of exercise equipment, each graphic shape animated with a first animated feature corresponding to the first exercise signal and a second animated feature corresponding to the second exercise signal; and
at least one display device, visible from each of the plurality of pieces of exercise equipment or users in the class, configured to receive the output signal and display the animation.

55. The apparatus of claim 54 wherein:
for each of the at least one graphic shape, the at least one processor is configured to cause the at least one graphic shape to move along a path, the appearance of the at least one graphic shape changing based on the first exercise signal and a distance which the at least one graphic shape moves along the path is responsive to the second exercise signal, wherein the first animated feature includes the changing of the appearance and the second animated feature includes the move along the path.

56. The apparatus of claim 55 wherein:
the plurality of pieces of exercise equipment include stationary bicycles;
the first exercise signal is representative of power; and
the second exercise signal is representative of distance traveled.

57. The apparatus of claim 54 wherein:
the plurality of pieces of exercise equipment include stationary bicycles; and
at least one exercise signal of the plurality of exercise signals corresponds to power.

58. The apparatus of claim 57 wherein after a predetermined time, the at least one processor is configured to generate the output signal to cause the at least one display device to display a user generating the highest average power over the predetermined time.

59. The apparatus of claim 54, wherein the at least one processor is further configured to group the users in the class into the two or more teams.

60. The apparatus of claim 54 wherein:
the plurality of pieces of exercise equipment include stationary bicycles;
at least one exercise signal of the plurality of exercise signals relating to exercise performance of at least one user of a first of the two or more teams and at least one exercise signal of the plurality of exercise signals relating to exercise performance of at least one user of a second of the two or more teams correspond to power; and
at least another exercise signal of the plurality of exercise signals relating to the at least one user of the first of the two or more teams and at least another exercise signal of the plurality of exercise signals relating to the at least one user of the second of the two or more teams correspond to distance.

61. The apparatus of claim 54 wherein the at least one processor is configured to generate the output signal to display individual leaders and class total relative to a goal after a predetermined period of time.

62. The apparatus of claim 54 wherein the plurality of exercise signals relating to exercise performance comprise at least one of speed of motion, distance traveled, energy expended, heart rate, blood pressure, blood-oxygen content, and blood-sugar content.

63. A method of communicating exercise results of a class in a graphic form comprising:
receiving, by a computer system, a plurality of exercise signals from each of a plurality of pieces of exercise equipment relating to exercise performance of a user of each piece of the plurality of pieces of exercise equipment in the class and storing the exercise signals in at least one electronic storage device included in the computer system, wherein the class includes the users grouped into two or more teams;
generating, by at least one processor included in the computer system, an output signal containing an animation, the animation including at least one graphic shape, each graphic shape of the at least one graphic shape corresponding to at least two different exercise signals from one piece of the plurality of pieces of exercise equipment, a first exercise signal of the at least two different exercise signals including data relating to a first aspect of exercise performance from the one piece of the plurality of pieces of exercise equipment, and a second exercise signal of the at least two different exercise signals including data relating to a second aspect of exercise performance from the one piece of the plurality of pieces of exercise equipment, each graphic shape animated with a first animated feature corresponding to the first exercise signal and a second animated feature corresponding to the second exercise signal; and
generating a display on at least one display device visible from each of the plurality of pieces of exercise equipment or users in the class from the output signal including the animation.

64. The method of claim 63 further comprising:
for each of the at least one graphic shape, causing, by the at least one processor, the at least one graphic shape to move along a path, the appearance of the at least one graphic shape changing based on the first exercise signal and a distance which the at least one graphic shape moves along the path is responsive to the second exercise signal, wherein the first animated feature includes the changing of the appearance and the second animated feature includes the move along the path.

65. The method of claim 64 wherein:
the plurality of pieces of exercise equipment include stationary bicycles;
the first exercise signal is representative of power; and the second exercise signal is representative of distance traveled.

66. The method of claim 63 wherein:
the plurality of pieces of exercise equipment include stationary bicycles; and
at least one exercise signal of the plurality of exercise signals corresponds to power.

67. The method of claim 66 further comprising after a predetermined time, generating, by the at least one processor, the output signal to cause the at least one display device to display a user generating the highest average power over the predetermined time.

68. The method of claim 63, further comprising grouping, by the at least one processor, the users in the class into the two or more teams.

69. The method of claim 63 wherein:
the plurality of pieces of exercise equipment include stationary bicycles;
at least one exercise signal of the plurality of exercise signals relating to at least one user of the first of the two or more teams and at least one exercise signal of the plurality of exercise signals relating to at least one user of the second of the two or more teams correspond to power; and
at least another exercise signal of the plurality of exercise signals relating to the at least one user of the first of the two or more teams and at least another exercise signal of the plurality of exercise signals relating to the at least one user of the second of the two or more teams correspond to distance.

70. The method of claim 63 further comprising generating, by the at least one processor, the output signal to display individual leaders and class total relative to a goal after a predetermined period of time.

71. The method of claim 63 wherein the plurality of exercise signals relating to exercise performance comprise at least one of speed of motion, distance traveled, energy expended, heart rate, blood pressure, blood-oxygen content, and blood-sugar content.

* * * * *